US010755810B2

(12) United States Patent
Buckler et al.

(10) Patent No.: US 10,755,810 B2
(45) Date of Patent: Aug. 25, 2020

(54) METHODS AND SYSTEMS FOR REPRESENTING, STORING, AND ACCESSING COMPUTABLE MEDICAL IMAGING-DERIVED QUANTITIES

(71) Applicant: ELUCID BIOIMAGING INC., Boston, MA (US)

(72) Inventors: Andrew J. Buckler, Wenham, MA (US); Keith A. Moulton, Amesbury, MA (US); Mary Buckler, Wenham, MA (US); Larry Martell, Wenham, MA (US); David S. Paik, Half Moon Bay, CA (US); Xiaonan Ma, South Hamilton, MA (US); Samantha St. Pierre, Wenham, MA (US)

(73) Assignee: ELUCID BIOIMAGING INC., Boston, MA (US)

( * ) Notice: Subject to any disclaimer, the term of this patent is extended or adjusted under 35 U.S.C. 154(b) by 573 days.

(21) Appl. No.: 15/237,249

(22) Filed: Aug. 15, 2016

(65) Prior Publication Data
US 2017/0046484 A1 Feb. 16, 2017

Related U.S. Application Data

(60) Provisional application No. 62/205,364, filed on Aug. 14, 2015, provisional application No. 62/205,372, (Continued)

(51) Int. Cl.
*G16H 30/40* (2018.01)
*G16H 10/60* (2018.01)
(Continued)

(52) U.S. Cl.
CPC ............ *G16H 30/40* (2018.01); *G16H 10/60* (2018.01); *G16H 50/20* (2018.01); *G06F 21/6245* (2013.01)

(58) Field of Classification Search
CPC ........ G06Q 50/22; G06Q 50/24; G06F 19/30; G06F 19/32; G06F 19/321; G06F 19/34;
(Continued)

(56) References Cited

U.S. PATENT DOCUMENTS 6,108,635 A 8/2000 Herren et al.
6,245,016 B1 6/2001 Daft
(Continued)

FOREIGN PATENT DOCUMENTS

WO 2015058151 A2 4/2015

OTHER PUBLICATIONS

Buckler et al. "Data Sets for the Qualification of Volumetric CT as a Quantitative Imaging Biomarker in Lung Cancer." Optics Exp. 18.14(2010): 15267-15282.*
(Continued)

*Primary Examiner* — Jason S Tiedeman
(74) *Attorney, Agent, or Firm* — Pearl Cohen Zedek Latzer Baratz LLP

(57) ABSTRACT

Methods and systems are disclosed for structuring and using information pertinent to in vivo biomarkers, specifically quantitative imaging biomarkers, using semantic web technology for personalized medicine and discovery science. It supports the development and application of statistical evidence at a level of granularity and sophistication more closely tied to the complexity of the disease itself and its underlying biology, including technology linking multiple biological scales, than has previously been eedisclosed. It provides data and computational services to analyze quantitative imaging and non-imaging data, coupled with multi-scale modeling to elucidate pre-symptomatic and clinical disease processes. It may be used to assess technical or analytical performance for its own sake and/or to further annotate the quantitative analysis. It supports statistical hypothesis testing to determine and present analytical performance, determine the clinical relevance and establish to what extent a biomarker is causally rather than coincidentally related in clinical contexts of use.

48 Claims, 24 Drawing Sheets

Related U.S. Application Data filed on Aug. 14, 2015, provisional application No. 62/205,384, filed on Aug. 14, 2015, provisional application No. 62/205,388, filed on Aug. 14, 2015, provisional application No. 62/205,394, filed on Aug. 14, 2015, provisional application No. 62/205,401, filed on Aug. 14, 2015, provisional application No. 62/269,473, filed on Dec. 18, 2015, provisional application No. 62/219,870, filed on Sep. 17, 2015.

(51) Int. Cl.
*G16H 50/20* (2018.01)
*G06F 21/62* (2013.01)

(58) Field of Classification Search
CPC ..... G06F 19/36; G06F 21/6245; G16H 10/00; G16H 10/60; G16H 15/00; G16H 30/00; G16H 30/20; G16H 30/40; G16H 50/00; G16H 50/20; G16H 50/50; G16H 50/70
USPC .......................................................... 705/2, 3
See application file for complete search history.

(56) References Cited

U.S. PATENT DOCUMENTS

| | | | |
|---|---|---|---|
| 8,879,813 B1 | 11/2014 | Solanki | |
| 9,773,308 B2* | 9/2017 | Silbersweig | G06T 7/0012 |
| 9,858,529 B2 | 1/2018 | Adams | |
| 2002/0103776 A1* | 8/2002 | Bella | G06K 9/6217 |
| | | | 706/49 |
| 2003/0105638 A1 | 6/2003 | Taira | |
| 2003/0195883 A1* | 10/2003 | Mojsilovic | G06F 19/321 |
| 2005/0043614 A1 | 2/2005 | Huizenga et al. | |
| 2005/0118632 A1 | 6/2005 | Chen et al. | |
| 2005/0144042 A1* | 6/2005 | Joffe | G06Q 50/22 |
| | | | 705/2 |
| 2005/0216243 A1* | 9/2005 | Graham | G16H 50/50 |
| | | | 703/11 |
| 2006/0159367 A1* | 7/2006 | Zeineh | G02B 21/365 |
| | | | 382/276 |
| 2006/0242288 A1* | 10/2006 | Masurkar | G06F 11/0709 |
| | | | 709/223 |
| 2007/0130206 A1 | 6/2007 | Zhou et al. | |
| 2007/0208516 A1* | 9/2007 | Kutsyy | G06K 9/00147 |
| | | | 702/19 |
| 2008/0027695 A1* | 1/2008 | Balgi | G16H 50/20 |
| | | | 703/11 |
| 2008/0201280 A1* | 8/2008 | Martin | G06N 99/005 |
| | | | 706/12 |
| 2009/0043172 A1* | 2/2009 | Zagorchev | A61B 6/032 |
| | | | 600/300 |
| 2009/0171871 A1 | 7/2009 | Zhang et al. | |
| 2009/0258925 A1 | 10/2009 | Wahlestedt | |
| 2009/0259459 A1 | 10/2009 | Ceusters et al. | |
| 2009/0324126 A1 | 12/2009 | Zitnick et al. | |
| 2010/0070448 A1 | 3/2010 | Omoigui | |
| 2010/0262545 A1* | 10/2010 | Herlitz | G06Q 10/00 |
| | | | 705/51 |
| 2011/0026798 A1 | 2/2011 | Madabhushi et al. | |
| 2011/0027181 A1 | 2/2011 | Amodei et al. | |
| 2011/0243407 A1* | 10/2011 | Sofka | G06F 19/321 |
| | | | 382/128 |
| 2012/0082362 A1* | 4/2012 | Diem | A61B 5/0071 |
| | | | 382/133 |
| 2012/0278060 A1 | 11/2012 | Cancedda et al. | |
| 2013/0202173 A1* | 8/2013 | Buckler | G06T 7/0012 |
| | | | 382/131 |
| 2013/0226616 A1* | 8/2013 | Nigam | G06Q 10/00 |
| | | | 705/3 |
| 2013/0275094 A1* | 10/2013 | Ortoleva | G16B 15/00 |
| | | | 703/1 |
| 2014/0126770 A1* | 5/2014 | Odessky | G06F 17/30259 |
| | | | 382/103 |
| 2014/0270440 A1 | 9/2014 | Inglese | |
| 2014/0365239 A1* | 12/2014 | Sadeghi | G06F 19/321 |
| | | | 705/3 |
| 2015/0149201 A1* | 5/2015 | Starmer, Jr. | G06Q 50/22 |
| | | | 705/2 |
| 2015/0154275 A1 | 6/2015 | Senart et al. | |
| 2015/0234921 A1* | 8/2015 | Li | G06Q 10/10 |
| | | | 707/707 |
| 2015/0242607 A1* | 8/2015 | Morris | H04L 9/3231 |
| | | | 713/186 |
| 2015/0272467 A1 | 10/2015 | Warfield et al. | |
| 2015/0317337 A1* | 11/2015 | Edgar | G06Q 10/00 |
| | | | 707/751 |
| 2015/0324527 A1 | 11/2015 | Siegel et al. | |
| 2016/0042508 A1 | 2/2016 | Novikov et al. | |
| 2016/0097716 A1 | 4/2016 | Gulati et al. | |
| 2016/0147954 A1* | 5/2016 | Ng Tari | G16H 40/20 |
| | | | 705/3 |
| 2016/0203599 A1* | 7/2016 | Gillies | A61B 6/463 |
| | | | 382/132 |
| 2016/0314580 A1 | 10/2016 | Lloyd et al. | |
| 2016/0326588 A1* | 11/2016 | Beier | C12Q 1/6883 |
| 2016/0364630 A1 | 12/2016 | Reicher et al. | |
| 2017/0358079 A1 | 12/2017 | Gilles et al. | |
| 2018/0321347 A1 | 11/2018 | Wang | |
| 2019/0019300 A1 | 1/2019 | Simpson | |

OTHER PUBLICATIONS

Buckler, A., et al., A Novel Knowledge Representation Framework for the Statistical Validation of Quantitative Imaging Biomarkers. Journal of Digital Imaging, 2013. 26(4): p. 614-629.*

William B. Kerr et al., "A Methodology and Metric for Quantitative Analysis and Parameter Optimization of Unsupervised, Multi-Region Image Segmentation", Proceeding of the 8th IASTED International Conference on Signal and Image Processing, Aug. 14, 2006, pp. 243-248.*

International Search Report & Written Opinion in co-pending International patent application No. PCT/US16/67463 dated Mar. 10, 2017. (10 Pages).

Hlatky, M.A., et al., Projected Costs and Consequences of Computed Tomography-Determined Fractional Flow Reserve. Clinical cardiology, 2013. 36(12): p. 743-748.

Hoffmann, U., et al., Coronary Computed Tomography Angiography for Early Triage of Patients With Acute Chest Pain: The ROMICAT (Rule Out Myocardial Infarction using Computer Assisted Tomography) Trial. J Am Coll Cardiol, 2009. 53(18): p. 1642-1650.

Hoffmann, U., et al., Coronary CT Angiography versus Standard Evaluation in Acute Chest Pain. N Engl J Med, 2012. 367(4).

Hoffmann, U., et al., Prognostic Value of Noninvasive Cardiovascular Testing in Patients With Stable Chest Pain: Insights From the PROMISE Trial (Prospective Multicenter Imaging Study for Evaluation of Chest Pain). Circulation, 2017. 135(24): p. 2320-2332.

Hofman, J.M.A., et al., Quantification of atherosclerotic plaque components using in vivo MRI and supervised classifiers. Magnetic Resonance in Medicine, 2006. 55(4): p. 790-799.

Hulten, E., et al., Coronary Artery Disease Detected by Coronary Computed Tomographic Angiography Is Associated With Intensification of Preventive Medical Therapy and Lower Low-Density Lipoprotein Cholesterol. Circulation: Cardiovascular Imaging, 2014. 7(4): p. 629-638.

Ibrahimi, P., et al., Coronary and carotid atherosclerosis: How useful is the imaging? Atherosclerosis, 2013. 231(2): p. 323-333.

Insull, W., The pathology of atherosclerosis: plaque development and plaque responses to medical treatment. Am J Med, 2009. 122(1 Suppl): p. S3-S14.

Isbell, D.C., et al., Reproducibility and reliability of atherosclerotic plaque volume measurements in peripheral arterial disease with cardiovascular magnetic resonance. Journal of Cardiovascular Magnetic Resonance, 2007. 9(1): p. 71-76.

Itu, L., et al., A machine-learning approach for computation of fractional flow reserve from coronary computed tomography. Journal of Applied Physiology, 2016. 121(1): p. 42-52.

(56) References Cited

OTHER PUBLICATIONS

Jcgm, J., Evaluation of measurement data—Guide to the expression of uncertainty in measurement. Int. Organ. Stand. Geneva ISBN, 2008. 50: p. 134.

Johnson, A.J., et al., Cohort Study of Structured Reporting Compared with Conventional Dictation. Radiology, 2009. 253(1): p. 74-80.

Johnson, N.P., R.L. Kirkeeide, and K.L. Gould, Is discordance of coronary flow reserve and fractional flow reserve due to methodology or clinically relevant coronary pathophysiology? JACC: Cardiovascular Imaging, 2012. 5(2): p. 193-202.

Joseph A. Ladapo, K.S.G., Pamela S. Douglas, Projected Morbidity and Mortality from Missed Diagnoses of Coronary Artery Disease in the United States. Int J Cardiol, 2015. Sep. 15, 2015: p. 250-252.

Joshi, A.A., et al., GlycA Is a Novel Biomarker of Inflammation and Subclinical Cardiovascular Disease in Psoriasis. Circ Res, 2016. 119(11): p. 1242-1253.

Joshi, F.R., et al., Non-invasive imaging of atherosclerosis. European Heart Journal—Cardiovascular Imaging, 2012. 13(3): p. 205-218.

Juan, S., Stents overused to treat heart patients, in China Daily. 2012: Online, English Edition.

Karlof, E., Correlation of Computed Tomography with Carotid Plaque Transcriptomes Associates Calcification to Lesion-Stabilization (Abstract). 2018, Karolinska Institutet.

Kaul, S. and J. Narula, in search of the vulnerable plaque: is there any light at the end of the catheter? 2014, Journal of the American College of Cardiology.

Kawahara, I., et al., The detection of carotid plaque rupture caused by intraplaque hemorrhage by serial high-resolution magnetic resonance imaging: a case report. Surg Neurol, 2008. 70(6): p. 634-9; discussion 639.

Kawasaki, M., et al., Volumetric Quantitative Analysis of Tissue Characteristics of Coronary Plaques After Statin Therapy Using Three-Dimensional Integrated Backscatter Intravascular Ultrasound. J Am Coll Cardiol, 2005. 45(12): p. 1946-1953.

Kerwin, W., et al., Magnetic resonance imaging of carotid atherosclerosis: plaque analysis. Top Magn Reson Imaging, 2007. 18(5): p. 371-8.

Kerwin, W., et al., Quantitative Magnetic Resonance Imaging Analysis of Neovasculature Volume in Carotid Atherosclerotic Plaque. Circulation, 2003. 107(6): p. 851-856.

Kerwin, W.S., et al., Inflammation in carotid atherosclerotic plaque: a dynamic contrast-enhanced MR imaging study. Radiology, 2006. 241(2): p. 459-68.

Kerwin, W.S., et al., MR imaging of adventitial vasa vasorum in carotid atherosclerosis. Magnetic Resonance in Medicine, 2008. 59(3): p. 507-514.

Kerwin, W.S., et al., Signal features of the atherosclerotic plaque at 3.0 Tesla versus 1.5 Tesla: impact on automatic classification. J Magn Reson Imaging, 2008. 28(4): p. 987-95.

Kholodenko, B.N., Cell-signalling dynamics in time and space. Nat Rev Mol Cell Biol, 2006. 7(3): p. 165-76.

Kini, A.S., et al., Changes in Plaque Lipid Content After Short-Term Intensive Versus Standard Statin Therapy. Journal of the American College of Cardiology, 2013. 62(1): p. 21-9.

Kishi, S., et al., Fractional Flow Reserve Estimated at Coronary CT Angiography in Intermediate Lesions: Comparison of Diagnostic Accuracy of Different Methods to Determine Coronary Flow Distribution. Radiology, 2018. 287(1): p. 76-84.

Kitagawa, T., et al., Characterization of Noncalcified Coronary Plaques and Identification of Culprit Lesions in Patients With Acute Coronary Syndrome by 64-Slice Computed Tomography. JACC: Cardiovascular Imaging, 2009. 2(2): p. 153-160.

Kohsaka, S. and A.N. Makaryus, Coronary angiography using noninvasive imaging techniques of cardiac CT and MRI. Current cardiology reviews, 2008. 4(4): p. 323.

Kolata, G., 'Unbelievable': Heart Stents Fail to Ease Chest Pain, in New York Times. 2017.

Kolossváry, M., et al., Radiomic Features Are Superior to Conventional Quantitative Computed Tomographic Metrics to Identify Coronary Plaques With Napkin-Ring Sign. Circ Cardiovasc Imaging, 2017. 10(12).

Koo, B.K., et al., Diagnosis of ischemia-causing coronary stenoses by noninvasive fractional flow reserve computed from coronary computed tomographic angiograms. Results from the prospective multicenter DISCOVER-FLOW (Diagnosis of Ischemia-Causing Stenoses Obtained Via Noninvasive Fractional Flow Reserve) study. J Am Coll Cardiol, 2011. 58(19): p. 1989-97.

Korn, E.L., P.S. Albert, and L.M. McShane, Assessing surrogates as trial endpoints using mixed models. Statistics in medicine, 2005. 24(2): p. 163-182.

Langlotz, C.P., Enhancing the Expressiveness of Structured Reporting Systems. J. Digit. Imaging, 2000. 13: p. 49-53.

Larose, E, et al., Characterization of Human Atherosclerotic Plaques by Intravascular Magnetic Resonance Imaging. Circulation, 2005. 112(15): p. 2324-2331.

Lavi, S., et al., Segmental coronary endothelial dysfunction in patients with minimal atherosclerosis is associated with necrotic core plaques. Heart, 2009. 95(18): p. 1525-1530.

Lavi, S., et al., The interaction between coronary endothelial dysfunction, local oxidative stress, and endogenous nitric oxide in humans. Hypertension, 2008. 51(1): p. 127-133.

Leber, A.W., et al., Quantification of Obstructive and Nonobstructive Coronary Lesions by 64-Slice Computed Tomography: A Comparative Study With Quantitative Coronary Angiography and Intravascular Ultrasound. J Am Coll Cardiol, 2005. 46(1): p. 147-154.

Levin DC, P.L, Halpern EJ, Rao VM, Coronary CT Angiography: Use in Patients With Chest Pain Presenting to Emergency Departments. American Journal of Roentgenology, 2018. 210(4): p. 4.

Li, D., Z.A. Fayad, and D.A. Bluemke, Can Contrast-Enhanced Cardiac Magnetic Resonance Assess Inflammation of the Coronary Wall? JACC: Cardiovascular Imaging, 2009. 2(5): p. 589-591.

Li, F., et al., Scan-rescan reproducibility of carotid atherosclerotic plaque morphology and tissue composition measurements using multicontrast MRI at 3T. J Magn Reson Imaging, 2010. 31(1): p. 168-76.

Li, T., et al., Classification of Human Coronary Atherosclerotic Plaques Using Ex Vivo High-Resolution Multicontrast-Weighted MRI Compared With Histopathology. American Journal of Roentgenology, 2012. 198(5): p. 1069-1075.

Lindsay, A.C., et al., Plaque Features Associated With Increased Cerebral Infarction After Minor Stroke and TIA: A Prospective, Case-Control, 3-T Carotid Artery MR Imaging Study. JACC: Cardiovascular Imaging, 2012. 5(4): p. 388-396.

Litt, H.I., et al., CT Angiography for Safe Discharge of Patients with Possible Acute Coronary Syndromes. N Engl J Med, 2012. 366(15): p. 1393-403.

Liu, F., et al., Assessment of therapy responses and prediction of survival in malignant pleural mesothelioma through computer-aided volumetric measurement on computed tomography scans. J Thorac Oncol, 2010. 5(6): p. 879-84.

Liu, F., et al., Automated in vivo segmentation of carotid plaque MRI with Morphology-Enhanced probability maps. Magn Reson Med, 2006. 55(3): p. 659-68.

Albuquerque, L.C., et al., Intraplaque hemorrhage assessed by high-resolution magnetic resonance imaging and C-reactive protein in carotid atherosclerosis. Journal of Vascular Surgery, 2007. 46(6): p. 1130-1137.

Alic, L., W.J. Niessen, and J.F. Veenland, Quantification of heterogeneity as a biomarker in tumor imaging: a systematic review. PloS one, 2014. 9(10): p. e110300.

Altaf, N., et al., Detection of intraplaque hemorrhage by magnetic resonance imaging in symptomatic patients with mild to moderate carotid stenosis predicts recurrent neurological events. Journal of Vascular Surgery, 2008. 47(2): p. 337-342.

Altorki, N., et al., Phase II proof-of-concept study of pazopanib monotherapy in treatment-naive patients with stage I/II resectable non-small-cell lung cancer. J Clin Oncol, 2010. 28(19): p. 3131-7.

(56) References Cited

OTHER PUBLICATIONS

Anderson, J.D., et al., Multifactorial Determinants of Functional Capacity in Peripheral Arterial Disease: Uncoupling of Calf Muscle Perfusion and Metabolism. J Am Coll Cardiol, 2009. 54(7): p. 628-635.

Astor, B.C., et al., Remodeling of Carotid Arteries Detected with MR Imaging: Atherosclerosis Risk in Communities Carotid MRI Study. Radiology, 2010. 256(3): p. 879-886.

Awai, K., et al., Pulmonary Nodules: Estimation of Malignancy at Thin-Section Helical CT—Effect of Computer-aided Diagnosis on Performance of Radiologists 1. Radiology, 2006. 239(1): p. 276-284.

Bar, L., N. Sochen, and N. Kiryati, Semi-blind image restoration via Mumford-Shah regularization. IEEE Trans Image Process, 2006. 15(2): p. 483-93.

Barnett, H.J., et al., Benefit of carotid endarterectomy in patients with symptomatic moderate or severe stenosis. North American Symptomatic Carotid Endarterectomy Trial Collaborators. N Engl J Med, 1998. 339(20): p. 1415-25.

Bartlett, E.S., et al., Quantification of Carotid Stenosis on CT Angiography. American Journal of Neuroradiology, 2006. 27(1): p. 13-19.

Behnke, L., Solis A, Schulman SA, Skoufalos A, A Targeted Approach to Reducing Overutilization: Use of Percutaneous Coronary Intervention in Stable Coronary Artery Disease. Population Health Management, 2013. 16(3).

Bishop, C. and C.M. Bishop, Neural networks for pattern recognition. 1995: Oxford university press.

Bluemke, D.A., et al., Noninvasive Coronary Artery Imaging: Magnetic Resonance Angiography and Multidetector Computed Tomography Angiography: A Scientific Statement From the American Heart Association Committee on Cardiovascular Imaging and Intervention of the Council on Cardiovascular Radiology and Intervention, and the Councils on Clinical Cardiology and Cardiovascular Disease in the Young. Circulation, 2008. 118(5): p. 586-606.

Bochem, A.E., et al., ABCA1 mutation carriers with low high-density lipoprotein cholesterol are characterized by a larger atherosclerotic burden. Eur Heart J, 2012.

Boogers, M.J., et al., Automated quantification of coronary plaque with computed tomography: comparison with intravascular ultrasound using a dedicated registration algorithm for fusion-based quantification. Eur Heart J, 2012. 33 (8): p. 1007-1016.

Boogers, M.J., et al., Automated Quantification of Stenosis Severity on 64-Slice CT: A Comparison With Quantitative Coronary Angiography. JACC: Cardiovascular Imaging, 2010. 3(7): p. 699-709.

Bradley, S.M., et al., Normal Coronary Rates for Elective Angiography in the Veterans Affairs Healthcare System: Insights From the VA CART Program (Veterans Affairs Clinical Assessment Reporting and Tracking). J Am Coll Cardiol, 2014. 63(5): p. 417-426.

Brandman, S. and J.P. Ko, Pulmonary nodule detection, characterization, and management with multidetector computed tomography. Journal of Thoracic Imaging, 2011. 26(2): p. 90-105.

Brodoefel, H., et al., Accuracy of dual-source CT in the characterisation of non-calcified plaque: use of a colour-coded analysis compared with virtual histology intravascular ultrasound. The British Journal of Radiology, 2009. 82(982): p. 805-812.

Brodoefel, H., et al., Characterization of coronary atherosclerosis by dual-source computed tomography and HU-based color mapping: a pilot study. European radiology, 2008. 18(11): p. 2466-2474.

Brott, T.G., et al., 2011 ASA/ACCF/AHA/AANN/AANS/ACR/ASNR/CNS/SAIP/SCAI/SIR/SNIS/SVM/SVS Guideline on the Management of Patients With Extracranial Carotid and Vertebral Artery Disease. Circulation, 2011. 124: p. e54-e130.

Brott, T.G., et al., Long-Term Results of Stenting versus Endarterectomy for Carotid-Artery Stenosis. N Engl J Med, 2016. 374(11): p. 1021-31.

Buyse, M., et al., Statistical validation of surrogate endpoints: problems and proposals. Drug Information Journal, 2000. 34(2): p. 447-454.

Cai, J.M., et al., Classification of human carotid atherosclerotic lesions with in vivo multicontrast magnetic resonance imaging. Circulation, 2002. 106(11): p. 1368-73.

Cappendijk, V.C., et al., Assessment of human atherosclerotic carotid plaque components with multisequence MR imaging: initial experience. Radiology, 2005. 234(2): p. 487-92.

Carter, H.H., et al., Evidence for Shear Stress-Mediated Dilation of the Internal Carotid Artery in Humans. Hypertension, 2016. 68(5): p. 1217-1224.

Caselles, V., R. Kimmel, and G. Sapiro, Geodesic Active Contours. International Journal on Computer Vision, 1997. 22 (1): p. 61-97.

Chang HJ, F.Y.L., et al. Coronary Atherosclerotic Precursors of Acute Coronary Syndromes. Journal of the American College of Cardiology (JACC), 2018. 71(22).

Chang, A.M., et al., Actual Financial Comparison of Four Strategies to Evaluate Patients with Potential Acute Coronary Syndromes. Academic Emergency Medicine, 2008. 15(7): p. 649-655.

Chinnaiyan, K.M., et al., Coronary computed tomography angiography after stress testing: results from a multicenter, statewide registry, ACIC (Advanced Cardiovascular Imaging Consortium). Journal of the American College of Cardiology, 2012. 59(7): p. 688-695.

Ciccone, M.M., et al., Cardiovascular risk evaluation and prevalence of silent myocardial ischemia in subjects with asymptomatic carotid artery disease. Vasc Health Risk Manag, 201t 7: p. 129-34.

Collobert, R., et al., Natural language processing (almost) from scratch. Journal of Machine Learning Research, Aug. 12, 2011: p. 2493-2537.

Davies, J.R., et al., Radionuclide Imaging for the Detection of Inflammation in Vulnerable Plaques. J Am Coll Cardiol, 2006. 47(8, Supplement): p. C57-C68.

De Bruyne, B., et al., Fractional flow reserve-guided PCI for stable coronary artery disease. New England Journal of Medicine, 2014. 371(13): p. 1208-1217.

Depairon, M., Cardiovascular risk prediction with ultrasound. Cardiovascular Medicine, 2010. 13(9): p. 255-264.

Dey, D. and F. Commandeur, Radiomics to Identify High-Risk Atherosclerotic Plaque From Computed Tomography: The Power of Quantification. Circ Cardiovasc Imaging, 2017. 10(12).

Dey, D., et al., Automated 3-dimensional quantification of noncalcified and calcified coronary plaque from coronary CT angiography. Journal of Cardiovascular Computed Tomography, 2010. 3(6): p. 372-382.

Dodd, J.D., et al., Quantification of Nonculprit Coronary Lesions: Comparison of Cardiac 64-MDCT and Invasive Coronary Angiography. American Journal of Roentgenology, 2008. 191(2): p. 432-438.

Du, R., et al., Early decrease in carotid plaque lipid content as assessed by magnetic resonance imaging during treatment of rosuvastatin. BMC Cardiovascular Disorders, 2014. 14(1): p. 83.

Duivenvoorden, R., et al., In Vivo Quantification of Carotid Artery Wall Dimensions: 3.0-Tesla MRI Versus B-Mode Ultrasound Imaging. Circulation: Cardiovascular Imaging, 2009. 2(3): p. 235-242.

Ederle, J., et al., Carotid artery stenting compared with endarterectomy in patients with symptomatic carotid stenosis (International Carotid Stenting Study): an interim analysis of a randomised controlled trial. Lancet, 2010. 375(9719): p. 985-97.

Ernst, C.B., HeartFlow Announces Positive Medical Coverage Decisions on Non-Invasive HeartFlow® FFRct Analysis from Anthem Blue Cross Blue Shield, Blue Shield of California and Blue Cross and Blue Shield of Alabama. 2017, Heartflow Inc.: Redwood City, Calif.

Esposito, L., et al., MRI plaque imaging reveals high-risk carotid plaques especially in diabetic patients irrespective of the degree of stenosis. BMC Medical Imaging, 2010. 10(1): p. 27.

Esposito-Bauer, L., et al., MRI Plaque Imaging Detects Carotid Plaques with a High Risk for Future Cerebrovascular Events in Asymptomatic Patients. PLoS One, 2013. 8(7): p. e67927.

F D Kolodgie, R.V., A P Burke, A Farb, D K Weber, R Kutys, A V Finn, H K Gold, Pathologic assessment of the vulnerable human coronary plaque. Heart, 2004. 90.

Fayad, Z.A., et al., Magnetic Resonance Imaging of Atherosclerotic Plaque, I.P. WO/2005/079274, Editor, May 9, 2005.

(56) References Cited

OTHER PUBLICATIONS

Ferencik, M., et al., Use of High-Risk Coronary Atherosclerotic Plaque Detection for Risk Stratification of Patients With Stable Chest Pain: A Secondary Analysis of the PROMISE Randomized Clinical Trial. JAMA Cardiol, 2018. 3(2): p. 144-152.

Fuchs, T., et al., Coronary artery calcium quantification from contrast enhanced CT using gemstone spectral imaging and material decomposition. Int J Cardiovasc Imaging, 2014. 30(7): p. 1399-1405.

Fuster, V. and P.R. Moreno, Atherothrombosis as a systemic, often silent, disease. Nat Clin Pract Cardiovasc Med, 2005. 2(9): p. 431.

Gao, T., Z. Zhang, and W. Yu, Atherosclerotic Carotid Vulnerable Plaque and Subsequent Stroke: A High-Resolution MRI Study. Atherosclerotic Carotid Vulnerable Plaque and Subsequent Stroke: A High-Resolution MRI Study, 2009. 27: p. 345-352.

Garcia-Garcia, H.M., M.A. Costa, and P.W. Serruys, Imaging of coronary atherosclerosis: intravascular ultrasound. Eur Heart J, 2010. 31(20): p. 2456-69.

Gerretsen, S., et al., Detection of coronary plaques using MR coronary vessel wall imaging: validation of findings with intravascular ultrasound. European radiology, 2013. 23(1): p. 115-124.

Gerretsen, S.C., et al., Visualization of Coronary Wall Atherosclerosis in Asymptomatic Subjects and Patients with Coronary Artery Disease Using Magnetic Resonance Imaging. PLoS One, 2010. 5(9): p. e12998.

Gibbons, R.J., High-Risk Coronary Atherosclerotic Plaque Assessment by Coronary Computed Tomography Angiography—Should We Use It? JAMA Cardiol, 2018. 3(2): p. 153-154.

Glagov, S., et al., Compensatory enlargement of human atherosclerotic coronary arteries. N Engl J Med, 1987. 316 (22): p. 1371-5.

Gnasso, A., et al., In vivo association between low wall shear stress and plaque in subjects with asymmetrical carotid atherosclerosis. Stroke, 1997. 28(5): p. 993-8.

Goldstein, J.A., et al., The CT-STAT (Coronary Computed Tomographic Angiography for Systematic Triage of Acute Chest Pain Patients to Treatment) Trial. J Am Coll Cardiol, 2011. 58(14): p. 1414-1422.

Gonzalo, N., et al., Morphometric Assessment of Coronary Stenosis Relevance With Optical Coherence Tomography: A Comparison With Fractional Flow Reserve and Intravascular Ultrasound. J Am Coll Cardiol, 2012. 59(12): p. 1080-1089.

Gouya, H., et al., Coronary Artery Stenosis in High-risk Patients: 64-Section CT and Coronary Angiography—Prospective Study and Analysis of Discordance. Radiology, 2009. 252(2): p. 377-385.

Grimm, J., et al., Comparison of symptomatic and asymptomatic atherosclerotic carotid plaques using parallel imaging and 3T black-blood in vivo CMR. Journal of Cardiovascular Magnetic Resonance, 2013. 15(1): p. 44.

Gupta, A., et al., Cost-Effectiveness of Carotid Plaque MR Imaging as a Stroke Risk Stratification Tool in Asymptomatic Carotid Artery Stenosis. Radiology, 2015: p. 142843.

Gupta, A., et al., CT angiographic features of symptom-producing plaque in moderate-grade carotid artery stenosis. AJNR Am J Neuroradiol, 2015. 36(2): p. 349-54.

Gupta, A., et al., Evaluation of computed tomography angiography plaque thickness measurements in high-grade carotid artery stenosis. Stroke, 2014. 45(3): p. 740-5.

Gupta, A., et al., Magnetic resonance angiography detection of abnormal carotid artery plaque in patients with cryptogenic stroke. Journal of the American Heart Association, 2015. 4(6): p. e002012.

Gupta, A., et al., Semi-Automated Detection of High-Risk Atherosclerotic Carotid Artery Plaque Features from Computed Tomography Angiography, in European Stroke Conference. 2017: Berlin.

Hamdan, A., et al., A Prospective Study for Comparison of MR and CT Imaging for Detection of Coronary Artery Stenosis. JACC: Cardiovascular Imaging, 2011.4(1): p. 50-61.

Harder, D.R., et al., Functional hyperemia in the brain: hypothesis for astrocyte-derived vasodilator metabolites. Stroke, 1998. 29(1): p. 229-234.

Hardie, A.D., et al., The impact of expansive arterial remodeling on clinical presentation in carotid artery disease: a multidetector CT angiography study. AJNR Am J Neuroradiol, 2007.28(6): p. 1067-70.

Hassani-Pak, K. and C. Rawlings, Knowledge Discovery in Biological Databases for Revealing Candidate Genes Linked to Complex Phenotypes. J Integr Bioinform, 2017. 14(1).

Hatsukami, T.S. and C. Yuan, MRI in the early identification and classification of high-risk atherosclerotic carotid plaques. Imaging in Medicine, 2010. 2(1): p. 63-75.

Hatsukami, T.S., et al., Visualization of Fibrous Cap Thickness and Rupture in Human Atherosclerotic Carotid Plaque In Vivo With High-Resolution Magnetic Resonance Imaging. Circulation, 2000. 102(9): p. 959-964.

Haug, P.J., et al., A natural language parsing system for encoding admitting diagnoses. Proc AMIA Annu Fall Symp, 1997: p. 814-8.

Haug, P.J., et al., A natural language understanding system combining syntactic and semantic techniques. Proc Annu Symp Comput Appl Med Care, 1994: p. 247-51.

Hermann, D.M., et al., Coronary Artery Calcification Is an Independent Stroke Predictor in the General Population. Stroke, 2013.

Hideya Yamamoto, Y.K., Toshiro Kitagawa, Norihiko Ohashi, Eiji Kunita, Yoshitaka Iwanaga, Kazuhiro Kobuke, Shunichi Miyazaki, Tomohiro Kawasaki, Shinichiro Fujimoto, Hiroyuki Daida, Takashi Fujii, Aki Sato, Tomokazu Okimoto, Sachio Kuribayashi, Coronary plaque characteristics in computed tomography and 2-year outcomes: The PREDICT study. Journal of Cardiovascular Computed Tomography, 2018. Article in Press.

Underhill, H.R., et al., Arterial remodeling in [corrected] subclinical carotid artery disease. JACC Cardiovasc Imaging, 2009. 2(12): p. 1381-9.

Underhill, H.R., et al., Automated measurement of mean wall thickness in the common carotid artery by MRI: a comparison to intima-media thickness by B-mode ultrasound. J Magn Reson Imaging, 2006. 24(2): p. 379-87.

van den Bouwhuijsen, Q.J.A., et al., Determinants of magnetic resonance imaging detected carotid plaque components: the Rotterdam Study. Eur Heart J, 2012. 33(2): p. 221-229.

van 't Klooster, R., et al., Automated Versus Manual In Vivo Segmentation of Carotid Plaque MRI. American Journal of Neuroradiology, 2012. 33(8): p. 1621-1627.

van't Klooster, R., et al., Automatic lumen and outer wall segmentation of the carotid artery using deformable three-dimensional models in MR angiography and vessel wall images. Journal of Magnetic Resonance Imaging, 2012. 35(1): p. 156-165.

Vegsundvåg, J., et al., Coronary Flow Velocity Reserve in the Three Main Coronary Arteries Assessed with Transthoracic Doppler: A Comparative Study with Quantitative Coronary Angiography. Journal of the American Society of Echocardiography, 2011. 24(7): p. 758-767.

Virmani, R., et al., Lessons from sudden coronary death: a comprehensive morphological classification scheme for atherosclerotic lesions. Arterioscler Thromb Vasc Biol, 2000. 20(5): p. 1262-75.

Vliegenthart, R., et al., Dual-Energy CT of the Heart. American Journal of Roentgenology, 2012. 199(5_supplement): p. S54-S63.

von Birgelen, C., et al., Relation Between Progression and Regression of Atherosclerotic Left Main Coronary Artery Disease and Serum Cholesterol Levels as Assessed With Serial Long-Term (=12 Months) Follow-Up Intravascular Ultrasound. Circulation, 2003. 108(22): p. 2757-2762.

Voros, S., et al., Prospective Validation of Standardized, 3-Dimensional, Quantitative Coronary Computed Tomographic Plaque Measurements Using Radiofrequency Backscatter Intravascular Ultrasound as Reference Standard in Intermediate Coronary Arterial Lesions: Results From the ATLANTA I Study. JACC: Cardiovascular Interventions, 2011. 4(2): p. 198-208.

Vukadinovic, D., Automated Quantification of Atherosclerosis in CTA of Carotid Arteries. 2012: Erasmus University Rotterdam.

Wagenknecht, L., et al., Correlates of Carotid Plaque Presence and Composition as Measured by MRI: The Atherosclerosis Risk in Communities Study. Circulation: Cardiovascular Imaging, 2009. 2(4): p. 314-322.

(56) References Cited

OTHER PUBLICATIONS

Walker, L.J., et al., Computed tomography angiography for the evaluation of carotid atherosclerotic plaque correlation with histopathology of endarterectomy specimens. Stroke, 2002. 33(4): p. 977-981.
Wan, T., et al., Spatio-temporal texture (SpTeT) for distinguishing vulnerable from stable atherosclerotic plaque on dynamic contrast enhancement (DCE) MRI in a rabbit model. Medical Physics, 2014. 41(Apr. 2014).
Wasserman, B.A., et al., Carotid artery atherosclerosis: in vivo morphologic characterization with gadolinium-enhanced double-oblique MR imaging initial results. Radiology, 2002. 223(2): p. 566-73.
Wasserman, B.A., et al., MRI measurements of carotid plaque in the atherosclerosis risk in communities (ARIC) study: Methods, reliability and descriptive statistics. Journal of Magnetic Resonance Imaging, 2010. 31(2): p. 406-415.
Wasserman, B.A., et al., Risk Factor Associations With the Presence of a Lipid Core in Carotid Plaque of Asymptomatic Individuals Using High-Resolution MRI: The Multi-Ethnic Study of Atherosclerosis (MESA). Stroke, 2008. 39(2): p. 329-335.
Weichert, W. and A. Warth, Early lung cancer with lepidic pattern: adenocarcinoma in situ, minimally invasive adenocarcinoma, and lepidic predominant adenocarcinoma. Current opinion in pulmonary medicine, 2014. 20(4): p. 309-316.
Williams MC, M.A., Nicol E, Newby DE, Cardiac CT Improves Outcomes in Stable Coronary Heart Disease: Results of Recent Clinical Trials. Current Cardiovascular Imaging Reports, 2017. 10(14).
Yong, A.S., et al., The relationship between coronary artery distensibility and fractional flow reserve. PloS one, 2017. 12(7): p. e0181824.
Yoon, Y.E., et al., Noninvasive diagnosis of ischemia-causing coronary stenosis using CT angiography: diagnostic value of transluminal attenuation gradient and fractional flow reserve computed from coronary CT angiography compared to invasively measured fractional flow reserve. JACC: Cardiovascular Imaging, 2012. 5(11): p. 1088-1096.
Yoshida, K, et al., Characterization of Carotid Atherosclerosis and Detection of Soft Plaque with Use and Black-Blood Mr Imaging. American Journal of Roentgenology, 2008. 29: p. 868-874.
Zainon, R., et al., Spectral CT of carotid atherosclerotic plaque: comparison with histology. European radiology, 2012. 22(12): p. 2581-2588.
Zhao, Q., et al., Association between coronary artery calcium score and carotid atherosclerotic disease. Molecular medicine reports, 2013. 8(2): p. 499-504.
Zhao, Q., et al., Association of Coronary Calcification and Carotid Artery Morphology: a High Resolution Magnetic Resonance Imaging Study. Proc. Intl. Soc. Mag. Reson. Med. 17, 2009. 17: p. 27.
Zhao, Q., et al., Correlation of Coronary Plaque Phenotype and Carotid Atherosclerotic Plaque Composition. The American Journal of the Medical Sciences, 2011. 342(6): p. 480-485 10.1097/MAJ.0b013e31821caa88.
Zhao, X., et al., Discriminating carotid atherosclerotic lesion severity by luminal stenosis and plaque burden: a comparison utilizing high-resolution magnetic resonance imaging at 3.0 Tesla. Stroke, 2011. 42(2): p. 347-53.
Burzykowski, T., et al., Evaluation of tumor response, disease control, progression-free survival, and time to progression as potential surrogate end points in metastatic breast cancer. J Clin Oncol, 2008. 26(12): p. 1987-92.
Gaston A. Rodriguez-Granillo1, Patricia Carrascosal, Nico Bruining3, and a.H.M.G.-G. RonWaksman4, Defining the non-vulnerable and vulnerable patients with computed tomography coronary angiography: evaluation of atherosclerotic plaque burden and composition. European Heart Journal—Cardiovascular Imaging, 2016. 2016(17): p. 481-491.
International Search & Written Opinion in co-pending International patent application No. PCT/US2016/065132, dated Mar. 17, 2017.
International Search & Written Opinion in co-pending International patent application No. PCT/US2018/046483, dated Feb. 5, 2019.

Perisic, L.M. and U. Hedin, Unstable Plaque: from patient to molecule to patient, in Cardiology. 2018, Karolinska Institutet: HLF Stora Forskningsanlaget.
Pijls, N.H., et al., Fractional flow reserve versus angiography for guiding percutaneous coronary intervention in patients with multivessel coronary artery disease: 2-year follow-up of the FAME (Fractional Flow Reserve Versus Angiography for Multivessel Evaluation) study. Journal of the American College of Cardiology, 2010. 56(3): p. 177-184.
Pijls, N.H., et al., Percutaneous Coronary Intervention of Functionally Nonsignificant Stenosis 5-Year Follow-Up of the DEFER Study. JACC, 2007. 49(21): p. 2105-11.
Polak, J.F., et al., Carotid artery plaque and progression of coronary artery calcium: the multi-ethnic study of atherosclerosis. J Am Soc Echocardiogr, 2013.26(5): p. 548-55.
Polonsky, T.S., et al., Coronary artery calcium score and risk classification for coronary heart disease prediction. JAMA, 2010. 303(16): p. 1610-1616.
Puchner, S.B., et al., High-Risk Plaque Detected on Coronary CT Angiography Predicts Acute Coronary Syndromes Independent of Significant Stenosis in Acute Chest Pain: Results From the ROMICAT-II Trial. J Am Coll Cardiol, 2014. 64(7): p. 684-692.
Puntmann, V.O., How-to guide on biomarkers: biomarker definitions, validation and applications with examples from cardiovascular disease. Postgraduate Medical Journal, 2009. 85(1008): p. 538-545.
Pyxaras, S.A., et al., Quantitative angiography and optical coherence tomography for the functional assessment of nonobstructive coronary stenoses: Comparison with fractional flow reserve. Am Heart J, 2013. 166(6): p. 1010-1018. e1.
Qiao, Y., et al., Carotid Plaque Neovascularization and Hemorrhage Detected by MR Imaging are Associated with Recent Cerebrovascular Ischemic Events. American Journal of Neuroradiology, 2012. 33(4): p. 755-760.
Qiao, Y., et al., Identification of atherosclerotic lipid deposits by diffusion-weighted imaging. Arterioscler Thromb Vasc Biol, 2007. 27(6): p. 1440-6.
Räber, L., et al., Effect of high-intensity statin therapy on atherosclerosis in non-infarct-related coronary arteries (IBIS-4): a serial intravascular ultrasonography study. Eur Heart J, 2014.
Raff, G.L., et al., Diagnostic Accuracy of Noninvasive Coronary Angiography Using 64-Slice Spiral Computed Tomography. J Am Coll Cardiol, 2005. 46(3): p. 552-557.
Rinehart, S., et al., Quantitative measurements of coronary arterial stenosis, plaque geometry, and composition are iighly reproducible with a standardized coronary arterial computed tomographic approach in high-quality CT datasets. Journal of Cardiovascular Computed Tomography, 2011. 5(1): p. 35-43.
Roes, S.D., et al., Aortic vessel wall magnetic resonance imaging at 3.0 Tesla: A reproducibility study of respiratory navigator gated free-breathing 3D black blood magnetic resonance imaging. Magnetic Resonance in Medicine, 2009. 61(1): p. 35-44.
Saam, T., et al., The vulnerable, or high-risk, atherosclerotic plaque: noninvasive MR imaging for characterization and assessment. Radiology, 2007. 244(1): p. 64-77.
Sakuma, H., Coronary CT versus MR Angiography: The Role of MR Angiography. Radiology, 2011. 258(2): p. 340-349.
Salem, M.K., et al., Identification of Patients with a Histologically Unstable Carotid Plaque Using Ultrasonic Plaque Image Analysis. European Journal of Vascular and Endovascular Surgery, 2014. 48(2): p. 118-125.
Sanak, D., et al., The role of magnetic resonance imaging for acute ischemic stroke. Biomed Pap Med Fac Univ Palacky Olomouc Czech Repub, 2009. 153(3): p. 181-7.
Saur, S.C., et al., Contrast enhancement with dual energy CT for the assessment of atherosclerosis, in Bildverarbeitung für die Medizin 2009. 2009, Springer. p. 61-65.
Schaar, J.A., et al., Terminology for high-risk and vulnerable coronary artery plaques. Report of a meeting on the vulnerable plaque, Jun. 17 and 18, 2003, Santorini, Greece. Eur Heart J, 2004. 25(12): p. 1077-82.

(56) References Cited

OTHER PUBLICATIONS

Schepis, T., et al., Quantification of non-calcified coronary atherosclerotic plaques with dual-source computed tomography: comparison with intravascular ultrasound. Heart, 2010. 96(8): p. 610-615.
Schneeweis, C., et al., Delayed Contrast-Enhanced MRI of the Coronary Artery Wall in Takayasu Arteritis. PLoS One, 2012. 7(12): p. e50655.
Schuetz, G.M., et al., Meta-analysis: Noninvasive Coronary Angiography Using Computed Tomography Versus Magnetic Resonance Imaging. Ann Intern Med, 2010. 152(3): p. 167-177.
Scott, A.D., et al., Noninvasive detection of coronary artery wall thickening with age in healthy subjects using high resolution MRI with beat-to-beat respiratory motion correction. Journal of Magnetic Resonance Imaging, 2011. 34(4): p. 824-830.
Sheahan, M., et al., Atherosclerotic Plaque Tissue: Noninvasive Quantitative Assessment of Characteristics with Software-aided Measurements from Conventional CT Angiography. Radiology, 2017: p. 170127.
Silvera, S.S., et al., Multimodality imaging of atherosclerotic plaque activity and composition using FDG-PET/CT and MRI in carotid and femoral arteries. Atherosclerosis, 2009. 207(1): p. 139-43.
Sirimarco, G., et al., Carotid Atherosclerosis and Risk of Subsequent Coronary Event in Outpatients With Atherothrombosis. Stroke, 2013. 44(2): p. 373-379.
Sorger, P.K., Quantitative and systems pharmacology in the postgenomic era: New approaches to discovering drugs and understanding therapeutic mechanisms. QSP White Paper. 2011.
Spaan, J.A., et al., Physiological basis of clinically used coronary hemodynamic indices. Circulation, 2006. 113(3): p. 446-455.
St Pierre, S., et al., Measurement Accuracy of Atherosclerotic Plaque Structure on CT Using Phantoms to Establish Ground Truth. Acad Radiol, 2017(DOI 10.1016/j.acra.2017.04.007).
Stefanini, G.G. and S. Windecker, Can coronary computed tomography angiography replace invasive angiography? Coronary computed tomography angiography cannot replace invasive angiography. Circulation, 2015. 131(4): p. 418-25; discussion 426.
Steinvil, A., et al., Impact of Carotid Atherosclerosis on the Risk of Adverse Cardiac Events in Patients With and Without Coronary Disease. Stroke, 2014. 45(8): p. 2311-2317.
Strauss, H.W. and J. Narula, Imaging Vulnerable Plaque: A Medical Necessity or a Scientific Curiosity?*. Journal of the American College of Cardiology, 2017. 69(14): p. 1792-1794.
Symons, R., et al., Coronary CT Angiography: Variability of CT Scanners and Readers in Measurement of Plaque Volume. Radiology, 2016. 281(3): p. 737-748.
Takaya, N., et al., Presence of Intraplaque Hemorrhage Stimulates Progression of Carotid Atherosclerotic Plaques: A High-Resolution Magnetic Resonance Imaging Study. Circulation, 2005. 111(21): p. 2768-2775.
Tartari, S., et al., High-Resolution MRI of Carotid Plaque With a Neurovascular Coil and Contrast-Enhanced MR Angiography: One-Stop Shopping for the Comprehensive Assessment of CArotid Atherosclerosis. American Journal of Roentgenology, 2011. 196(5): p. 1164-1171.
Tesche, C., et al., Coronary CT angiography—derived fractional flow reserve: machine learning algorithm versus computational fluid dynamics modeling. Radiology, 2018: p. 171291.
Tesche, C., et al., Prognostic implications of coronary CT angiography-derived quantitative markers for the prediction of major adverse cardiac events. J Cardiovasc Comput Tomogr, 2016. 10(6): p. 458-465.
Tonino, P.A., et al., Angiographic versus functional severity of coronary artery stenoses in the FAME study: fractional low reserve versus angiography in multivessel evaluation. Journal of the American College of Cardiology, 2010. 55 (25): p. 2816-2821.
Trelles, M., et al., CTA for Screening of Complicated Atherosclerotic Carotid Plaque—American Heart Association Type VI Lesions as Defined by MRI. American Journal of Neuroradiology, 2013. 34(12): p. 2331-2337.
Tu, S., et al., A novel three-dimensional quantitative coronary angiography system: In-vivo comparison with intravascular ultrasound for assessing arterial segment length. Catheterization and Cardiovascular Interventions, 2010. 16(2): p. 291-298.
Tu, S., et al., In vivo comparison of arterial lumen dimensions assessed by co-registered three-dimensional (3D) quantitative coronary angiography, intravascular ultrasound and optical coherence tomography. Int J Cardiovasc Imaging, 2012. 28(6): p. 1315-1327.
U-King-Im, J.M., et al., Characterization of Carotid Plaque Hemorrhage: A CT Angiography and MR Intraplaque Hemorrhage Study. Stroke, 2010. 41(8): p. 1623-1629.
Underhill, H., et al., Differences in carotid arterial morphology and composition between individuals with and without obstructive coronary artery disease: A cardiovascular magnetic resonance study. Journal of Cardiovascular Magnetic Resonance, 2008. 10(1): p. 31.
Underhill, H.R., et al., A noninvasive imaging approach to assess plaque severity: the carotid atherosclerosis score. AJNR Am J Neuroradiol, 2010. 31(6): p. 1068-75.
Liu, R., et al., Noninvasive numerical simulation of coronary fractional flow reserve baed on lattice Boltzmann method. Sheng wu yi xue gong cheng xue za zhi= Journal of biomedical engineering= Shengwu yixue gongchengxue zazhi, 2018. 35(3): p. 384-389.
Mackey, R.H., L. Venkitachalam, and K. Sutton-Tyrrell, Calcifications, arterial stiffness and atherosclerosis. Adv Cardiol, 2007. 44: p. 234-44.
Magge, R., et al., Clinical Risk Factors and CT Imaging Features of Carotid Atherosclerotic Plaques as Predictors of New Incident Carotid Ischemic Stroke: A Retrospective Cohort Study. American Journal of Neuroradiology, 2013. 34 (2): p. 402-409.
Maier, D., et al., Knowledge management for systems biology a general and visually driven framework applied to translational medicine. BMC Syst Biol, 2011. 5: p. 38.
Maintz, D., et al., Selective coronary artery plaque visualization and differentiation by contrast-enhanced inversion prepared MRI. Eur Heart J, 2006.27(14): p. 1732-6.
Maitland, M.L., Volumes to learn: advancing therapeutics with innovative computed tomography image data analysis. Clin Cancer Res, 2010. 16(18): p. 4493-5.
Makowski, M.R. and R.M. Botnar, MR Imaging of the Arterial Vessel Wall: Molecular Imaging from Bench to Bedside. Radiology, 2013. 269(1): p. 34-51.
Makowski, M.R., et al., Characterization of coronary atherosclerosis by magnetic resonance imaging. Circulation, 2013. 128(11): p. 1244-55.
Maldonado, F., et al., Non-invasive Characterization of the Histopathologic Features of Pulmonary Nodules of the Lung Adenocarcinoma Spectrum using Computer Aided Nodule Assessment and Risk Yield (CANARY)—a Pilot Study. Journal of thoracic oncology: official publication of the International Association for the Study of Lung Cancer, 2013. 8 (4): p. 452.
Mani, V., et al., Predictors of change in carotid atherosclerotic plaque inflammation and burden as measured by 18-FDG-PET and MRI, respectively, in the dal-PLAQUE study. Int J Cardiovasc Imaging, 2014. 30(3): p. 571-582.
Mannelli, L., et al., Changes in measured size of atherosclerotic plaque calcifications in dual-energy CT of ex vivo carotid endarterectomy specimens: effect of monochromatic keV image reconstructions. European radiology, 2013. 23 (2): p. 367-374.
Marwick TH, C.I., Hartaigh B, Min JK, Finding the Gatekeeper to the Cardiac Catheterization Laboratory Coronary CT Angiography or Stress Testing? Journal of the American College of Cardiology (JACC), 2015. 65(25): p. 10.
May, J.M., et al., Low-Risk Patients With Chest Pain in the Emergency Department: Negative 64-MDCT Coronary Angiography May Reduce Length of Stay and Hospital Charges. American Journal of Roentgenology, 2009. 193(1): p. 150-154.
Meijboom, W.B., et al., Comprehensive assessment of coronary artery stenoses: computed tomography coronary angiography versus conventional coronary angiography and correlation with fractional flow reserve in patients with stable angina. Journal of the American College of Cardiology, 2008. 52(8): p. 636-643.

(56) References Cited

OTHER PUBLICATIONS

Melikian, N., et al., Fractional flow reserve and myocardial perfusion imaging in patients with angiographic multivessel coronary artery disease. JACC: Cardiovascular Interventions, 2010. 3(3): p. 307-314.

Miao, C., et al., Positive Remodeling of the Coronary Arteries Detected by Magnetic Resonance Imaging in an Asymptomatic Population: MESA (Multi-Ethnic Study of Atherosclerosis). J Am Coll Cardiol, 2009. 53(18): p. 1708-1715.

Min, J.K., et al., Diagnostic accuracy of fractional flow reserve from anatomic CT angiography. JAMA, 2012. 308(12): p. 1237-45.

Min, J.K., Y. Chandrashekhar, and J. Narula, Noninvasive FFR After STEMI Looking for the Guilty Bystander. JACC Cardiovasc Imaging, 2017. 10(4): p. 500-502.

Min, J.K., Y. Chandrashekhar, and J. Narula, The Immediate Effects of Statins on Coronary Atherosclerosis: Can Phenotype Explain Outcome? JACC Cardiovasc Imaging, 2017.

Moschetti, K., et al., Comparative cost-effectiveness analyses of cardiovascular magnetic resonance and coronary angiography combined with fractional flow reserve for the diagnosis of coronary artery disease. Journal of Cardiovascular Magnetic Resonance, 2014. 16(1): p. 13.

Moss AJ, W.M., Newby DE, Nicol ED, The Updated NICE Guidelines: Cardiac CT as the First-Line Test for Coronary Artery Disease. Curr Cardiovasc Imaging Rep., 2017. 10(5): p. 5.

Motoyama, S., et al., Computed tomographic angiography characteristics of atherosclerotic plaques subsequently resulting in acute coronary syndrome. Journal of the American College of Cardiology, 2009. 54(1): p. 49-57.

Motoyama, S., et al., Morphologic and Functional Assessment of Coronary Artery Disease; Potential Application of Computed Tomography Angiography and Myocardial Perfusion Imaging. Circulation Journal, 2013. 77(2): p. 411-417.

Motoyama, S., et al., Multislice computed tomographic characteristics of coronary lesions in acute coronary syndromes. J Am Coll Cardiol, 2007. 50(4): p. 319-26.

Motoyama, S., et al., Plaque characterization by coronary computed tomography angiography and the likelihood of acute coronary events in mid-term follow-up. Journal of the American College of Cardiology, 2015. 66(4): p. 337-346.

Muntendam, P., et al., The BioImage Study: Novel approaches to risk assessment in the primary prevention of atherosclerotic cardiovascular disease—study design and objectives. Am Heart J, 2010. 160(1): p. 49-57.e1.

Nair, A., et al., Coronary Plaque Classification With Intravascular Ultrasound Radiofrequency Data Analysis. Circulation, 2002. 106(17): p. 2200-2206.

Nakanishi, R. and M.J. Budoff, Noninvasive FFR derived from coronary CT angiography in the management of coronary artery disease: technology and clinical update. Vascular health and risk management, 2016. 12: p. 269.

Nissen, S.E., The Vulnerable Plaque "Hypothesis": Promise, but Little Progress. JACC: Cardiovascular Imaging, 2009. 2(4): p. 483-485.

Nørgaard, B.L, et al., Diagnostic performance of noninvasive fractional flow reserve derived from coronary computed tomography angiography in suspected coronary artery disease: the NXT trial (Analysis of Coronary Blood Flow Using CT Angiography: Next Steps). J Am Coll Cardiol, 2014. 63(12): p. 1145-1155.

Obaid, D.R., et al., Atherosclerotic Plaque Composition and Classification Identified by Coronary Computed Tomography: Assessment of Computed Tomography-Generated Plaque Maps Compared With Virtual Histology Intravascular Ultrasound and Histology. Circulation: Cardiovascular Imaging, 2013: p. 655-664.

Obaid, D.R., et al., Dual-energy computed tomography imaging to determine atherosclerotic plaque composition: A prospective study with tissue validation. Journal of Cardiovascular Computed Tomography, 2014. 8(3): p. 230-237.

Obaid, D.R., et al., Identification of Coronary Plaque Sub-Types Using Virtual Histology Intravascular Ultrasound Is Affected by Inter-Observer Variability and Differences in Plaque Definitions. Circulation: Cardiovascular Imaging, 2012. 5(1): p. 86-93.

Oberoi, S., et al., Reproducibility of Noncalcified Coronary Artery Plaque Burden Quantification From Coronary CT Angiography Across Different Image Analysis Platforms. American Journal of Roentgenology, 2011 202(1): p. W43- W49.

Oikawa, M., et al., Carotid magnetic resonance imaging. A window to study atherosclerosis and identify high-risk plaques. Circ J, 2009. 73(10): p. 1765-73.

Okubo, M., et al., Tissue Characterization of Coronary Plaques : Comparison of Integrated Backscatter Intravascular Ultrasound With Virtual Histology Intravascular Ultrasound. Circ J, 2008. 72(10): p. 1631-1639.

Ota, H., et al., Carotid intraplaque hemorrhage imaging at 3.0-T MR imaging: comparison of the diagnostic performance of three T1-weighted sequences. Radiology, 2010. 254(2): p. 551-63.

Ota, H., et al., Hemorrhage and large lipid-rich necrotic cores are independently associated with thin or ruptured fibrous caps: an in vivo 3T MRI study. Arterioscler Thromb Vasc Biol, 2009. 29(10): p. 1696-701.

Pandya, A., et al., Carotid Artery Stenosis: Cost-effectiveness of Assessment of Cerebrovascular Reserve to Guide Treatment of Asymptomatic Patients. Radiology, 2014. 274(2): p. 455-463.

Park, S.-J., et al., Visual-functional mismatch between coronary angiography and fractional flow reserve. JACC: Cardiovascular Interventions, 2012. 5(10): p. 1029-1036.

Parmar, J.P., et al., Magnetic Resonance Imaging of Carotid Atherosclerotic Plaque in Clinically Suspected Acute Transient Ischemic Attack and Acute Ischemic Stroke. Circulation, 2010. 122(20): p. 2031-2038.

Pearson, T.A., et al., Markers of Inflammation and Cardiovascular Disease: Application to Clinical and Public Health Practice: A Statement for Healthcare Professionals From the Centers for Disease Control and Prevention and the American Heart Association. Circulation, 2003. 107(3): p. 499-511.

Choi et al. "Multiscale image segmentation using wavelet-domain hidden Markov models" IEEE Trans Image Process, Sep. 1, 200 (Sep. 1, 2001), vol. 10.

Khan et al., "Robust atlas-based brain segmentation using multi-structure confidence-weighted registration" Proceedings of the 12th International Conference on Medical Imaging Computing, Sep. 20, 2009.

Bourque et al. "Usefulness of Cardiovascular Magnetic Resonance Imaging of the Superficial Femoral Artery for Screening Patients with Diabetes Mellitus for Artherosclerosis." Am. J. Cardiol. 110. 1(2012):50-5.

Buckler et al. "Quantitative Imaging Test Approval and Biomarker Qualification: Interrelated but Distinct Activities." Radiol. 259. 3(2011):875-884.

Buyse et al. "The Validation of Surrogate Endpoints in Meta-Analysis of Randomized Experiments." Biostat. 1 (2000)1-19.

Shan et al. "Active Contours without Edges." IEEE Trans. Image Process. 10.2(2001):266-277.

de Weert et al. "In Vivo Characterization and Quantification of Atherosclerotic Carotid Plaque Components with Multidetector Computed Tomography and Histopathological Correlation." Arterioscler. Thromb. Vasc. Biol. 26.10 (2006)2366-2372.

Fleming. "Surrogate Endpoints and FDA's Accelerated Approval Process." Health Affairs. 24.1(2005):67-78.

Kerwin et al. "MRI of Carotid Artherosclerosis." Am. J. Roentgenol. 200.(2013):W304-W313.

Prentice, "Surrogate Endpoints in Clinical Trials: Definition and Operational Criteria." Stat. Med. 9(1989):431-440.

Sargent et al. "Validation of Novel Imaging Methodologies for Use as Cancer Clinical Trial End-points." Eur. J. Dis. 45 (2009)290-299.

Zavodni et al. "Carotid Artery Plaque Morphology and Composition in Relation to Incident Cardiovascular Events: The Multi-Ethnic Study of Atherosclerosis (MESA)." Radiol. 271.2(2014):361-389.

(56) References Cited

OTHER PUBLICATIONS

Pijils, N.H.J., B. de Bruyne, K Peels, P.H. van der Voort, H.J.R.M. Bonnier, J. Bartunek, and J.J. Koolen, Measurement of Fractional Flow Reserve to Assess the Functional Severity of Coronary-Artery Stenoses. New England Journal of Medicine, 1996. 334(26): p. 1703-1708.
Achenbach, S., et al., Assessment of coronary remodeling in stenotic and nonstenotic coronary atherosclerotic lesions by multidetector spiral computed tomography. J Am Coll Cardiol, 2004. 43(5): p. 842-847.
Achenbach, S., et al., Detection of Calcified and Noncalcified Coronary Atherosclerotic Plaque by Contrast-Enhanced, Submillimeter Multidetector Spiral Computed Tomography: A Segment-Based Comparison With Intravascular Ultrasound. Circulation, 2004. 109(1): p. 14-17.
Agner, S., Xu, J, Madabhushi, A Spectral Embedding based Active Contour (SEAC): Applications to DCE MRI, in SPIE Medical Imaging. 2011, SPIE. p. In Press.
Agner, S.C., et al., Textural Kinetics: A Novel Dynamic Contrast-Enhanced (DCE)-MRI Feature for Breast Lesion Classification. Journal of Digital Imaging, 2010.
Ahmadi, A., A. Kini, and J. Narula, Discordance between ischemia and stenosis, or PINSS and NIPSS: are we ready for new vocabulary? 2015, JACC: Cardiovascular Imaging.
Ahmadi, A., et al., Do plaques rapidly progress prior to myocardial infarction? The interplay between plaque vulnerability and progression. Circulation research, 2015. 117(1): p. 99-104.
Aerts, H.J.W.L., et al., Decoding tumour phenotype by noninvasive imaging using a quantitative radiomics approach. Nat Commun, 2014. 5.
Ahmadi, A., et al., Association of Coronary Stenosis and Plaque Morphology With Fractional Flow Reserve and Outcomes. JAMA Cardiol, 2016. 1(3): p. 350-7.
Ahmadi, A., et al., Lesion-Specific and Vessel-Related Determinants of Fractional Flow Reserve Beyond Coronary Artery Stenosis. JACC Cardiovasc Imaging, 2018. 11(4): p. 521-530.
Albuquerque, L.C., et al., Intraplaque hemorrhage assessed by high-resolution magnetic resonance imaging and C-reactive protein in carotid atherosclerosis. Journal of Vascular Surgery. 46(6): p. 1130-1137.
Alimohammadi, M., et al., Development of a Patient-Specific Multi-Scale Model to Understand Atherosclerosis and Calcification Locations: Comparison with In vivo Data in an Aortic Dissection. Front Physiol, 2016. 7: p. 238.
Aoki, T., et al., Peripheral Lung Adenocarcinoma: Correlation of Thin-Section CT Findings with Histologic Prognostic Factors and Survival 1. Radiology, 2001.220(3): p. 803-809.
Atkinson, A.J., et al., Biomarkers and surrogate endpoints: Preferred definitions and conceptual framework*. Clinical Pharmacology & Therapeutics, 2001. 69(3): p. 89-95.
Bittencourt, M.S., et al., Prognostic Value of Nonobstructive and Obstructive Coronary Artery Disease Detected by Coronary Computed Tomography Angiography to Identify Cardiovascular Events. Circulation: Cardiovascular Imaging, 2014. 7(2): p. 282-291.
Buckler, A.J., et al., Quantitative imaging biomarker ontology (QIBO) for knowledge representation of biomedical imaging biomarkers. Journal of digital imaging : the official journal of the Society for Computer Applications in Radiology, 2013. 26(4): p. 630-41.
Buckler, A.J., et al., Quantitative imaging test approval and biomarker qualification: interrelated but distinct activities. Radiology, 2011. 259(3): p. 875-84.
Buyse, M., et al., The validation of surrogate endpoints in meta-analyses of randomized experiments. Biostatistics, 2000. 1(1): p. 49-67.
Cai, J., et al., In vivo quantitative measurement of intact fibrous cap and lipid-rich necrotic core size in atherosclerotic carotid plaque: comparison of high-resolution, contrast-enhanced magnetic resonance imaging and histology. Circulation, 2005. 112(22): p. 3437-44.
Chan, T.F. and L.A. Vese, Active contours without edges. IEEE Trans Image Process, 2001. 10(2): p. 266-77.
Coenen, A., et al., Diagnostic accuracy of a machine-learning approach to coronary computed tomographic angiography-based fractional flow reserve: result from the MACHINE consortium. Circulation: Cardiovascular Imaging, 2018. 11(6): p. e007217.
de Bono, B., et al., The Open Physiology workflow: modeling processes over physiology circuitboards of interoperable tissue units. Front Physiol, 2015. 6: p. 24.
de Graaf, M., et al., Automatic quantification and characterization of coronary atherosclerosis with computed tomography coronary angiography: cross-correlation with intravascular ultrasound virtual histology. Int J Cardiovasc Imaging, 2013. 29(5): p. 1177-1190.
de Weert, T.T., et al., In Vivo Characterization and Quantification of Atherosclerotic Carotid Plaque Components With Multidetector Computed Tomography and Histopathological Correlation. Arterioscler Thromb Vasc Biol, 2006. 26(10): p. 2366-2372.
DeMarco, J.K. and J. Huston, Imaging of high-risk carotid artery plaques: current status and future directions. Neurosurgical Focus, 2014. 36(1): p. E1.
Diaz-Zamudio, M., et al., Automated Quantitative Plaque Burden from Coronary CT Angiography Noninvasively Predicts Hemodynamic Significance by using Fractional Flow Reserve in Intermediate Coronary Lesions. Radiology, 2015. 276(2): p. 408-15.
Dong, L., et al., Carotid Artery Atherosclerosis: Effect of Intensive Lipid Therapy on the Vasa Vasorum—Evaluation by Using Dynamic Contrast-enhanced MR Imaging. Radiology, 2011. 260(1): p. 224-231.
Filardi, V., Carotid artery stenosis near a bifurcation investigated by fluid dynamic analyses. The neuroradiology journal, 2013. 26(4): p. 439-453.
Fleming, T.R. and D.L. DeMets, Surrogate end points in clinical trials: are we being misled? Ann Intern Med, 1996. 125(7): p. 605-13.
Freimuth, R.R., et al., Life sciences domain analysis model. J Am Med Inform Assoc, 2012. 19(6): p. 1095-102.
Fujimoto, S., et al., A novel method for non-invasive plaque morphology analysis by coronary computed tomography angiography. Int J Cardiovasc Imaging, 2014. 30(7): p. 1373-1382.
Gaston A. Rodriguez-Granillo1, Patricia Carrascosa1, Nico Bruining3, and a.H.M.G.-G. RonWaksman4, Defining the non-vulnerable and vulnerable patients with computed tomography coronary angiography: evaluation of atherosclerotic plaque burden and composition. European Heart Journal—Cardiovascular Imaging, 2016. 2016(17): p. 481-491.
Gevaert, O., et al., Non-small cell lung cancer: identifying prognostic imaging biomarkers by leveraging public gene expression microarray data—methods and preliminary results. Radiology, 2012. 264(2): p. 387-396.
Ghazalpour, A., et al., Thematic review series: The pathogenesis of atherosclerosis. Toward a biological network for atherosclerosis. J Lipid Res, 2004. 45(10): p. 1793-805.
Gupta, A., et al., Carotid Plaque MRI and Stroke Risk A Systematic Review and Meta-analysis. Stroke, 2013.44(11): p. 3071-3077.
Gupta, A., et al., Detection of Symptomatic Carotid Plaque Using Source Data from MR and CT Angiography: A Correlative Study. Cerebrovasc Dis, 2015. 39(3-4): p. 151-61.
Gupta, A., et al., Intraplaque high-intensity signal on 3D time-of-flight MR angiography is strongly associated with symptomatic carotid artery stenosis. American Journal of Neuroradiology, 2014. 35(3): p. 557-561.
Hecht, H.S., Coronary artery calcium scanning: past, present, and future. JACC Cardiovasc Imaging, 2015. 8: p. 579-596.
Hecht, H.S., J. Narula, and W.F. Fearon, Fractional Flow Reserve and Coronary Computed Tomographic Angiography: A Review and Critical Analysis. Circ Res, 2016. 119(2): p. 300-16.
Helft, G., et al., Progression and regression of atherosclerotic lesions: monitoring with serial noninvasive magnetic resonance imaging. Circulation, 2002. 105(8): p. 993-8.
Inoue, K., et al., Serial Coronary CT Angiography—Verified Changes in Plaque Characteristics as an End Point: Evaluation of Effect of Statin Intervention. JACC: Cardiovascular Imaging, 2010. 3(7): p. 691-698.

(56) References Cited

OTHER PUBLICATIONS

Krizhevsky, A., I. Sutskever, and G.E. Hinton. Imagenet classification with deep convolutional neural networks. in Advances in neural information processing systems. 2012.
Lobatto, M.E., et al., Multimodal Clinical Imaging to Longitudinally Assess a Nanomedical Anti-Inflammatory Treatment in Experimental Atherosclerosis. Molecular Pharmaceutics, 2010. 7(6): p. 2020-2029.
Ma, X., et al., Volumes Learned: It Takes More Than Size to "Size Up" Pulmonary Lesions. Acad Radiol, 2016. 23(9): p. 1190-8.
Melander, O., et al., Novel and conventional biomarkers for prediction of incident cardiovascular events in the community. JAMA : the journal of the American Medical Association, 2009. 302(1): p. 49-57.
Miao, C., et al., The Association of Pericardial Fat with Coronary Artery Plaque Index at MR Imaging: The Multi-Ethnic Study of Atherosclerosis (MESA). Radiology, 2011. 261(1): p. 109-115.
Mono, M.L., et al., Plaque Characteristics of Asymptomatic Carotid Stenosis and Risk of Stroke. Cerebrovascular Diseases, 2012. 34(5-6): p. 343-350.
Narula, J., et al., Histopathologic characteristics of atherosclerotic coronary disease and implications of the findings for the invasive and noninvasive detection of vulnerable plaques. Journal of the American College of Cardiology, 2013. 61 (10): p. 1041-1051.
Naylor, A.R., Identifying the high-risk carotid plaque. The Journal of Cardiovascular Surgery, 2014. 55(2): p. 11-20.
Perera, R. and P. Nand, Recent Advances in Natural Language Generation: A Survey and Classification of the Empirical Literature. vol. 36. 2017. 1-31.
Prentice, R.L., Surrogate endpoints in clinical trials: definition and operational criteria. Statistics in medicine, 1989. 8 (4): p. 431-440.
Prescott, J., Quantitative Imaging Biomarkers: The Application of Advanced Image Processing and Analysis to Clinical and Preclinical Decision Making. Journal of Digital Imaging, 2013. 26(1): p. 97-108.
Saba, L., et al., Carotid Artery Plaque Characterization Using CT Multienergy Imaging. American Journal of Neuroradiology, 2013. 34(4): p. 855-859.
Sadot, A., et al., Toward verified biological models. IEEE/ACM Trans Comput Biol Bioinform, 2008. 5(2): p. 223-34.
Sargent, D., et al., Validation of novel imaging methodologies for use as cancer clinical trial end-points. European Journal of Cancer, 2009. 45(2): p. 290-299.
Stary, H.C., et al., A definition of advanced types of atherosclerotic lesions and a histological classification of atherosclerosis A report from the Committee on Vascular Lesions of the Council on Arteriosclerosis, American Heart Association. Circulation, 1995. 92(5): p. 1355-1374.
Stary, H.C., Natural history and histological classification of atherosclerotic lesions: an update. Arterioscler Thromb Vasc Biol, 2000.20(5): p. 1177-8.
Ariff et al. "Carotid Artery Hemodynamics: Observing Patient-specific Changes with Amlodipine and Lisinopril by Using MRI Imaging Computation Fluid Dynamics." Radiol. 257.3(2010):662-669.
Bourque et al. "Usefulness of Cardiovascular Magnetic Resonance Imaging of the Superficial Femoral Artery for Screening Patients with Diabetes Mellitus for Artherosclerosis." Am. J. Cardiol. 110. 1(2012):50-56.
Buckler et al. "A Collaborative Enterprise for Multi-Stakeholder Participation in the Advancement of Quantitative Imaging." Radiol. 258.3(2011):906-914.
Buckler et al. "Data Sets for the Qualification of CT as a Quantitative Imaging Biomarker in Lung Cancer." Optics Exp. 18.14(2010)16.
Buckler et al. "Standardization of Quantitative Imaging: The Time is Right and 18F-FDG PET/CT is a Good Place to Start" J. Nuclear Med. 52.2(2011):171-172.
Buckler et al. "The Use of Volumetric CT as an Imaging Biomarker in Lung Cancer." Acadmic Radiol. 17.1 (2010):100-106.

Buckler et al. "Volumetric CT in Lung Cancer: An Example for the Qualification of Imaging as a Biomarker." Academic Radiol. 17.1(2010):107-115.
Freedman et al. "Statistical Validation of Intermediate Endpoints for Chronic Diseases." Stat. Med. 11(1992):167-178.
Fuleihan et al. "Reproducibility of DXA Absorptiometry: A Model for Bone Loss Estimates." J. Bone Miner. Res. 10.74 (1995):1004-1014.
Horie et al. "Assessment of Carotid Plaque Stability Based on Dynamic Enhancement Pattern in Plaque Components with Multidetector CT Angiography." Stroke. 43.2(2012):393-398.
Irace et al. "Human Common Carotid Wall Shear Stress as a Function of Age and Gender: A 12-year Follow-up Study." AGE. 34.6(2012):1553-1562.
Jaffe, "Measures of Response: RECIST, WHO, and New Alternatives." J. Clin. Oncol. 24.20(2006):3245-3251.
Katz, "Biomarkers and Surrogate Markers: An FDA Perspective." NeuroRx. 12(2004):189-195.
Kerwin et al. "MRI of Carotid Artherosclerosis." Am. J. Roentgenol. 200.3(2013):W304-W313.
Kim et al. "A Curve Evolution-based variational approach to Simultaneous Image Restoration and Segmentation." IEEE Int. Conf. Image Proc. (2002):1-109.
Lathia et al. "The Value, Qualification, and Regulatory Use of Surrogate End Points in Drug Development." Clin. Pharmacol. Therapeutics. 86.1(2009):32-43.
Mozley et al. "Change in Lung Tumor Volume as a Biomarker of Treatment Response: A Critical Review of the Evidence." Ann. Oncol. 21.9(2010):1751-1755.
Phinikaridou et al. "Regions of Low Endothelial Shear Stress Colocalize with Positive Vascular Remodeling and Atherosclerotic Plaque Disruption: An in vivo Magnetic Resonance Imaging Study." Circ. Cardiovasc. Imaging. 6.2 (2013):302-310.
Sui et al. "Assessment of Wall Shear Stress in the Common Carotid Artery of Healthy Subjects Using 3.0-Tesla Magentic Resonanance." Acta Radiologica. 49.4(2008):442-449.
ten Kate et al. "Noninvasive Imaging of the Vulnerable Atherosclerotic Plaque." Current Problems Cardiol. 35.11 (2010):556-591.
Van Klavern et al. "Management of Lung Nodules Detected by Volume CT Scanning." New Engl. J. Med. 361 (2009):23.
Varma et al. "Coronary Vessel Wall Contrast Enhancement Imaging as a Potential Direct Marker of Coronary Involvement: Integration of Findings from CAD and SLE Patients." JACC Cardiovasc. Imaging. 7.8(2014):762-770.
Wintermark et al. "Carotid Plaque CT Imaging in Stroke and Non-Stroke Patients." Ann. Neurol. 64.2(2008):149-157.
Wintermark et al. "High-Resolution CT Imaging of Carotid Artery Atherosclerotic Plaques." Am. J. Neuroradiol. 29.5 (2008):875-882.
Wong et al. "Imaging in Drug Discovery, Preclinical, and Early Clinical Development." J. Nuclear Med. 49.6 (2008):26N-28N.
Woodcock et al. "The FDA Critical Path Initiative and its Influence on New Drug Development." Annu. Rev. Med. 59 (2008):1-12.
Zhao et al. "Evaluating Variability in Tumor Measurements from Same-Day Repeat CT Scans of Patients with Non-Small Cell Lung Cancer." Radiol. 252.1(2009):263-272.
van 't Klooster, R., et al., Visualization of Local Changes in Vessel Wall Morphology and Plaque Progression in Serial Carotid Artery Magnetic Resonance Imaging. Stroke, 2014. 45(8): p. e160-e163.
Virmani, R., et al., Pathology of the Vulnerable Plaque. JACC, 2006.47(8): p. C13-8.
Voros, S., et al., Coronary Atherosclerosis Imaging by Coronary CT Angiography. JACC Cardiovasc Imaging, 2011. 4 (5): p. 537-48.
Zavodni, A.E.H., et al., Carotid Artery Plaque Morphology and Composition in Relation to Incident Cardiovascular Events: The Multi-Ethnic Study of Atherosclerosis (MESA). Radiology, 2014. 271(2): p. 381-389.
Castellano et al. "Texture analysis of medical images," Clinical Radiology, Dec. 1, 2004 (Dec. 1, 2004) vol. 59.
Choi et al. "Multiscale image segmentation using wavelet-domain hidden Markov models" IEEE Trans Image Process, Sep. 1, 2001 (Sep. 1, 2001), vol. 10.

(56) References Cited

OTHER PUBLICATIONS

Reddy et al. "Confidence guided enhancing brain tumor segmentation in multi-parametric MRI" Proceedings of the 12th International Conference on Medical Image Computing and Computer-Assisted Intervention, MICCAI 2009, held in London, UK, Sep. 20, 2009.
Khan et al. "Robust atlas-based brain segmentation using multi-structure confidence-weighted registration" Proceedings of the 12th International Conference on Medical Image Computing, Sep. 20, 2009.
International Search Report & Written Opinion in co-pending international patent application No. PCT/US2016/065132 dated Mar. 17, 2017.
Chan et al., Variational PDE Models in Image Processing. Notices of the AMS. 2004.50(1):p. 14-26.
Chan et al., Variational Image Deblurring—A Window into Mathematical Image Processing. WSPC/Lecture Notes. 2004.
Goatman et al., Detection of New Vessels on the Optic Disc Using Retinal Photographs. IEEE Transactions on Medical Imaging. 2011. 30(4):p. 972-979.

* cited by examiner

- processed_technical_performance
  - 2016-07-19_070805
    - MaxMaxWallThickness
    - process_technical_performance.log
    - results.json
    - MaxRemodelingRatio
    - MaxDilationByDiameter
    - NASCETStenosisCategory
    - MaxStenosisByDiameter
    - CALCVol
  - 2016-07-19_020005
    - FIBRAreaProp
    - process_technical_performance.log
    - results.json
    - IPHAreaProp
    - IPHArea
    - LRNCAreaProp
    - FIBRArea
    - CALCArea
    - CALCAreaProp
    - LRNCArea
  - 2016-07-18_091004
  - 2016-07-17_020003
  - 2016-07-16_020009
  - 2016-07-15_010006
  - 2016-07-14_135240
  - 2016-07-14_071005
  - 2016-07-14_010005
  - 2016-07-13_130002
  - 2016-07-12_010108
  - 2016-07-11_010006
  - 2016-07-10_091741
  - 2016-07-10_010028

FIG. 12

METHODS AND SYSTEMS FOR REPRESENTING, STORING, AND ACCESSING COMPUTABLE MEDICAL IMAGING-DERIVED QUANTITIES

CROSS-REFERENCE TO RELATED APPLICATIONS

The subject application claims priority to and benefit of U.S. Provisional Application No. 62/269,473, filed on Dec. 18, 2015, 62/219,870, filed on Sep. 17, 2015, 62/205,372, 62/205,384, 62/205,388, 62/205,394, 62/205,401, and 62/205,364, all of which were filed on Aug. 14, 2015, the contents of which are incorporated by reference herein in their entirety and for all purposes.

STATEMENT REGARDING FEDERALLY SPONSORED RESEARCH/DEVELOPMENT

This work supported in part by NSF SBIR Award 1248316 and NIH SBIR Award R44 HL126224-01A1 and the government may have certain rights to the work.

BACKGROUND

These teachings relate generally to methods and systems for making image-derived information available to enable analyses with semantic annotations accessible using semantic web technology for personalized medicine and discovery science.

Despite high levels of diagnostician competency levels, accurate assessment of cardiovascular disease, cancer, and other disease categories often rely on relatively simple observations as standard of care. From its inception, imaging has allowed visualization of the in vivo characteristics of disease. Increasingly incisive clinical insights are possible and image analysis methods are continuously developed to implement them, yet the increasing capability requires ever more sophisticated computational techniques to exploit.

Imaging, particularly with safe and non-invasive methods, represents the most powerful methods for locating the disease origin, capturing its detailed pathology, directing therapy, and monitoring progression to health. Imaging is also an extremely valuable and low cost method to mitigate human and financial costs by allowing for appropriate early interventions that are both less expensive and disruptive.

Quantitative imaging techniques are developed for use in the clinical care of patients and in the conduct of clinical trials. In clinical practice, quantitative imaging may be used to detect and characterize disease before, during, and after a course of therapy, and used to predict the course of disease.

Quantitative imaging assessment of phenotype implemented in an architecture which proactively optimizes interoperability with modern clinical IT systems provides power to the clinician as they manage their patients across the continuum of disease severity for improved patient classification across surgical, medical, and surveillance pathways. More timely and accurate assessments yield improved outcomes and more efficient use of health care resources, benefits that far outweigh the cost of the tool—at a level of granularity and sophistication closer to the complexity of the disease itself rather than holding the assumption that it can be simplified to a level which belies the underlying biology.

With newer high resolution imaging techniques, unaided, the radiologist would "drown" in data. Integrating quantitative imaging for individual patient management will require a new class of decision support informatics tools to fully exploit the capabilities of these new tools within the realities of existing work flows.

Ex vivo biomarkers (e.g., genomic, proteomic, etc.) as well as in vivo biomarkers (e.g., imaging) are of particular interest in drug development for their potential to accelerate the drug development pipeline. Various collaborative efforts have been established to coordinate efforts in biomarker discovery and development. On the material side, numerous biobanks (e.g., Karolinska Institute Biobank, British Columbia BioLibrary) store patient tissue and fluid samples that can later be allotted for ex vivo biomarker research. In addition to biological samples, probes and tracers can also be banked. The Radiotracer Clearinghouse has been developed to broker the sharing of Positron Emission Tomography (PET) and Single Positron Emission Computed Tomography radiotracers between stakeholders for in vivo biomarker research. On the information side, various databases store information on ex vivo biomarkers (e.g., Early Detection Research Network Biomarker Database, Infectious Disease Biomarker Database). However, information resources for in vivo biomarkers, specifically quantitative imaging biomarkers, are notably lacking.

Quantitative imaging techniques also have potential applications in translational research. In clinical research, quantitative imaging biomarkers are used to define endpoints of clinical trials. There is a large and growing body of knowledge at the molecular/cellular and organism level enabling quantitative imaging techniques in computer-aided detection, diagnosis, and targeted therapies. Technology linking these levels through the analysis of quantitative imaging and non-imaging data, coupled with multi-scale modeling elucidates both pre-symptomatic and clinical disease processes. Although there is great value in application of quantitative imaging techniques in translational research, few technologies facilitate bridging the two bodies of knowledge; at the molecular/cellular level and at the organism level.

Statistical hypothesis testing is usually stated along with a characterization of variability under defined scenarios. Determining the clinical relevance of a quantitative imaging readout is a difficult problem. It is important to establish to what extent a biomarker reading is an intermediate endpoint capable of being measured prior to a definitive endpoint that is causally rather than coincidentally related. A logical and mathematical framework is needed to establish how extant study data may be used to establish performance in contexts that have not been explicitly tested.

However, existing capabilities only rarely relate the logical world of ontology development with the biostatistical analyses that characterize performance. In general, existing tools do not permit the extrapolation of statistical validation results along arbitrary ontology hierarchies. Despite decades of using statistical validation approaches, there is no methodology to formally represent the generalizability of a validation activity.

SUMMARY

The present invention improves the current standard of care by enabling a quantitative and granular in vivo characteristics of disease by using sophisticated computational techniques to express detailed information which may be used to direct therapy and monitor progression to health by enabling previously unexploited quantitative imaging techniques to express phenotype implemented in an architecture which proactively optimizes interoperability with modern clinical IT systems at a level of granularity and sophistication closer to the complexity of the disease itself rather than holding the assumption that it can be simplified to a level which belies the underlying biology.

The present invention is addressed to the problem of clinician data overload by enabling a new class of decision support informatics tools to within the realities of existing work flows. The present invention provides information resources for in vivo biomarkers development and application to define endpoints of clinical trials which may be coupled with multi-scale modeling of both pre-symptomatic and clinical disease processes The invention supports statistical hypothesis testing to determine and present analytical performance, determine the clinical relevance and establish to what extent a biomarker reading is an intermediate endpoint capable of being measured prior to a definitive endpoint that is causally rather than coincidentally related. The present invention provides a logical and mathematical framework to establish how extant study data may be used to establish performance in contexts that have not been explicitly tested. The present invention relates the logical world of ontology development with the biostatistical analyses that characterize performance, enabling the extrapolation of statistical validation results along arbitrary ontology hierarchies, and enabling formal generalization of a validation activity.

In one or more embodiments, the method of these teachings includes representing an identification scheme for individual cases comprising demographics, observations, findings, and other descriptive information, characterizing targets for image analysis to the one case to support tracking of a given anatomy, suspected pathology, confirmed pathology, or medical intervention at one or more timepoints, storing access information to one or more medical images of each target at each timepoint, storing one or more levels of image-derived analysis, the image-derived analysis comprising at least one of imaging features, measured quantities, phenotypic descriptions, or predictions relative to the one case, the one or more levels of image-derived analysis being obtained by: obtaining a group of medical images corresponding to the one case, calculating imaging features for the group of medical images, applying a machine learning trained method, possibly incorporating one or more non-imaging inputs, in order to obtain quantitative properties, hereinafter referred to as analytes for the one case, and using the analytes to obtain a group of phenotypes for the one case. The method, in the one or more embodiments, also includes providing semantic search ability to access any stored data item, individually or in sets, within or across cases, within or across studies, within or across groups, within or across targets, for imaging or non-imaging associated data, according to concepts in an ontology according to relationships, without requiring the queries to be defined beforehand, the data store hereinafter referred to as a knowledgebase.

In one instance, the semantic search ability includes a component that traverses concepts in an ontology according to relationships, and the method of these teachings further includes applying the component that traverses concepts in an ontology according to relationships, using an imaging ontology, in order to obtain a number of Resource Description Framework (RDF) triples; the number of RDF triples hereinafter referred to as a triple store.

A number of other embodiments are also disclosed.

For a better understanding of the present teachings, together with other and further needs thereof, reference is made to the accompanying drawings and detailed description and its scope will be pointed out in the appended claims.

BRIEF DESCRIPTION OF THE DRAWINGS

FIG. 12 shows an exemplary organization of performance metrics and extractions enabled by the invention, in this view seen as a summary of performance data processed in periodic runs based on running queries and performing analyses.

DETAILED DESCRIPTION

Figure 1:
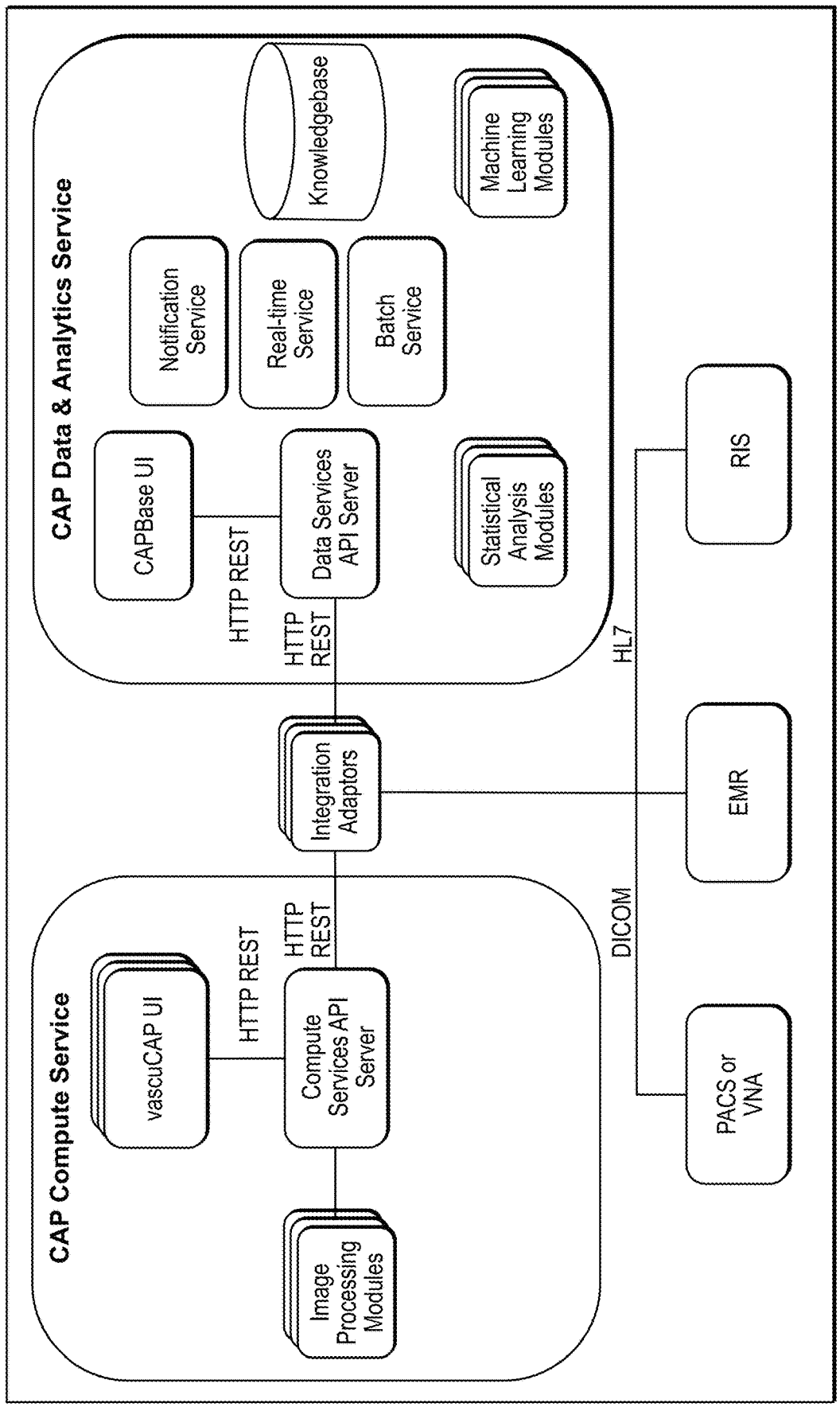
FIG. 1 is an overview schematic of the invention, comprising one or more compute services that perform various functions such as curation and processing connected by one or more integration adapter components to established healthcare IT systems and/or to one or more data services which contains the system of record database and exposes outputs in various forms including but not limited to DICOM SR, CDISC, HL7 CDA, and SPARQL endpoints.

The following detailed description presents the currently contemplated modes of carrying out the invention. The description is not to be taken in a limiting sense, but is made merely for the purpose of illustrating the general principles of the invention, since the scope of the invention is best defined by the appended claims.

In order to assist in the understanding of the disclosure, the following definitions are presented The Web Ontology Language (OWL) is a family of knowledge representation languages for authoring ontologies; where ontologies are a formal way to describe taxonomies and classification networks.

Stardog is a semantic graph database, implemented in Java, that provides support for RDF and all OWL 2 profiles providing extensive reasoning capabilities and uses SPARQL as a query language.

Qt is a cross-platform application framework that is widely used for developing application software.

In one or more embodiments, the method of these teachings includes representing an identification scheme for individual cases comprising demographics, observations, findings, and other descriptive information, characterizing targets for image analysis to the one case to support tracking of a given anatomy, suspected pathology, confirmed pathology, or medical intervention at one or more timepoints, storing access information to one or more medical images of each target at each timepoint, storing one or more levels of image-derived analysis, the image derived analysis comprising at least one of imaging features, measured quantities, phenotypic descriptions, or predictions relative to the one case, the one or more levels of image-derived analysis being obtained by: obtaining a group of medical images corresponding to the one case, calculating imaging features for the group of medical images, applying a trained method, incorporating one or more non-imaging inputs, in order to obtain quantitative properties, hereinafter referred to as analytes for the one case, and using the analytes to obtain a group of phenotypes for the one case. The method, in the one or more embodiments, also includes Providing semantic search ability to access any stored data item, individually or in sets, within or across cases, within or across Studies, within or across groups, within or across targets, for imaging or non-imaging associated data, according to concepts in an ontology according to relationships, without requiring the queries to be defined beforehand, the data store hereinafter referred to as a knowledgebase.

In one instance, the semantic search ability includes a component that traverses concepts in an ontology according to relationships, and the method of these teachings further includes applying the component that traverses concepts in an ontology according to relationships, using an imaging ontology, in order to obtain a number of Resource Description Framework (RDF) triples; the number of RDF triples hereinafter referred to as a triple store.

Image-derived information is made available by performing analyses with semantic annotations accessible using semantic web technology for personalized medicine and discovery science.

Computer-aided measurement of lesion or organ structure and quantification of tissue composition in first- or second-reader paradigms made possible by an interdisciplinary convergence between next generation computation methods for personalized diagnostics based on quantitative imaging assessment of phenotype implemented in an architecture which proactively optimizes interoperability with modern clinical IT systems provides power to the clinician as they manage their patients across the continuum of disease severity for improved patient classification across surgical, medical, and surveillance pathways. More timely and accurate assessments yield improved outcomes and more efficient use of health care resources, benefits that far outweigh the cost of the tool—at a level of granularity and sophistication closer to the complexity of the disease itself rather than holding the assumption that it can be simplified to a level which belies the underlying biology.

The method of these teachings can be applied to, for example, but not limited to, a. Create RDF triples for the local Knowledgebase.
b. Create RDF knowledge spanning [remote] domains and communities.
c. Support ontology curated knowledge.
d. Set up studies to gather imaging results.
e. Support automated data curation and scripted editing.
f. Link knowledge to multiple ontologies.
g. Establish metadata standards and define scripted runs.
h. Build composite markers and multiple parameters per modality and spanning multiple modalities.
i. Find data with high precision and recall.
j. Form and expose queries to the Knowledgebase to find data.
k. Configure knowledge resources and data services.
l. Configure data input and output services.
m. Run and modify statistical analyses.
n. Provide a toolbox of analysis scripts.
o. Configure set of analysis scripts in toolbox.
p. Support user defined output report templates.
q. Provide scripts for export and map data into output reports.
r. Connect to electronic regulatory systems.

Figure 1A:
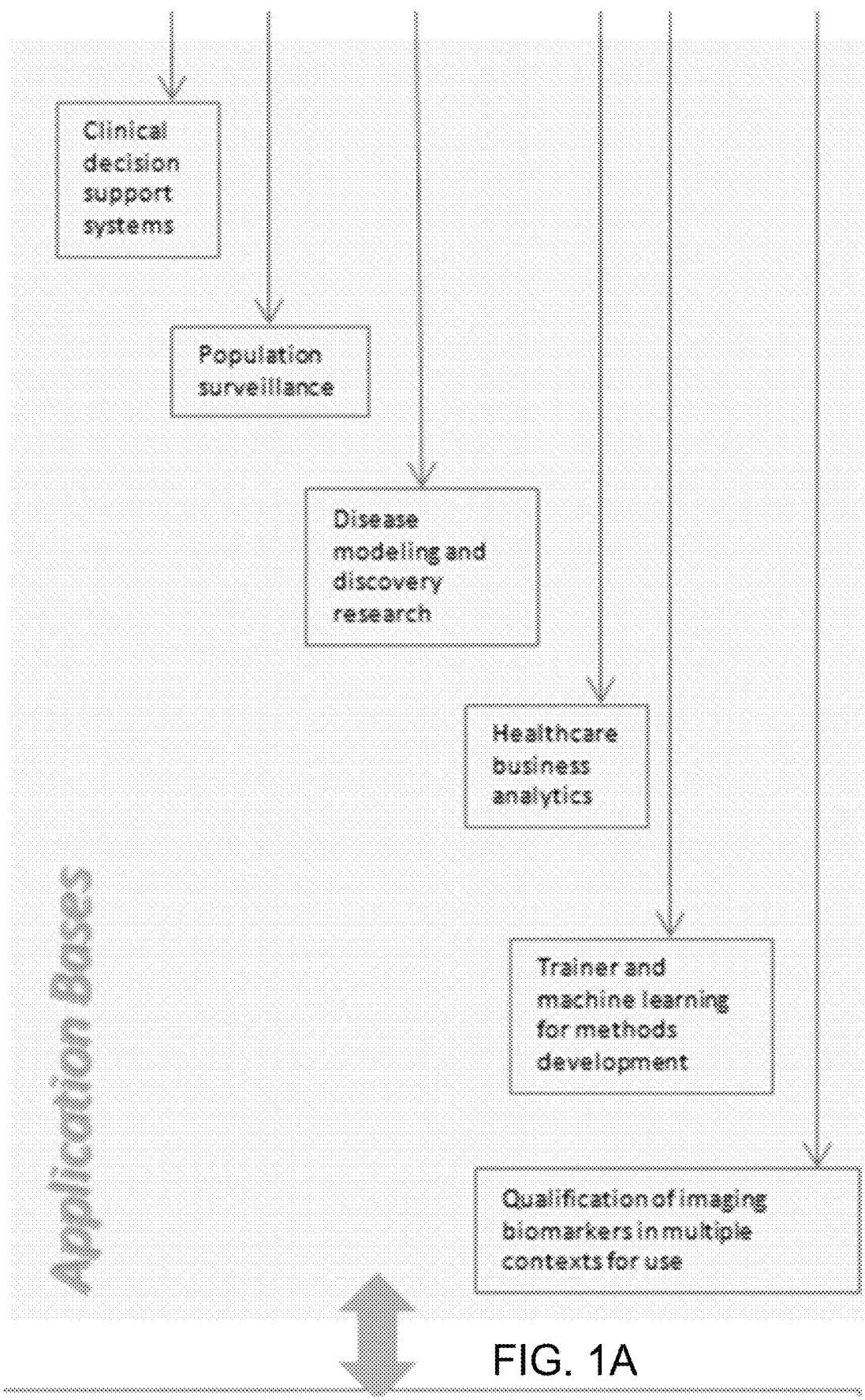
FIG. 1a shows a variety of computational applications for which the method of these teachings can be applied.

FIG. 1a shows a variety of other computational applications for which the method of these teachings can be applied.

Figure 1B:
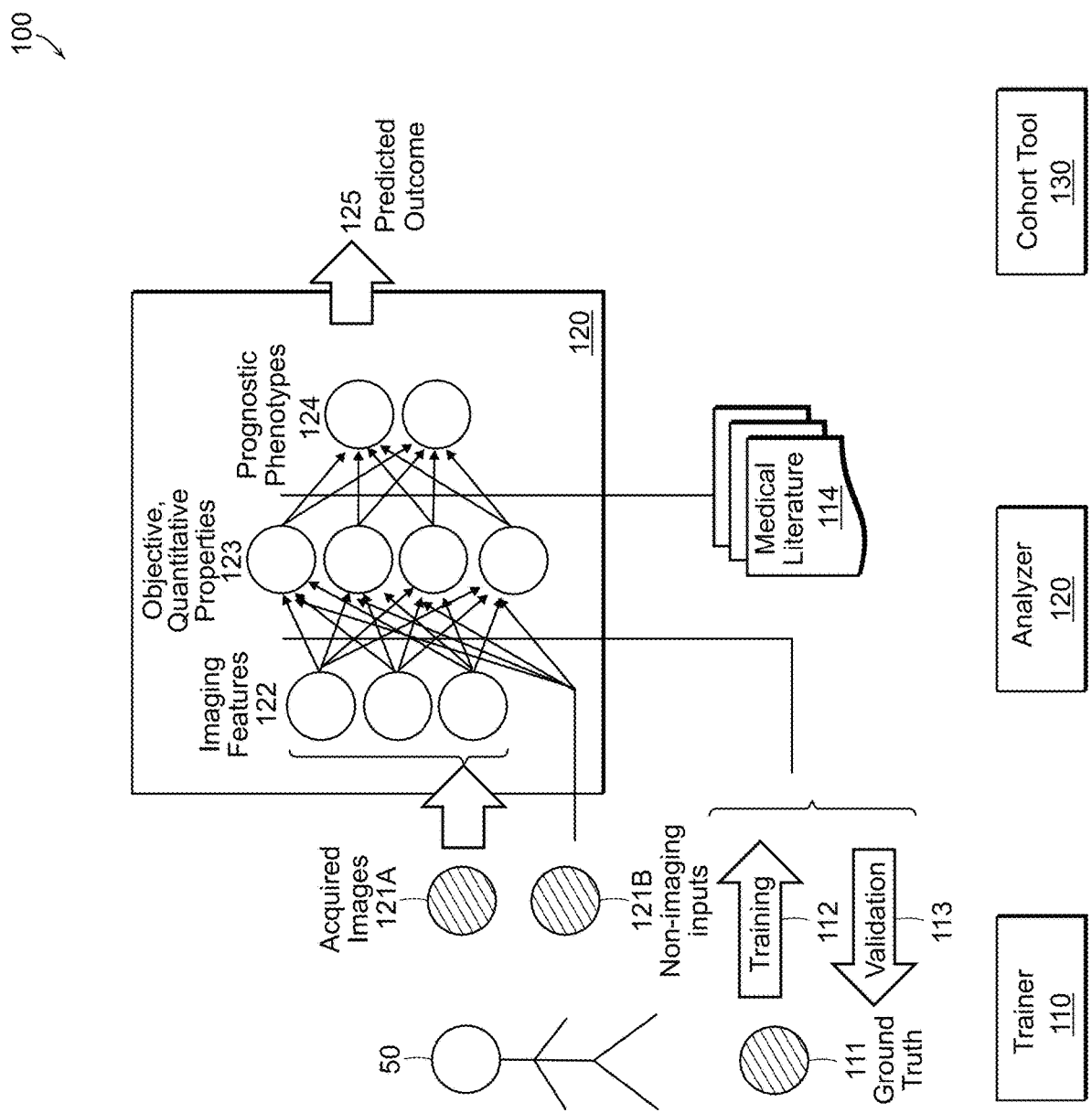
FIG. 1b is an overall schematic of an example embodiment for obtaining the one or more levels of image-derived analysis.

FIG. 1b is an overall schematic of an example embodiment for obtaining the one or more levels of image-derived analysis. With initial reference to FIG. 1b, a schematic of an exemplary system 100 is depicted. The exemplary system and exemplary embodiments are disclosed in U.S. Published patent application for U.S. patent application Ser. No. 14/959,732, which is incorporated by reference herein in its entirety and for all purposes. The exemplary embodiments are referred to as computer aided phenotyping (CAP) systems. The exemplary embodiments are herein after referred to as CAP systems or, individually as imaged target-CAP (for example, when the imaged target is a vascular tissue, the exemplary embodiment is referred to as vascuCAP. There are three basic functionalities which may be provided by the system 100 as represented by the trainer module 110, the analyzer module 120 and the cohort tool module 130. As depicted, the analyzer module 120 advantageously implements a hierarchical analytics framework which first identifies and quantifies biological properties/analytes 130 utilizing a combination of (i) imaging features 122 from one or more acquired images 121A of a patient 50 and (ii) non-imaging input data 121B for a patient 50 and then identifies and characterizes one or more pathologies (e.g., prognostic phenotypes) 124 based on the quantified biological properties/analytes 123. Advantageously, the analyzer module 120 may operate independent of ground truth or validation references by implementing one or more pre-trained, e.g., machine learned algorithms for drawing its inferences.

In example embodiments, the analyzer may include algorithms for calculating imaging features 122 from the acquired images 121A of the patient 50. Advantageously, some of the image features 122 may be computed on a per-voxel basis while others may be computed on a region-of-interest basis. Example non-imaging inputs 121B which may be utilized along with acquired images 121A may include data from laboratory systems, patient-reported symptoms, or patient history.

As noted above, the image features 122 and non-imaging inputs may be utilized by the analyzer module 120 to calculate the biological properties/analytes 123. Notably, the biological properties/analytes are typically quantitative, objective properties (e.g., objectively verifiable rather than being stated as impression or appearances) that may represent e.g., a presence and degree of a marker (such as a chemical substance) or other measurements such as structure, size, or anatomic characteristics of region of interest. In example embodiments, the quantified biological properties/analytes 123 may be displayed or exported for direct consumption by the user, e.g., by a clinician, in addition to or independent of further processing by an analyzer module which operates by calculating imaging features, some of which are computed on a per-voxel basis and others on a region-of-interest basis.

These are used along with one or more non-imaging inputs which may be drawn from laboratory systems, patient-reported symptoms, or patient history for the calculation of one or more biological analytes, noted as quantitative, objective properties. Note that the word "analyte" best fits those properties that represent presence and degree of substances but for generality, this term may also apply to other measurements such as structure, size, or anatomic characteristics. What matters is that they are objectively verifiable rather than being stated as impression or appearances. They represent that which is, not how it may or may not appear.

These properties or analytes may be displayed or exported for direct consumption by the clinician and/or they may be used in further processing steps.

One or more of these analytes may be further used as inputs to a step which determines phenotype. Phenotypes are defined in a disease-specific manner independent of imaging, often being drawn from ex vivo pathophysiological samples for which there is documented relationship to outcome expected. At this step, in one instance, RDF (or other graph database) triples are created.

The invention may further provide that outcome 125 for the user or it may not.

With reference still to FIG. 1b, the cohort tool module 130 enables defining a cohort of patients for group analyses thereof, e.g., based on a selected set of criteria related to the cohort study in question. An example cohort analysis may be for a group of patients enrolled in a clinical trial, e.g., with the patients further being grouped based on one or more arms of the trial, for example a treatment vs. control arm. Another type of cohort analysis may be for a set of subjects for which ground truth or references exist, and this type of cohort may be further decomposed into a training set or "development" set and a test or "holdout" set. Development sets may be supported so as to train 112 the algorithms and models within analyzer module 120, and holdout sets may be supported so as to evaluate/validate 113 the performance of the algorithms or models within analyzer module 120.

With continued reference to FIG. 1b, the trainer module 110 may be utilized to train 112 the algorithms and models within analyzer module 120. In particular, the trainer module 110, may rely on ground truth 111 and/or reference annotations 114 so as to derive weights or models, e.g., according to established machine learning paradigms or by informing algorithm developers. In example embodiments, classification and regression models are employed which may be highly adaptable, e.g., capable of uncovering complex relationships among the predictors and the response. However, their ability to adapt to the underlying structure within the existing data can enable the models to find patterns that are not reproducible for another sample of subjects. Adapting to irreproducible structures within the existing data is commonly known as model over-fitting. To avoid building an over-fit model, a systematic approach may be applied that prevents a model from finding spurious structure and enable the end-user to have confidence that the final model will predict new samples with a similar degree of accuracy on the set of data for which the model was evaluated.

The primary function is to represent various imaging-derived information. In one embodiment, examples of these data, further disclosed in U.S. Published patent application for U.S. patent application Ser. No. 14/959,732, include the following features.

Anatomic Structure: Structural measurements have long been and remain the single most used measurements in patient care. The category is broad and the measurements are of objects of varying sizes, so generalizations should be made with care. A primary consideration is the limit of spatial sampling or resolution. The minimally detectable changes may, however, be lower than the spatial sampling by taking advantage of subtle variations in intensity levels due to partial volume effect. Additionally, stated resolutions generally refer to grid size and field of view of post-acquisition reconstructions rather than the actual resolving power of the imaging protocol, which determines the minimum feature size that can be resolved. Likewise, in-plane vs. through-plane resolutions may or may not be the same and not only the size of a given feature but as well its proportions and shape will drive the measurement accuracy. Last but not least, in some cases categorical conclusions are drawn from applying thresholds to the measurements, which may then be interpreted according to signal detection theory with the ability to optimize the trade-off between sensitivity and specificity, terms that don't otherwise refer to measurements in the normal sense.

Tissue Characteristics: The quantitative assessment of the individual constituent tissue components, by way of example for atherosclerotic plaques including lipid rich necrotic core (LRNC), fibrosis, intraplaque hemorrhage, permeability, and calcification, can provide crucial information concerning the relative structural integrity of the plaque that could aid the physician's decisions on course of medical or surgical therapy. From the imaging technology point of view, the ability to do this lies less with spatial resolution as with contrast resolution and tissue discrimination made possible by differing tissues responding to incident energy differently so as to produce a differing receive signal. Each imaging modality does this to some extent; terms in ultrasound such as "echolucency", the CT number in Hounsfield Units, and differentiated MR intensities as a function of various sequences such as (but not limited to) T1, T2 and T2*.

Dynamic tissue behavior (e.g., Permeability): In addition to morphological features, there is increasing recognition that dynamic features are valuable quantitative indicators of pathology. Dynamic sequences where the acquisition is taken at multiple closely-spaced times (known as phases) expand the repertoire beyond spatially-resolved values t include temporally-resolved values which may be used for compartment modeling or other techniques to determine the tissues' dynamic response to stimulus (such as but not limited to wash-in and wash-out of contrast agent). Through the use of dynamic contrast enhanced imaging with ultrasound or MR (e.g., in the carotid arteries or delayed contrast enhancement (e.g., in the coronary arteries), sensitive assessments of the relative permeability (e.g., $K^{trans}$ and $V_p$ parameters from kinetic analysis) of the microvascular networks of neoangiogenesis within the tissues of interest can be determined. In addition, these dynamic series can also aid in the differentiation between increased permeability versus other compartment modeling scenarios, e.g., intraplaque hemorrhage.

Hemodynamics: The basic hemodynamic parameters of the circulation have a direct effect on many pathologies. Blood pressures, blood flow velocity, fractional flow reserve (FFR) and vessel wall shear stress may be measured by techniques ranging from very simple oscillometry to sophisticated imaging analysis. Using common principles of fluid dynamics, calculations of shear stress can be ascertained for different regions. In addition, the effects of antihypertensive drugs on hemodynamics have been followed for short and long-term studies.

Figure 6:
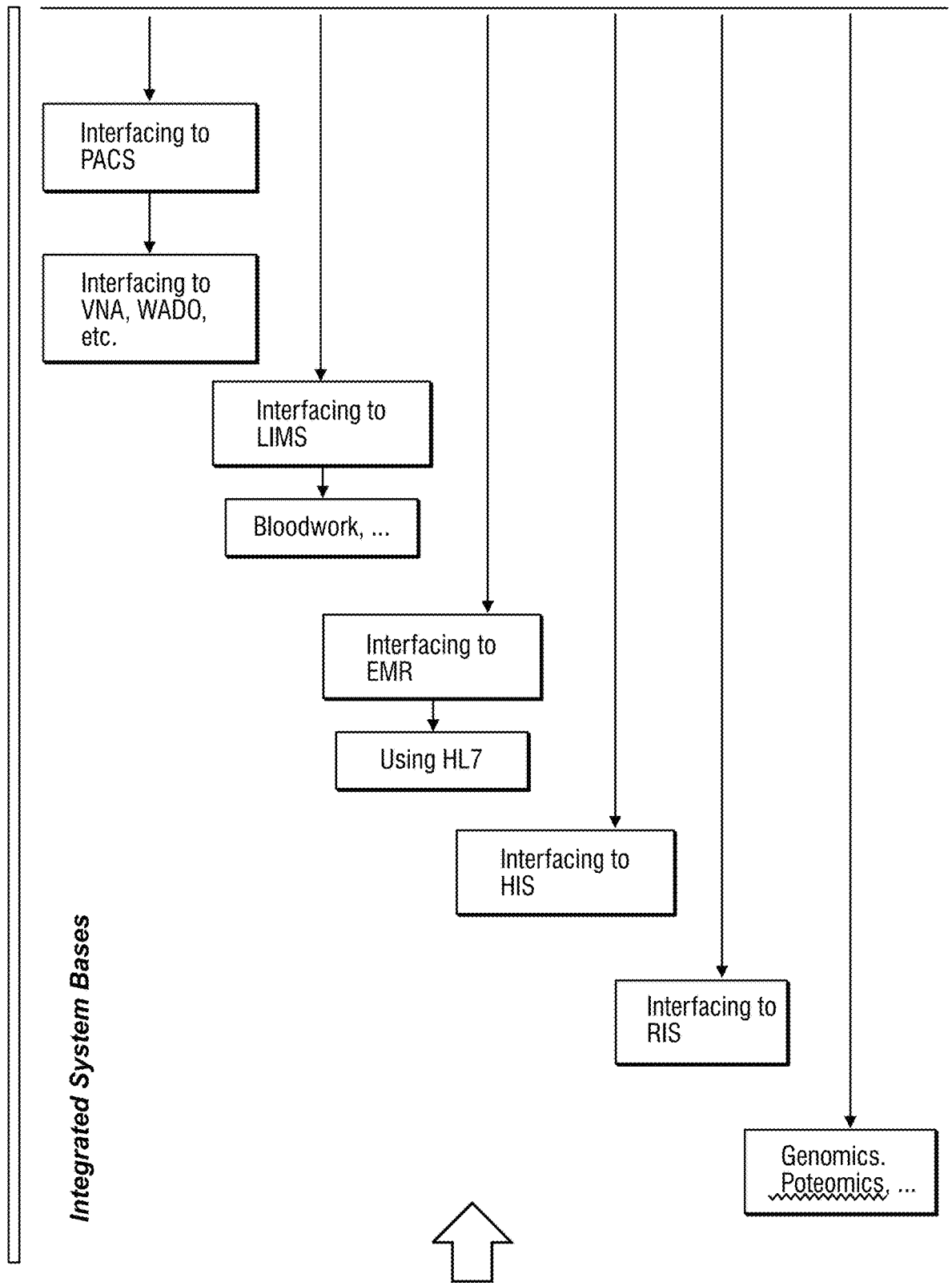
FIG. 6 shows interfaces of the method and system of these teachings to existing medical information structures.

The method and system of these teachings interfaces with existing medical information systems. Examples of such interfaces are shown in FIG. 6.

The exemplary applications detail herein below are provided in order to further elucidate these teachings. It should be noted that these teachings are not limited only to those exemplary applications.

Figure 1C:
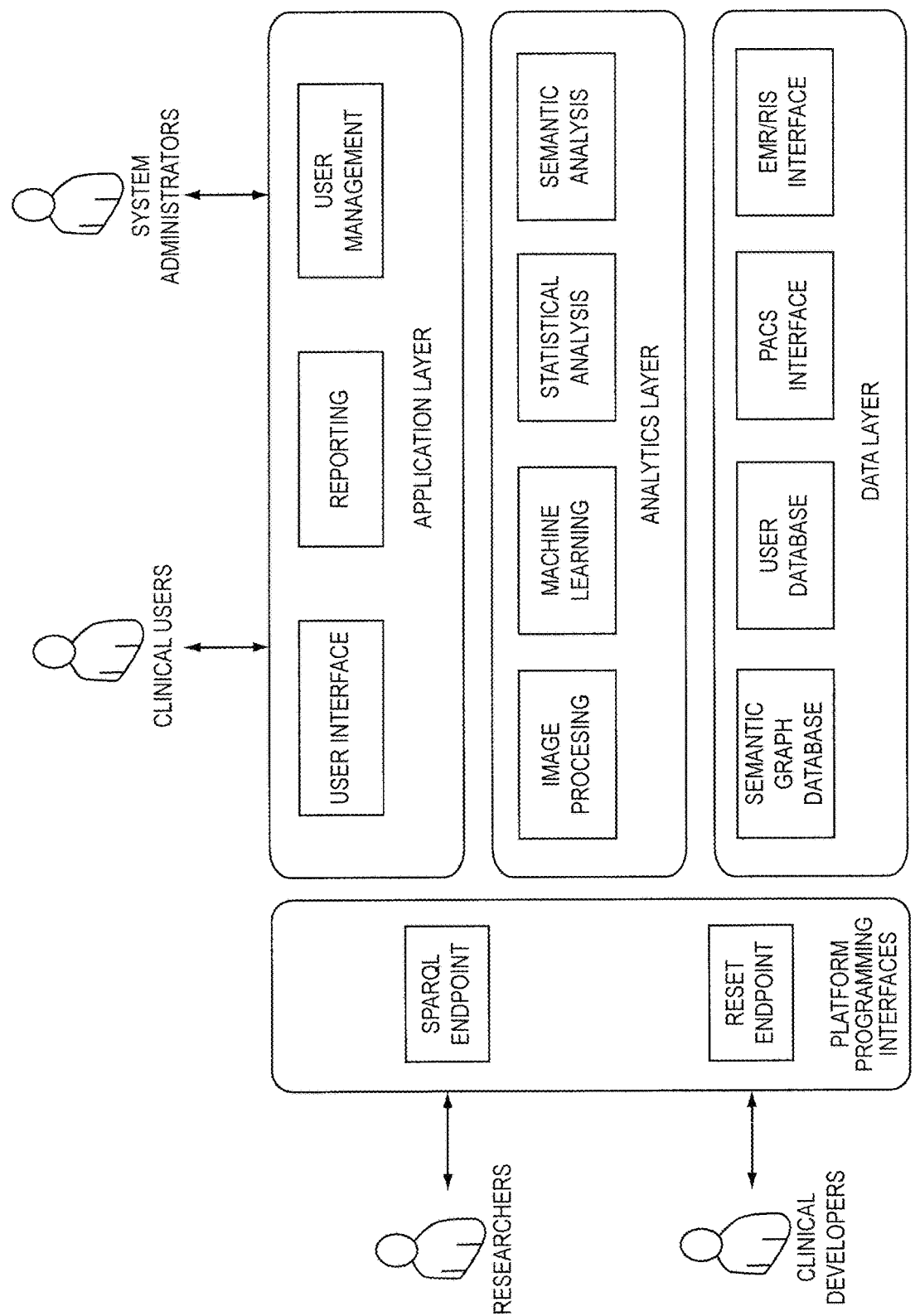
FIG. 1c shows an overall schematic of an example framework that allows efficient development of image-derived analysis tools while also setting up access to functionality needed for more complete statistical evaluation of performance and representation of results in a semantically-expressive knowledge representation.

A framework that allows efficient development of image-derived analysis tools while also setting up access to functionality needed for more complete statistical evaluation of performance and representation of results in a semantically-expressive knowledge representation is shown in FIG. 1c.

The central data stored are represented in the Knowledge Base, which follows a "blackboard" design pattern and is, in one embodiment, implemented as an RDF Triple Store. The data organization of this embodiment flows from the hierarchy of requirements and specifies three primary types of database assets. The Clinical user products deploy an RDF triplestore, implemented by a data unification platform leveraging smart graph technology, for example, Stardog, and which may be deployed as "localhost" or on another server, and used to store triples representing quantitative results data. The Research user product augments the triplestore with metadata used for determining the similarity of the patient case with similar cases drawn from a cohort with imported data from systems which provide portals made available to collaborators for the collection of source study data. In other embodiments, the "blackboard" design pattern is implemented in a draft database or in a relational database.

Figure 1D:
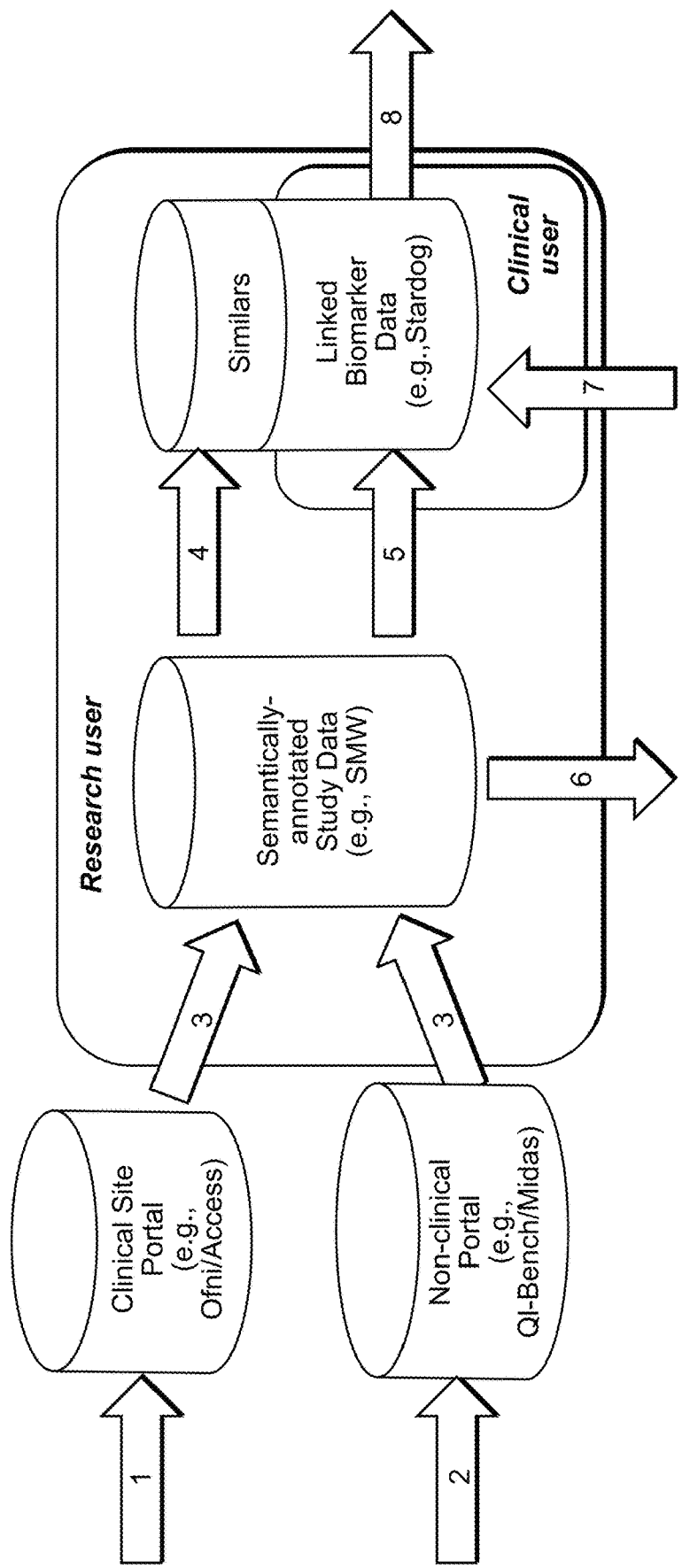
FIG. 1d shows the central data abstractions including various views and representations of data, sometimes referred collectively or in parts to the "blackboard", or Biomarker Knowledge Base.

FIG. 1d shows the central data abstraction referred to as the "blackboard", also known as the Biomarker Knowledge Base.

Legend for FIG. 1d:
1. Input data according to clinical trial or study protocols
2. Input data according to research study designs
3. Import
4. Meta-data facilitating use cases for database of similar
5. Meta-data facilitating linking of case data
6. Meta-data facilitating analysis of cases in reference data sets (intended to be symmetric with what would be available for clinical cases augmented with extensions for research)
7. Quantitative readings for individual case
8. Export data for individual case (and/or free-form query for research use)

In one embodiment, the knowledgebase is implemented as an RDF Triple Store. It links data across the data services using handles or universal resource identifiers (URIs).

Figure 1E:
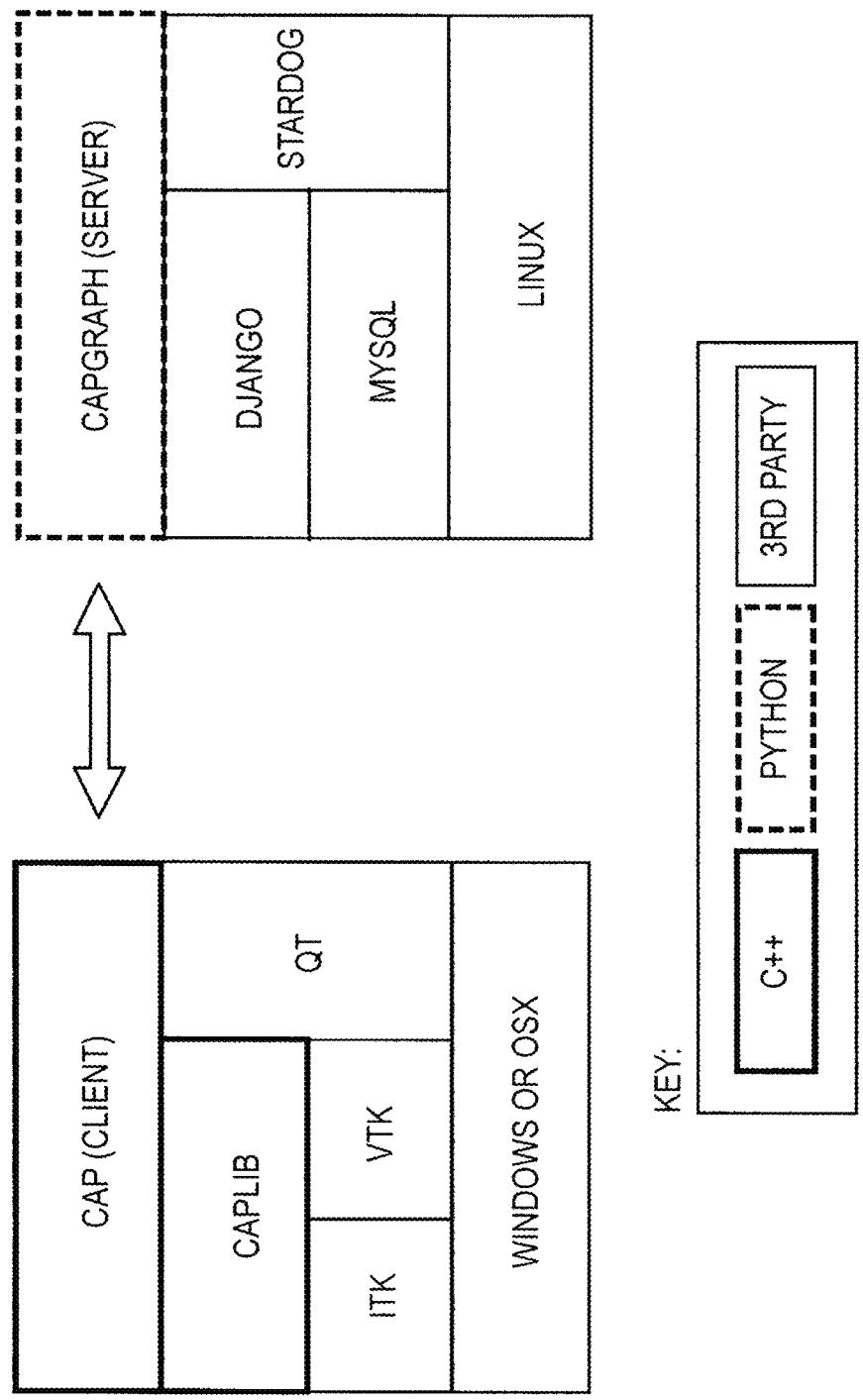
FIG. 1e shows an overall schematic of an example embodiment for how data services are interfaced and implemented through a client-server model in example layers.

FIG. 1e shows how data services are interfaced through and implemented through a client-server model in example layers.

In order to further elucidate these teachings, an exemplary embodiment of the semantic search ability and its use are presented herein below. It should be noted that these teachings are not limited to only this exemplary embodiment.

In one instance, we map proprietary or local classes to public domain classes, for example, to SNOMED-CT, ICD, HL7 classes, but in general to a heterogeneous set where definitions may be in common but structured and named differently. To perform the mappings we assert triples use, for example, owl:sameAs predicates.

Figure 7:
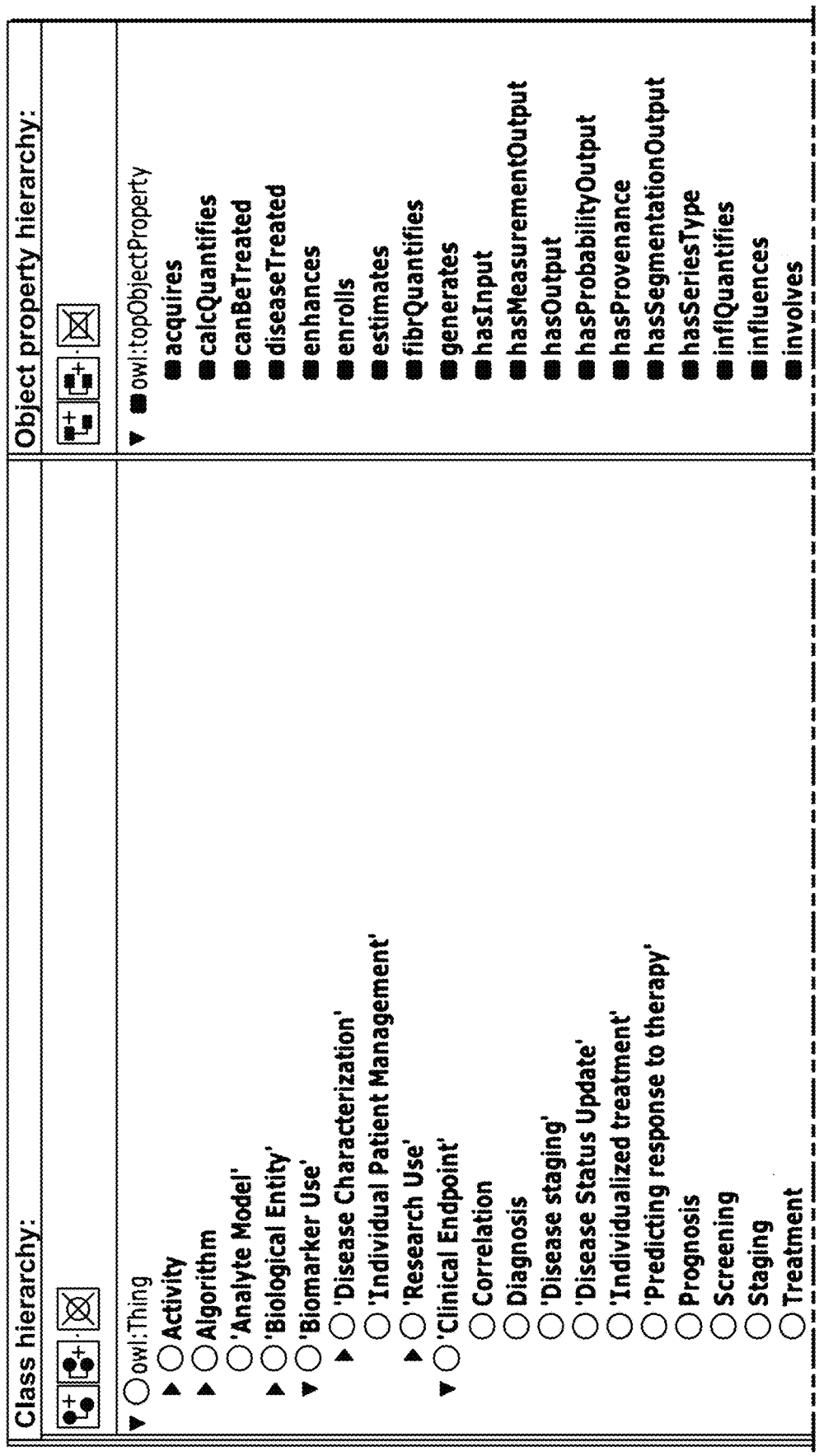
FIG. 7 shows an exemplary ontology that may be used to tie quantitative imaging measurements to health conditions and disease processes as well as represent their technical and clinical performance together; The left panel is a class hierarchy and the right panel are properties that define relationships between the classes.
Figure 7:
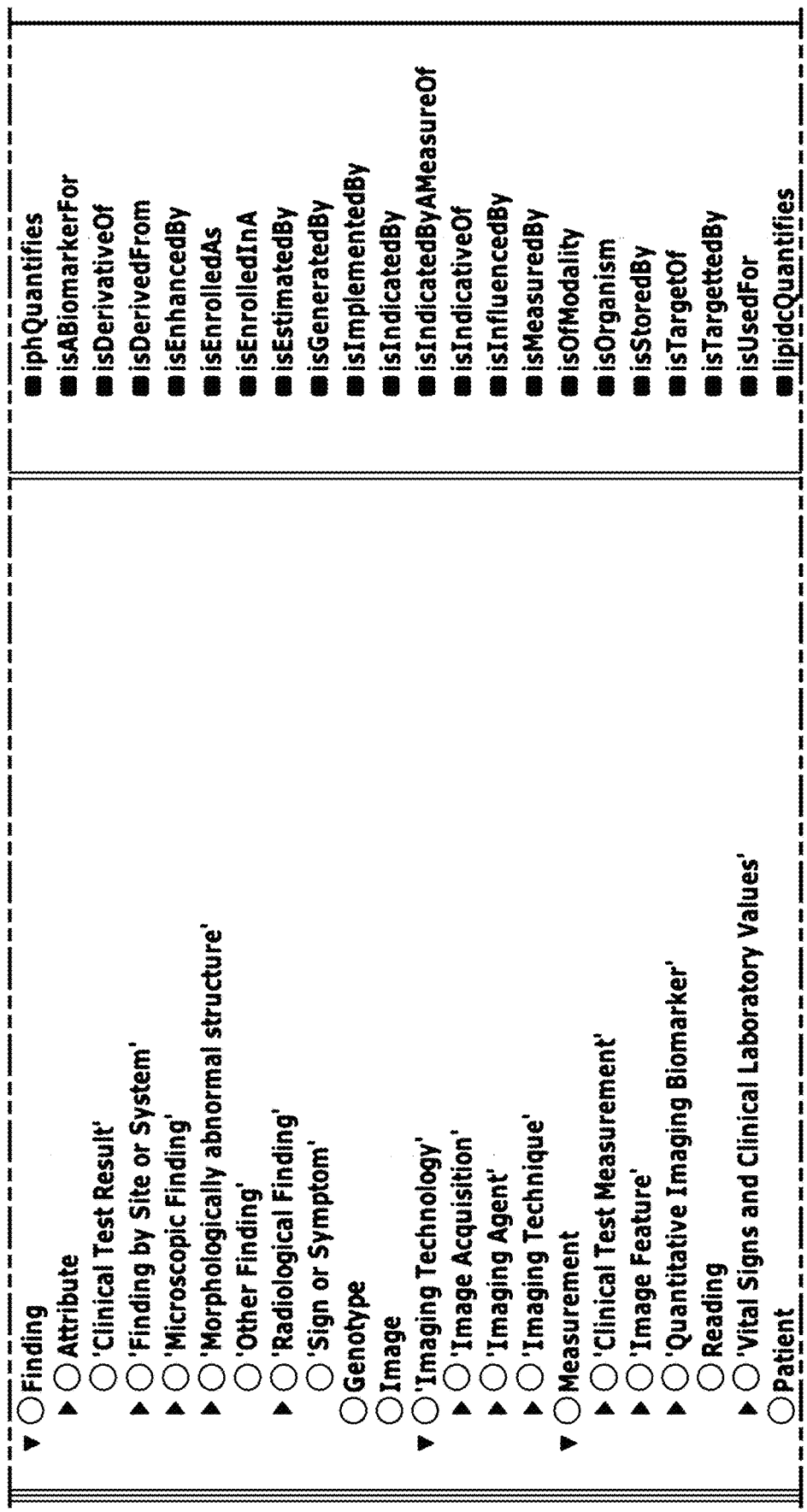
Figure 7:
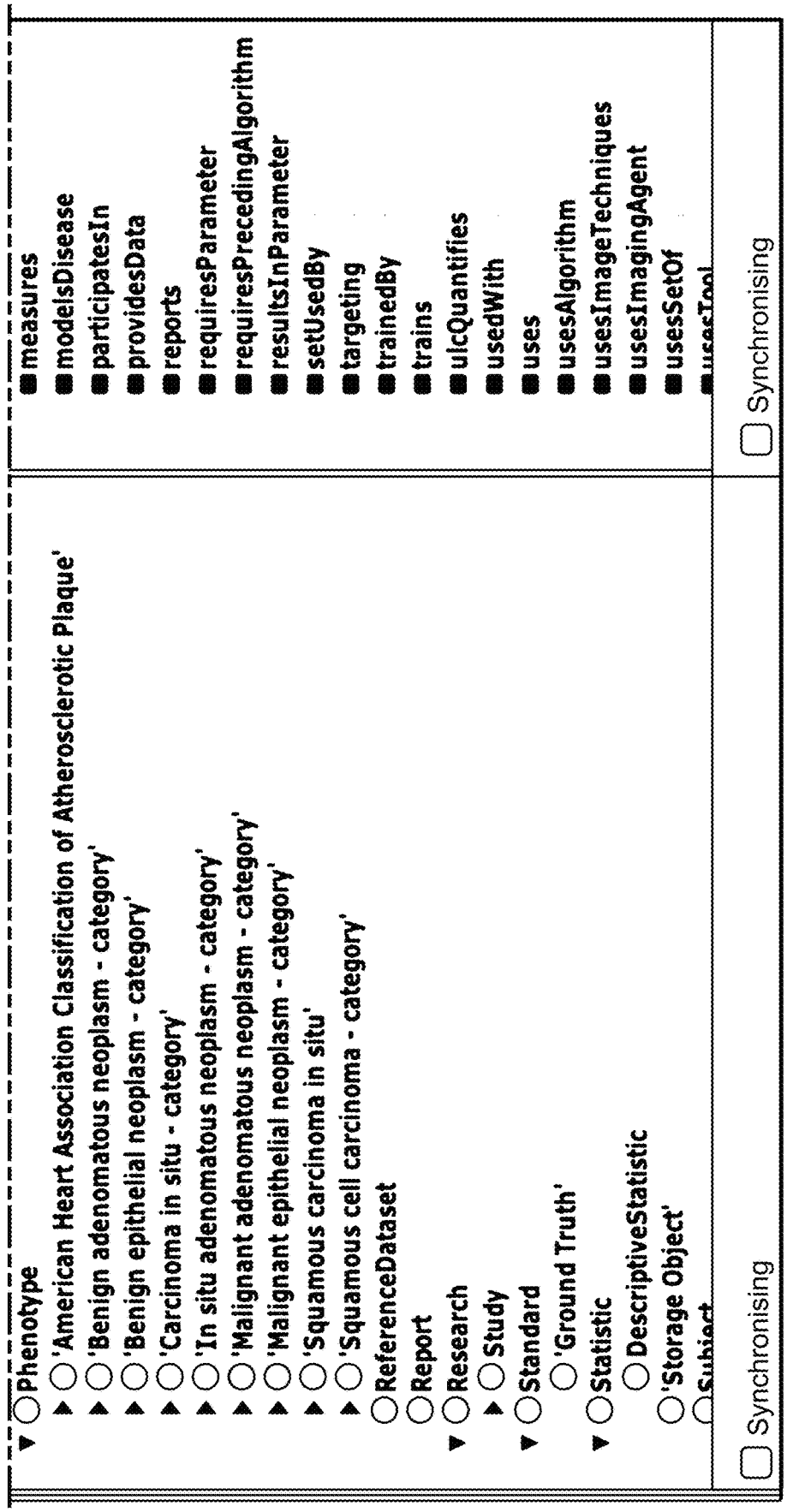

The mappings may be placed in the same graph or distributed across separate named graphs for each ontology which may be optimized with respect to the overhead of inference being scoped in such a way that a given query or operation is scoped to specific graphs rather than always being all graphs. The semantic search ability includes a component that traverses concepts in an ontology such as given in FIG. 7 according to relationships, and the method of these teachings further includes applying the component that traverses concepts in an ontology according to relationships, using an imaging ontology, in order to obtain a number of Resource Description Framework (RDF) triples; the number of RDF triples hereinafter referred to as a triple store.

In one embodiment of the above instance, the method also includes accessing predetermined data services, generating queries from the plurality of RDF triples in order to collect data sets, and using the queries and the predetermined data services to collect data sets.

Figure 1F:
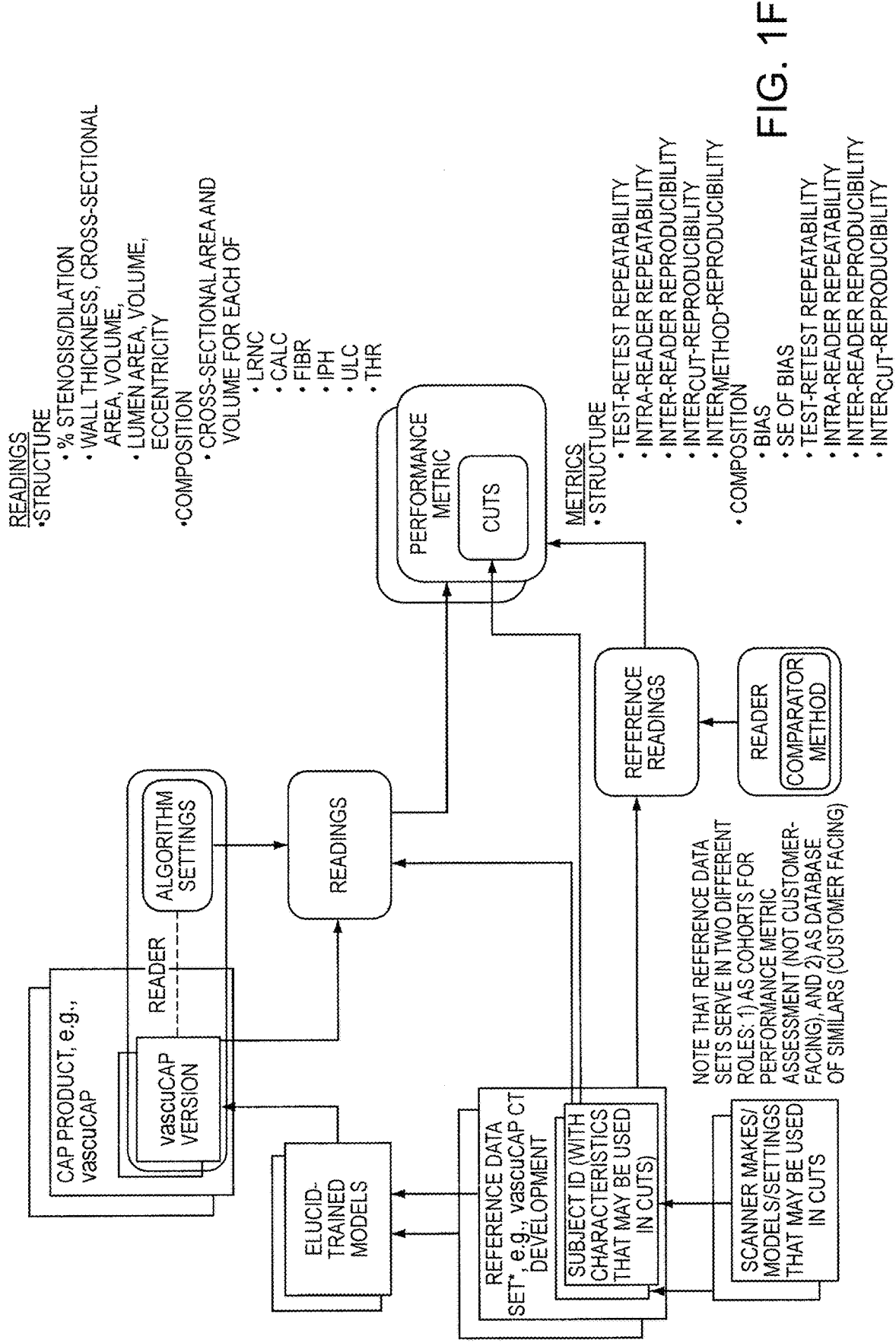
FIG. 1f shows an information flow schematic for the use of exemplary embodiments of components of these teachings in applications.

Another exemplary instance is depicted in FIG. 1f which shows an information flow schematic organized using four layers as depicted in FIG. 1c. Three of those layers provide high-level to low-level functionality. The functionality layers from highest to lowest are; Application, Analytics, and Data. Clinical Users and System Administrators interact with features in the Application layer. Components in the Application layer interact with the Analytics layer. Components in the Analytics layer interact with the Data layer. The fourth layer, shown vertically, represents programming interfaces used by Researchers and Clinical Developers. Those interfaces provide programmatic access to the three vertical layers. Stakeholders of this view include System Developers, System Administrators, Clinical Users, Support Technicians, with Scalability, Performance, Interoperability, Extensibility concerns.

In another exemplary instance, the invention can be deployed in two main configurations; on-premises, or remote server. The on-premises deployment configuration has two sub-configurations; desktop only or rackmount. In the remote configuration, vascuCAP is deployed on a HIPAA compliant data center. Clients access that API server over a secure HTTP connection. Clients can be desktop or tablet browsers. No hardware except for the computers running the web browsers is deployed on the customer site. The deployed server may be on a public cloud or an extension of the customer's private network using a VPN. Stakeholders of this view include System Administrators, Support Technicians, which have Interoperability, Security, Failover & Disaster Recovery, Regulatory concerns.

In another exemplary instance, these teachings comprise a client and a server. The client is a C++ application and the server is a Python application. These components interact using HTML 5.0, CSS 5.0 and JavaScript. Wherever possible open standards may be used for interfaces including but not limited to; HTTP(S), REST, DICOM, SPARQL, and JSON. $3^{rd}$ party libraries are also used as depicted in FIG. 1e which shows the primary pieces of the technology stack.

The remainder of this disclosure is organized as a progression of functionality enabled and implemented by the present invention:

I. Individual patients may be evaluated at a given encounter or timepoint using quantitative methods, documenting not only the direct results but as well the provenance of data used to derive those results.

II. Said patients may be further evaluated at multiple encounters which may be different timepoints or repetitions at a given timepoint.

III. Groups or cohorts of patients may be evaluated at either or both of the above levels.

IV. Given one or more cohorts evaluated under similar or differing conditions, various levels of statistical analysis may be performed, for example technical or analytical performance of the measures, which may be performed for its own sake and/or to further annotate the quantitative analysis.

V. Given the measures and accompanying analytical performance of the measures and clinical and patient data, diagnostic, prognostic, with statistical analysis of the clinical efficacy established.

VI. Likewise, phenotypic information may be derived using predictive models.

VII. Given the clinical efficacy of said measures based on said patient's complementary data, further analysis involving inference to establish the strength of surrogacy of proximal markers relative to relative to distal endpoints and/or other measures of the clinical utility of applying said markers in practice may be evaluated.

Each is presented below.

Individual Patient Evaluation at a Given Encounter

In another exemplary instance, client software is implemented as an application using Qt GUI primitives. It operates according to the following flow:

1) The User creates a Workitem by loading DICOM Study and Patient Information using Workitem Generation screen
   a) Alternatively, the user can view or search for workitems using Workitem View screen
2) The User selects/edits image series to identify the target(s) for analysis
3) The User identifies the target(s) for analysis, setting proximal and distal path points
4) The User accepts the target definition, causing Structure and Composition calculations
5) The User can edit/modify various settings to conclude on the calculation values they deem most appropriate for the case
6) The User may select image snapshots for insertion into the report
7) The User reviews then accepts the report.
   a) Alternatively, the user can export the Report It is decomposed into the following packages:
Primary Application Control
Work Item Package
Series Survey Package
Target Definition Package
Patient Analyze Package
Patient Reporting Package Primary Application Control establishes framework for concurrent, multi-patient, analysis and reporting sessions using one or more of the following classes:
   class sessionItem
   class sessionItem to provide a data structure for recording analyses within the session. class StatusWatcher
   class StatusWatcher to echo stdout and a processed version of stderr to the status bar (in addition to being written to the log files). class cap
   class cap provides support for concurrent analysis session items.
   class capTools class capTools provides common basis for tool bars as exist across modules.

Figure 1G:
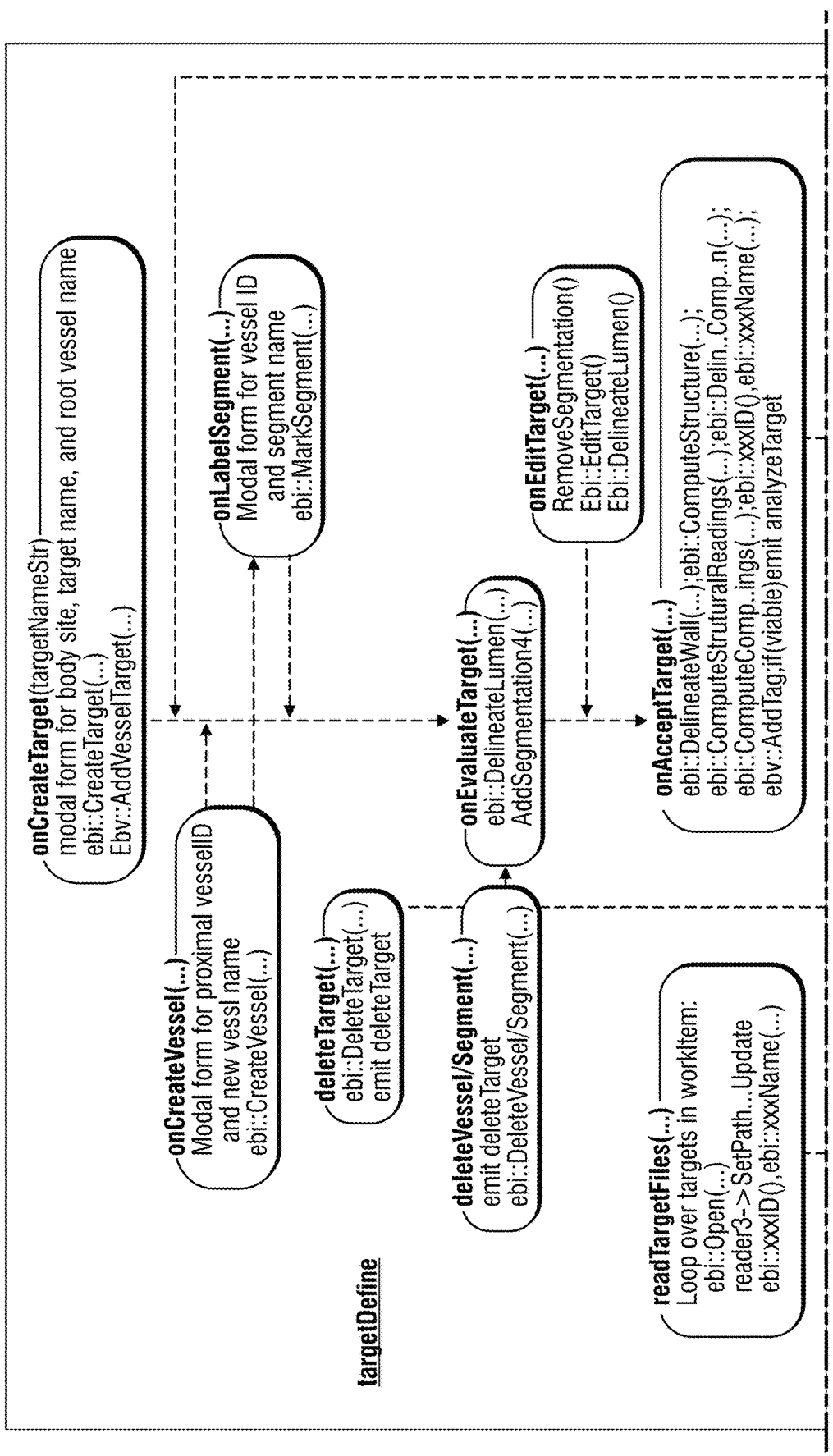
FIG. 1g shows primary methods used by a client component in one embodiment of these teachings.
Figure 1G:
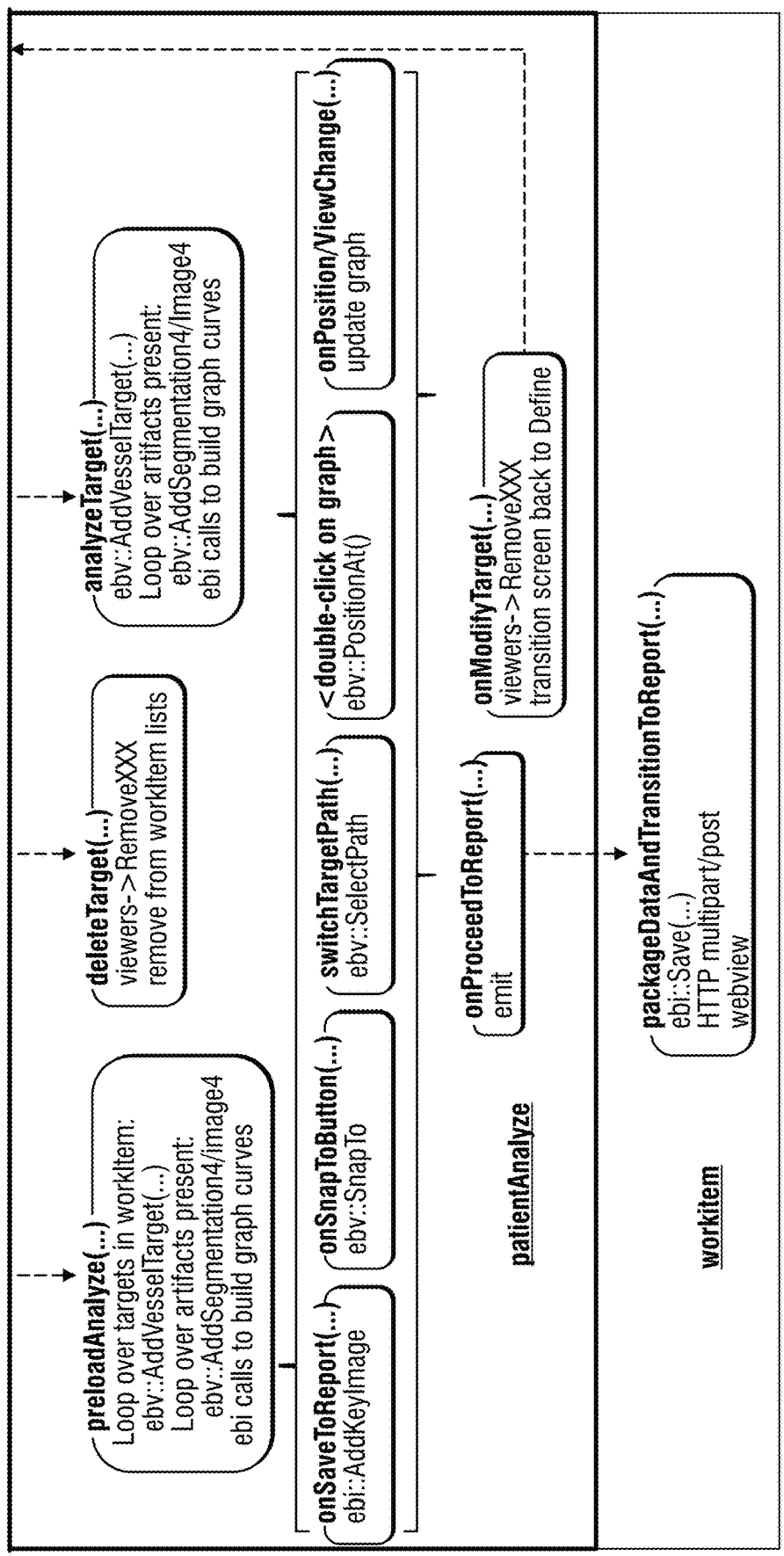
Figure 2:
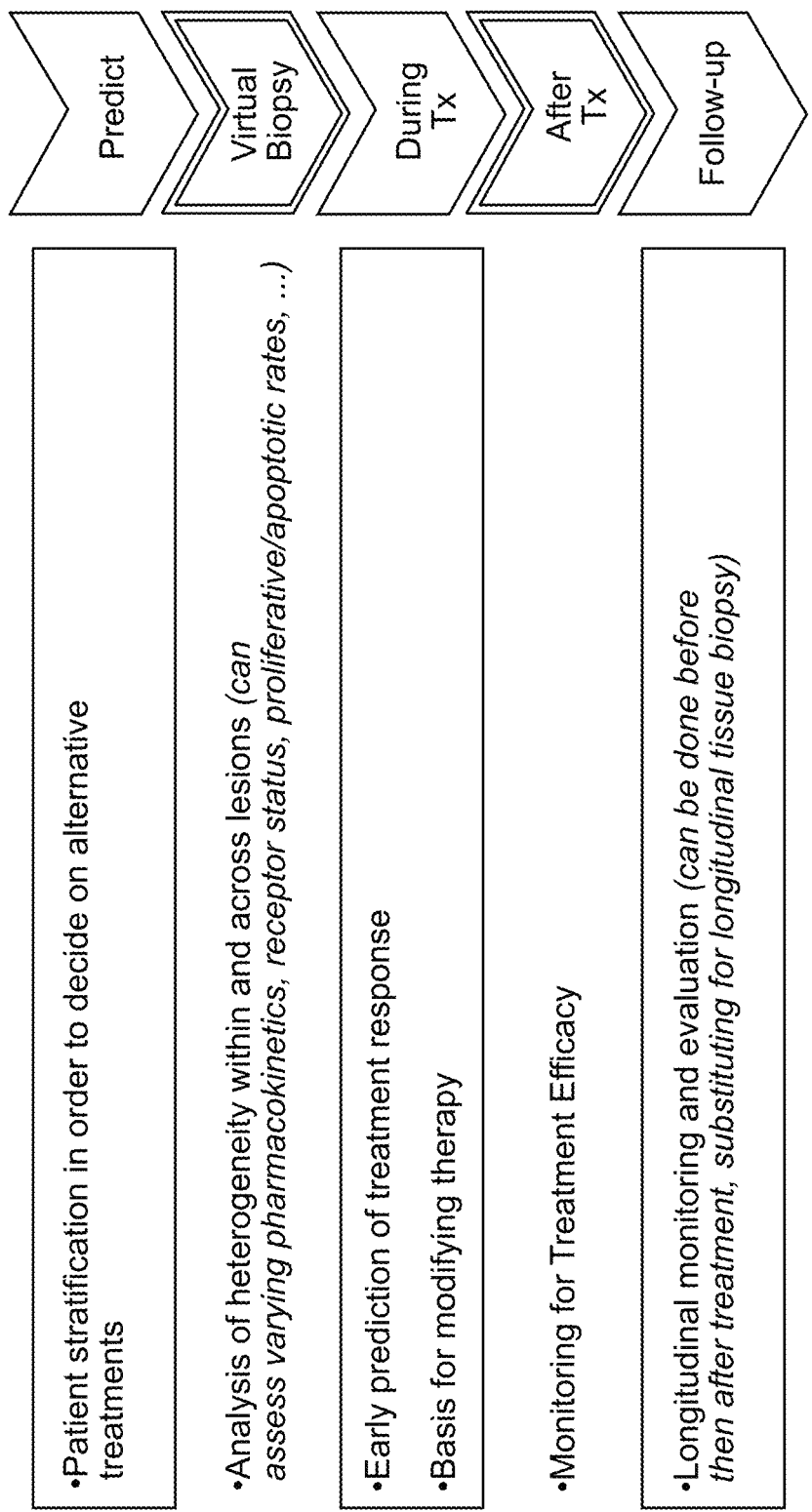
FIG. 2 summarizes functions supported by the invention for individual patient care. Imaging is increasingly used at all stages in the cycle of care for individual patients including applications that can predict the effectiveness of interventions based on patient-specific measurements, guide selection and administration of therapy, and monitor for utility and recurrence in follow-up protocols.
Figure 3:
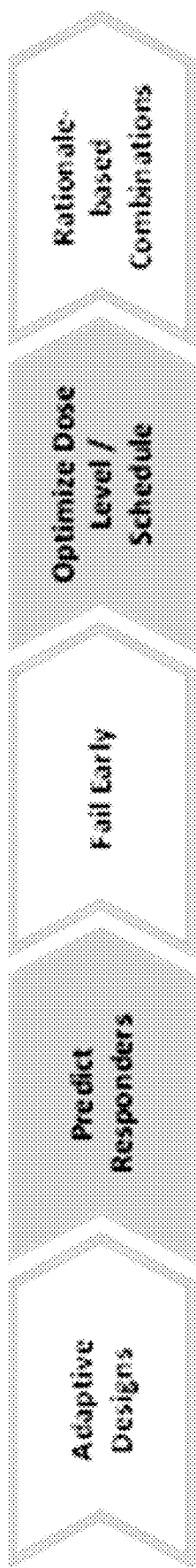
FIG. 3 summarizes functions supported by the invention for drug development. Applications of imaging in clinical trials and therapeutic development supports activities on the critical path of development and enable novel approaches that can be used to accelerate development programs and/or positively impact the effectiveness and financial performance of sponsor programs.
Figure 4:
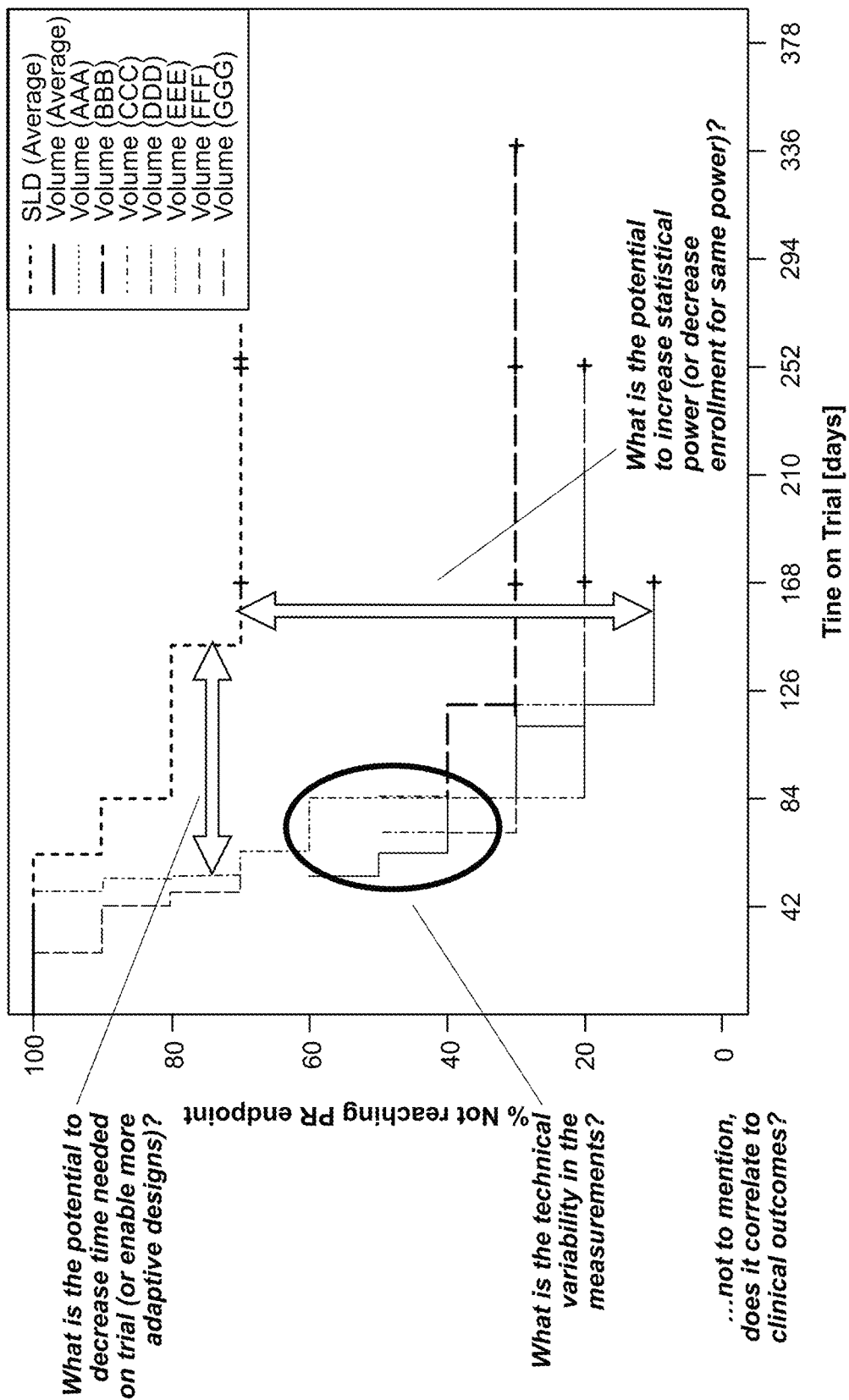
FIG. 4 illustrates key questions the informatics services would address for putative biomarkers and tests that measure them.
Figure 5:
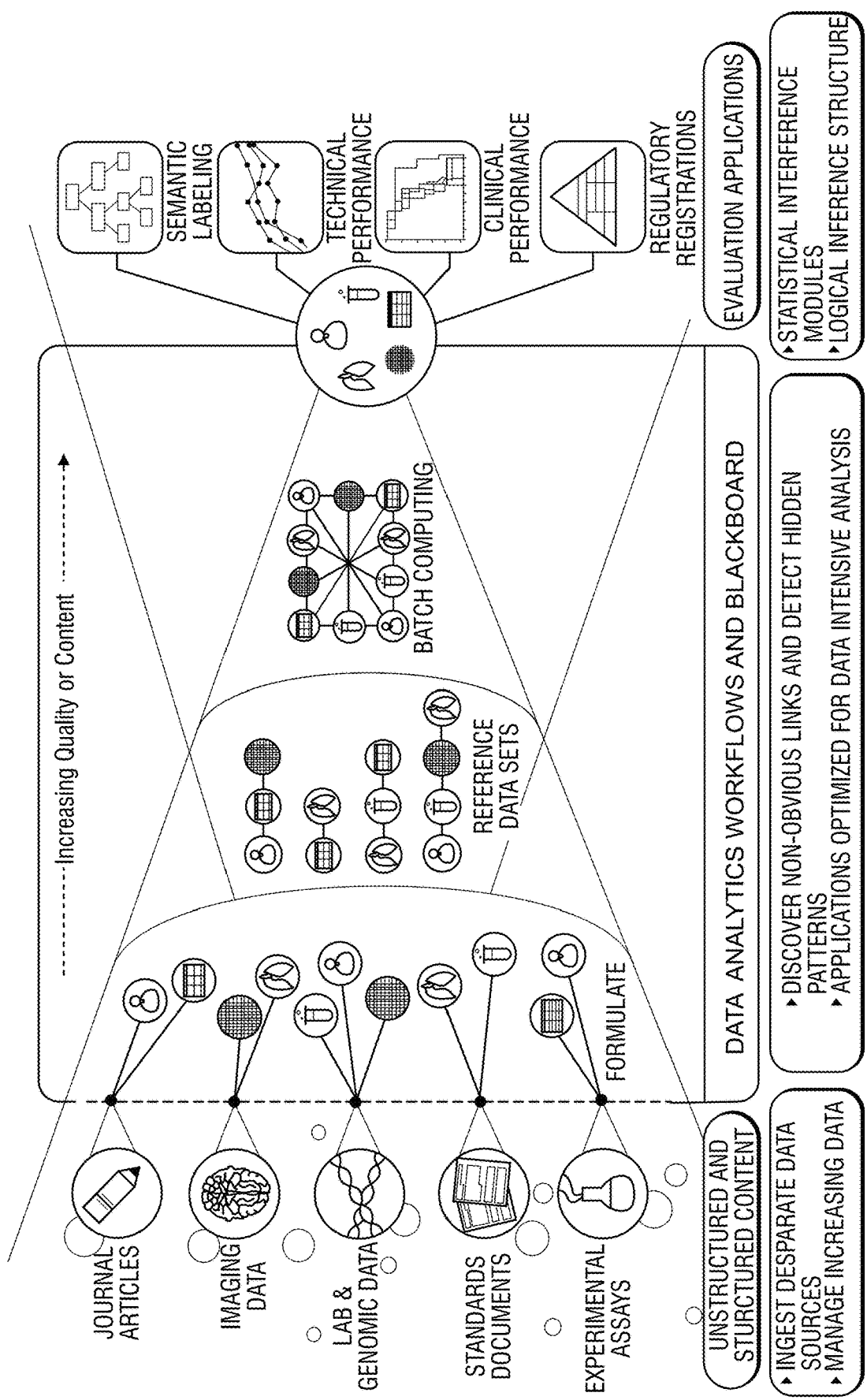
FIG. 5 is an overview schematic of the functions supported by the invention for biological research and/or methods validation, showing the heterogeneous inputs, curated reference data sets, high-throughput batch computing, and some of the outputs supported by the inventions query and inference capabilities.

Referring to FIG. 1g, a Work Item Package supports abstractions for work items, as containers for artifacts pertaining to patient analyses, and lists of them using one or more of the following classes:
   class workItemListProvenance to provide methods for the provenance of the workItem list as a whole.
   class workItemListEntry the work-horse class for each work item. class workItem
   class workItem the main class with the list as a whole and the methods to display and interact with it.
   class workItemListViewingModel a support class which implements the abstract model that serves as the basis for the actual list display.

A Series Survey Package may provide functionality associated with importing, reviewing, specification, and switching across sets of image series processed within a work item using one or more of the following classes:
   class imageSeries represents the various aspects of each individual image series
   class seriesSurvey (in namepace Ui) (subclassed from QWidget): the main class with the series set as a whole and the methods to display and interact with it. Manages the screen elements associated with the set of image series associated with a given workItem analysis.
   class UpdateSeriesInBackground provides means for background loading Referring to FIG. 1g, a Target Definition Package may provide functionality associated with defining, importing, reviewing, specification, and switching across analysis targets processed within a work item using one or more of the following classes:
   class stageParameters provides functionality for user review and selection of processing parameters associated with analysis of targets
   class processingParameters provides functionality for user review and selection of processing parameters associated with analysis of targets class probabilityMap represents analyte probability maps
class region represents individual target regions
class valueMap represents individual value maps, for example, wall thickness class targetDef
class targetDef represents individual targets, providing all definition needed for computation and display
class targetDefine (in namepace Ui) (subclassed from QWidget): the main class with the list of definitions as a whole and the methods to access and interact with it. Responsible for all screen management associated with targets, including creation, definition, etc.

Referring to FIG. 1g, a Patient Analyze Package may serve as a central point of user activity to analyze a patient at a given timepoint using one or more of the following classes:
class readingsSelector
class readingsSelector provides functionality for user selection and specification for readings associated with analysis of targets
class patientAnalyze (in namepace Ui) (subclassed from QWidget): the main class with the list of definitions as a whole and the methods to access and interact with it. Manages all computation and display aspects analyses comprising multiple targets and multiple image series for a given workItem session.

Further, a Patient Reporting Package may allow users to compose and prepare of analysis result exports and reports using one or more of the following classes:
class workItemUpdate implementing updates, which are placed on a list of updates for each workItemListEntry for reference during the reporting activity.
class patientReport (in namepace Ui) (subclassed from QWidget): the main class with the list of definitions as a whole and the methods to access and interact with it. Supports functionality to transfer appropriate data and interact with server for reporting functions.

In another exemplary instance, server software is implemented comprised of the following components:
A user-visible application, which utilizes an internal RDBMS mysql,
An interface to a graph database (stardog), further comprising:
A representation of named classes and their hierarchy with properties defined for them
Translation code from application code to SPARQL queries
Code to make the SPARQL query endpoints visible to privileged users
A series of utility scripts which may be run on demand or in batch to process data relationships
Server routing
Stylesheets
View templates To meet HIPAA compliance requirements, the following allocation between encrypted vs. non-encrypted databases is described below. In general, "core identifiers" are stored and accessed with encryption in, for example, mysql, with "detailed" but non-identifiable information stored in, for example, Stardog.

Figure 8:
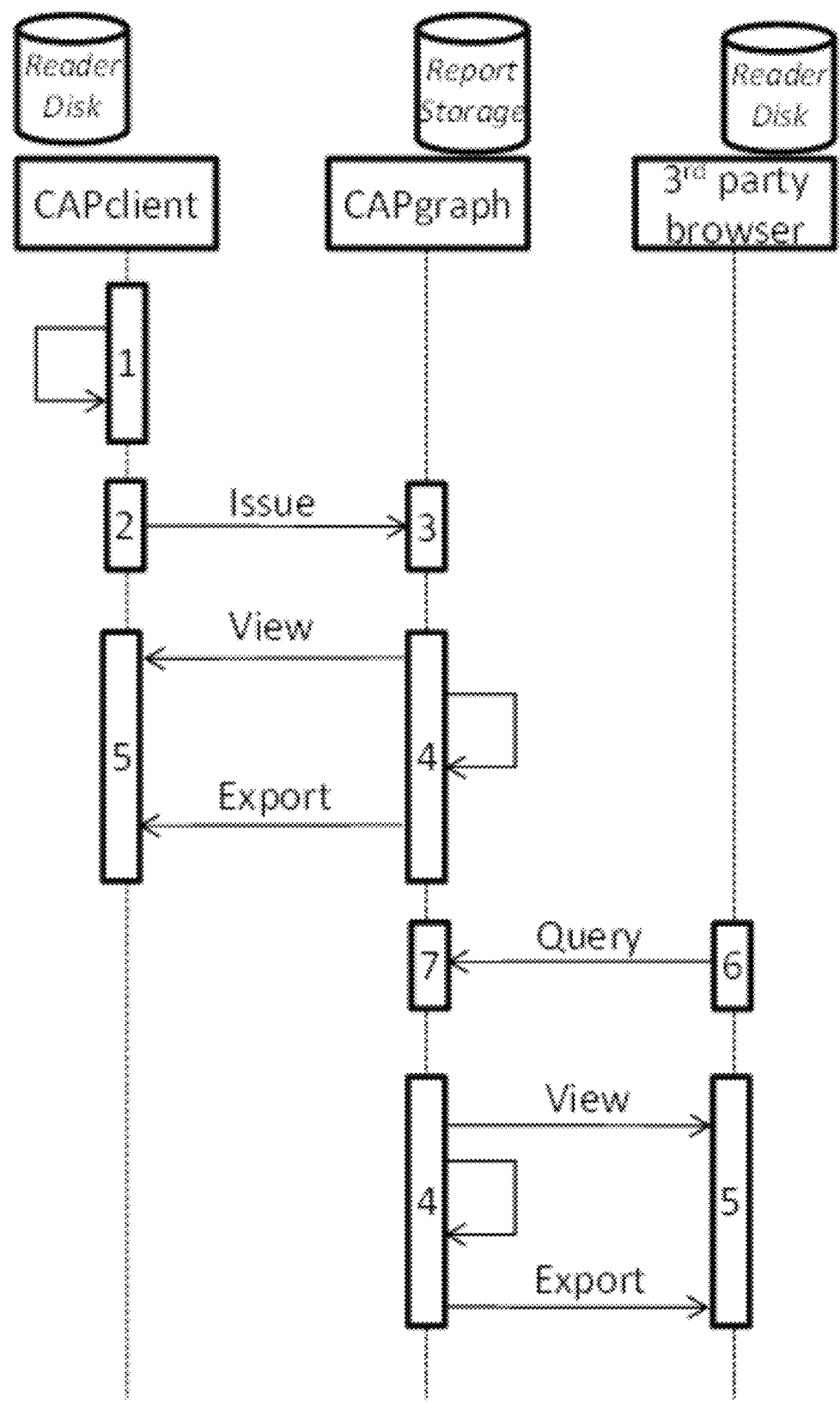
FIG. 8 shows an example interaction between a client and a server to support a patient report generation sequence.
Figure 9A:
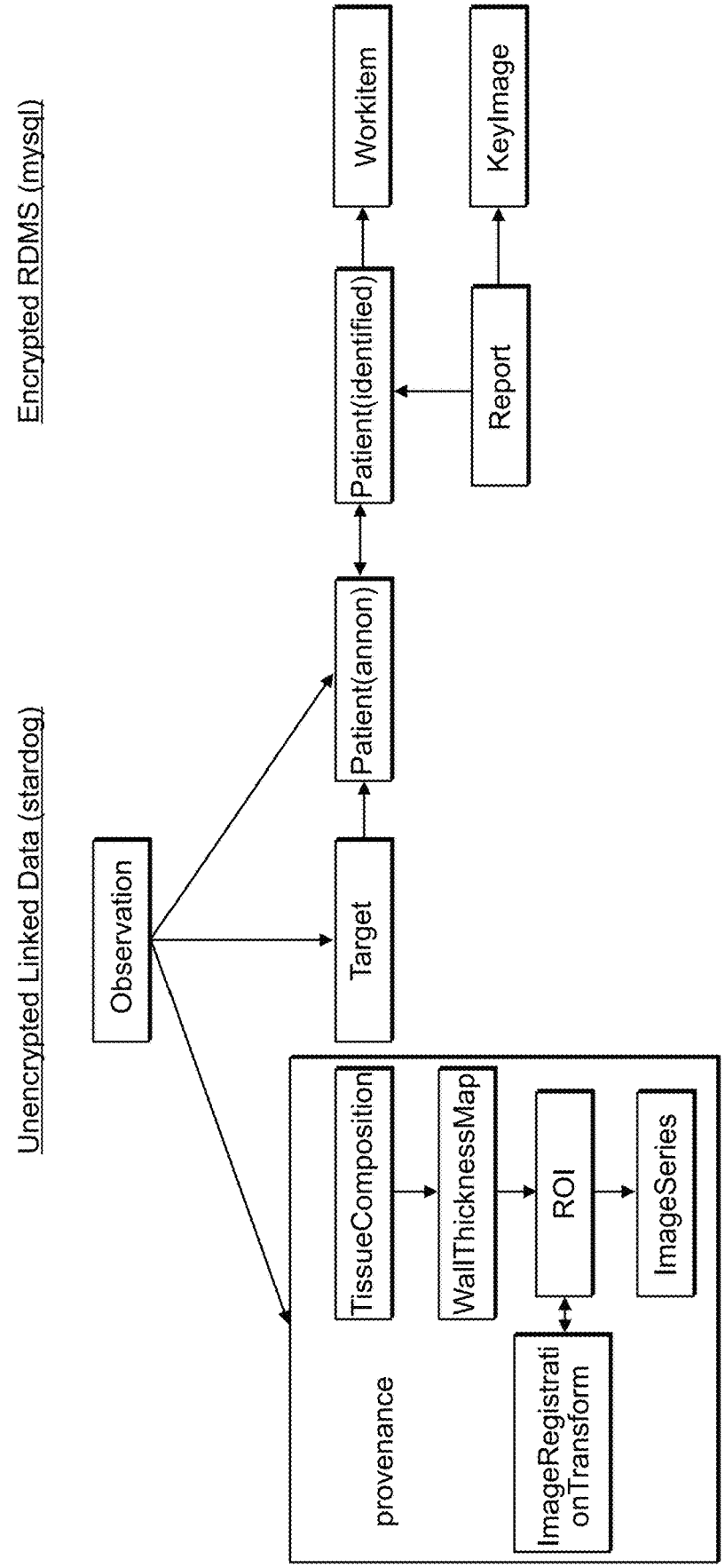
FIGS. 9a, 9b show exemplary relationships between encrypted and unencrypted data to support segregation of protected health information from data which may be accessed by surveillance or discovery applications.
Figure 9B:
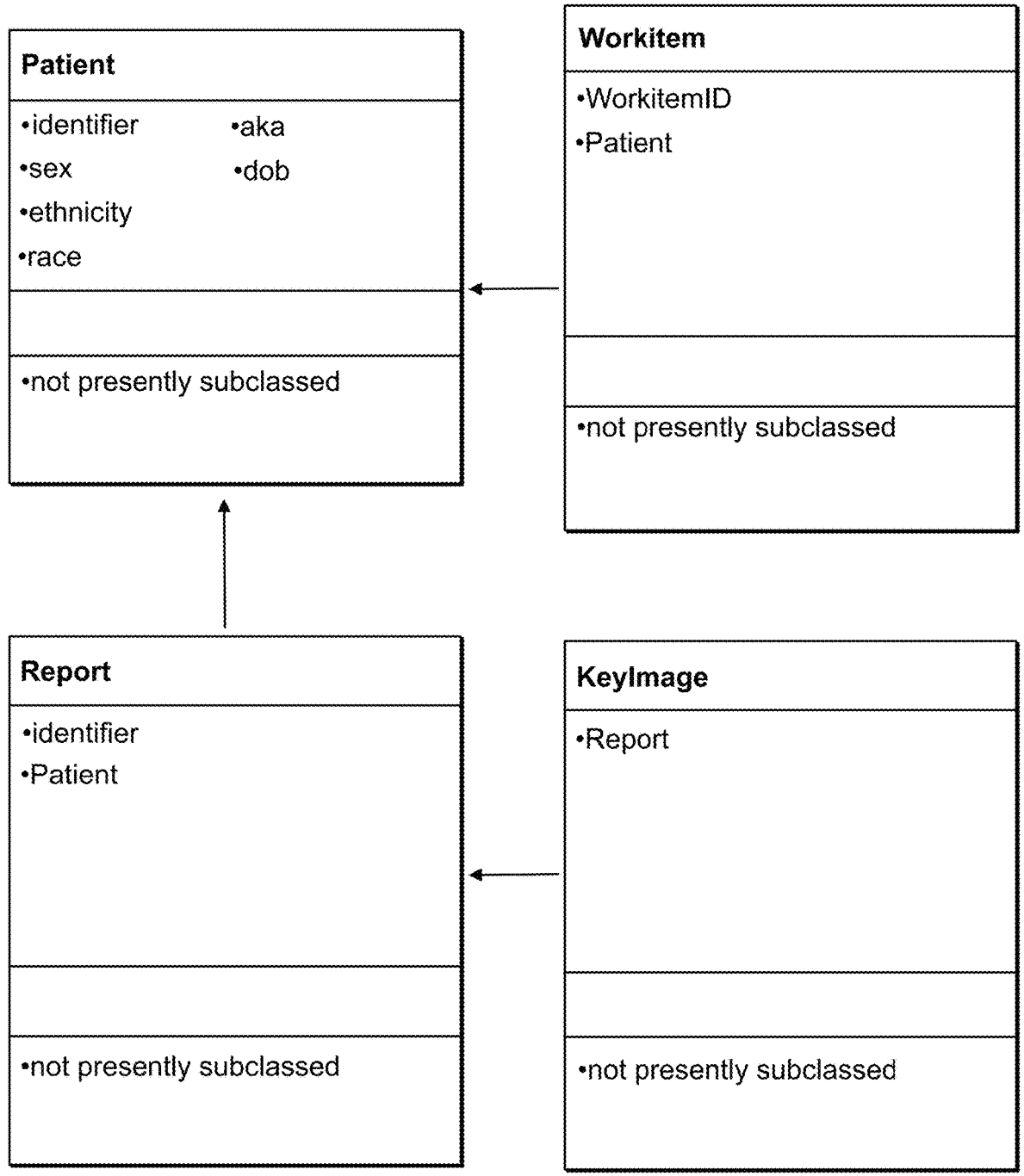

In another exemplary application and with reference to FIG. 8, a client application performs image processing etc. to make report content. It then securely packages this data and transitions to the server-side reporting application, obtaining an ID used in subsequent steps. The server catches the http multipart, stores the issued report instance, potentially logs a billing item ID to charge against, and return the report ID to the client which will be used to host the viewing/editing session as well as provide continuity for maintaining versions and provenance. FIGS. 9a, 9b depict how individual identity of patients is protected and segregated from quantitative information in such a way that relationships to specific patients are available for clinical care by clinicians with access rights but not otherwise, however, enabling use of the data for research purposes provided adequate consent is in place using institutionally-approved processes for data access to anonymized data.

Figures 10A, 10B:
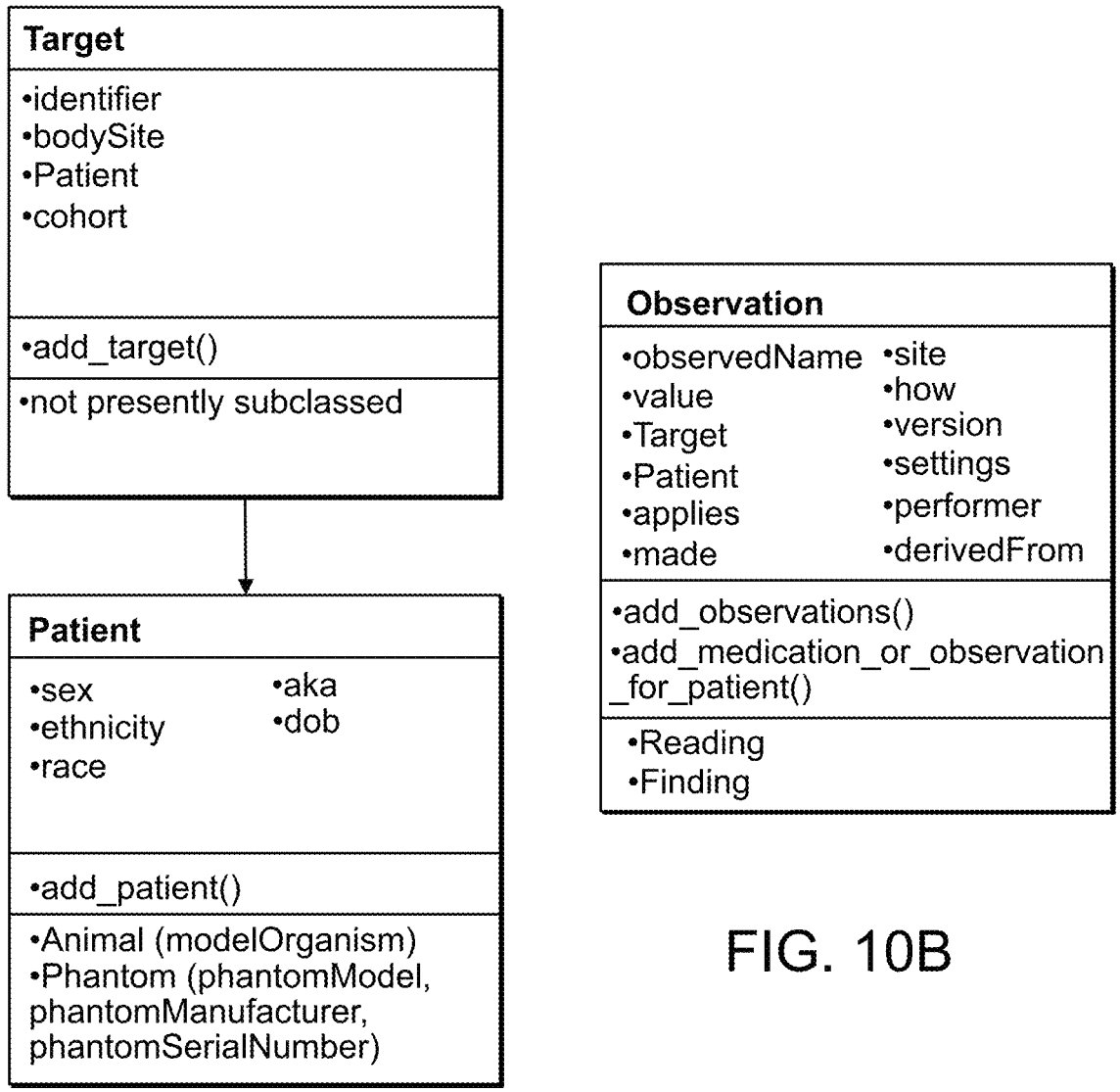
FIGS. 10a, 10b shows principal classes with exemplary data and methods used in a patient encounter reporting application including longitudinal trend analysis.
Figure 11:
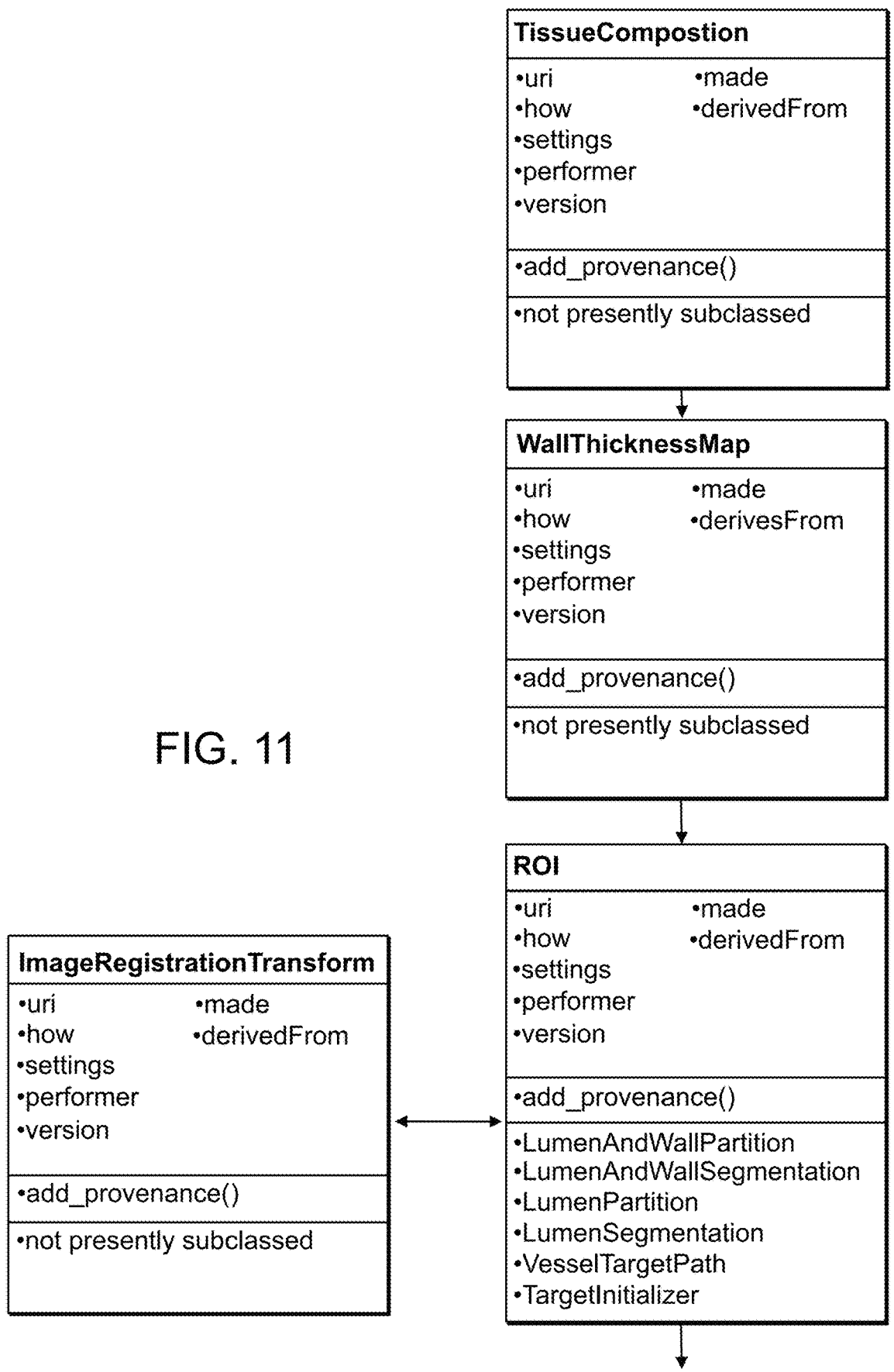
FIG. 11 shows a subset of classes which may be stored within the graph database used to represent provenance of clinical readings.
Figure 11:
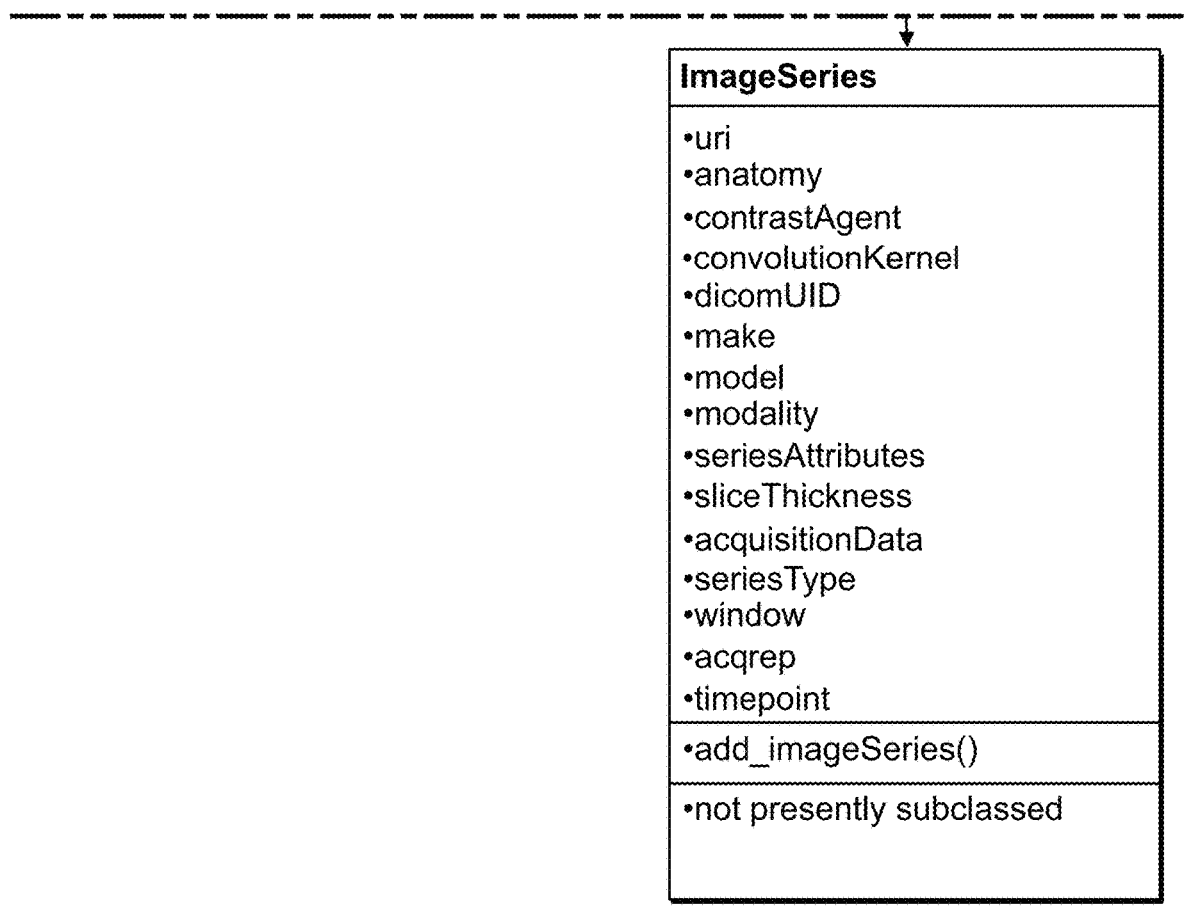

The view session draws from data as depicted in FIGS. 10a, 10b and 11 for report composition, and the data depicted in FIG. 12 is available on request to substantiate the results and document provenance. The view session has the facility to trap an export signal and store the returned PDF, DICOM S/R, HL7 CDA, or other formatted result to disk or transfer to EMR.

By virtue of having assessed analytic/technical performance using the invention, as well as all detailed provenance, all observations are supported by:
A detailed audit trail of what they were based on, who processed steps, how the steps were undertaken, and the settings and tool versions used
Detailed performance metrics of the uncertainty of the observed value, according to the mantra "no measurement is complete without a statement as to its uncertainty"

The server may also support a function to compose a list of applicable reports based on a user identity from a browser Query the reports that are available for the institution(s) with which the user has a relationship, allowing selection which uses ID.

All functions are password protected, transfers of protected health information are encrypted, and users may have 1 or more institutional affiliations for billing purposes and in filtering report listings.

More specifically, a client workstation initiates a report generation sequence by sending an HTTP multipart form POST to the API endpoint (using Qt HTTP multipart class http://doc.qt.io/qt-4.8/qhttpmultipart.html)
To create a new workitem in the database
POST API_ENDPOINT/workitems?identifier={workItemID}
Example:
http://bach.bbmsc.com:8001/workitems?identifier=wi118912427
The contents of the multipart POST are several "files" described below.

| File Name | Required | File MIME Type | Description |
|---|---|---|---|
| workitem | Yes | application/json | The workItem block from the workItemList |

For each target, the following files are also included in the multipart POST.

| File Name | Required | File MIME Type | Description |
|---|---|---|---|
| {targetID}:readings | No | application/json | The readings file for the target |
| {targetID}:{unique name} | No | application/octet-stream | PNG formatted images of a cross-section |

This returns a JSON document which includes the workitem resource identifier (which is different from the actual workItemID). This resource ID is needed for all other interactions with the workitem.

Example Return Document

```
{
    "id":
        "53969389163879937704"
}
```

To Launch the Report Generator UI: Redirect a browser (or Qts browser widget) to
APP_SERVER/#/workitem/{workitem_resourceID}/
Example:
http://bach.bbmsc.com:8000/#/workitem/53969389163879937704
To create the report,
POST API_ENDPOINT/workitem/{workitem_resource}/report
The contests of the POST are a JSON document with any cross-section identifiers that should be selected by default. This method returns the HTML report.
To return a PDF formatted version of the report
POST API_ENDPOINT/workitem/{workitem_resource}/report?format=pdf Assess the progression of target lesion and/or Patient Summary Measures The Compare Multiple Timepoints function is to track target lesions over time.

Likewise, the Reporting application may use the triple-store to retrieve information across multiple encounters, and thereby enable a longitudinal trend analysis of given identified lesions or targets, as well as summary measures for the patient as a whole.

Evaluate Experimental Cohorts

In one exemplary instance, apart from the data, functional workflows are distributed over three separate applications; Trainer, Analyzer and Cohort Tool. Trainer establishes classification models, Analyzer uses locked down classification models. Analyzer refers only to a single patient which may or not be a subject within a cohort; cohort tool applies to cohorts of subjects and calculates statistics accordingly.

| Trainer | Analyzer | System Function |
| --- | --- | --- |
| Prepare Test Subjects | Curate Subject Acquisition | Curate Subject Acquisition |
| | Delineate Field | Register multiple data streams across a field |
| | | Segment organs, vessels, lesions, and other application-specific objects |
| | | Reformat anatomy for specific analyses |
| | Delineate Target | Register multiple data streams at a locale |
| | | Fine-grained segmentation |
| Optimize Classifiers by Partitioning and Looping | | Measure size and/or other relevant anatomic structure |
| | | Extract whole-target features |
| | Delineate Sub-target regions | Split target into sub-targets according to application |
| | | Sub-target specific calculations |
| | Delineate Components | (Re-) Segment Component |
| | | Calculate Readings |
| | | Visualize Probability Map |
| N/A | Generate Patient Report | Generate Patient Report |
| N/A | Create Ground Truth Map | (Optional) Create Ground Truth Map |
| N/A | Compare Multiple Timepoints | (Optional) Compare Multiple Timepoints |

The purpose of Cohort Tool is to aggregate evidence across cohorts or research purposes, whether by a user for their research or to characterize performance of a CAP system relative to its intended uses. Specifically, the Cohort Tool is developed to allow users to:

Characterize the method relative to intended use.
Apply the existing tools and/or extend them.

There are two fundamental reasons for Cohort Tool: first, it can be used to validate to validate CAP systems for regulatory purposes, and also, users use it for their own research purposes. Regulatory approval for clinical use and regulatory qualification for research use depend on demonstrating proof of performance relative to the intended application of the biomarker: In one embodiment, triples are used in the Cohort Tool.

In a defined patient population,
For a specific biological phenomenon associated with a known disease state,
With evidence in large patient populations, and
Externally validated.

| Cohort Tool | System Function |
| --- | --- |
| Technical Performance | Bias and Linearity Analysis |
| | Repeatability and Reproducibility-Nonparametric |
| | Repeatability and Reproducibility-Parametric |
| | Repeatability and Reproducibility-probability density function of error |
| | Region of Interest Boundary Concurrence-sensitivity, specificity, and overlap on a voxel basis |
| Algorithm Comparison | Hypothesis Testing |
| | Test for Interchangeability |
| Clinical Performance | Exploratory Data Analysis-scatter plots and regression lines |
| | Treatment Effect Analysis-assessing differences using different study conditions |
| | ROC (AUC) Analysis-true versus false positive (negative) values |
| | Cox Hazard Analysis |

In one exemplary instance, the semantic search ability component is the "Specify" component described in Andrew J. Buckler, et al., A Novel Knowledge Representation Framework for the Statistical Validation of Quantitative Imaging Biomarkers, J Digit Imaging (2013) 26:614-629, which is incorporated by reference herein in its entirety and for all purposes.

Specify is a web-based component and helps a user to traverse concepts in the ontology according to their relationships to create statements represented as Resource Description Framework (RDF) triples, and to store them in an RDF store. Specify uses a repository of ontologies.

The process in "Specify" is continued, as long as additional information is available, or extended as new information emerges. As this process is continued through the curation of additional information from published and other sources, a complete specification for the desired target emerges. This specification is interpreted as a set of hypotheses that may be tested.

An exemplary component for accessing predetermined data services, generating queries from the plurality of RDF triples in order to collect data sets, and using the queries and the predetermined data services to collect data sets is the "Formulate" component in Andrew J. Buckler, et al., A Novel Knowledge Representation Framework for the Statistical Validation of Quantitative Imaging Biomarkers, J Digit Imaging (2013) 26:614-629

As stated in J Digit Imaging (2013) 26, p. 619, "Formulate uses the triples from Specify to generate queries to collect data sets that can be used to test the hypothesis. Formulate traverses the graph defined by the triples to a root-target entity (e.g. CTImage)—and leverages the nodes traversed to construct criteria for the query. These queries are sent to services providing the target entities. Formulate is defined as an implementation of the following behavioral model.

Data retrieved by Formulate or otherwise directly obtained is organized according to a set of conventions that draws from the popular ISA-Tab model. In order to facilitate the organization of highly complex imaging research data in a form that balances flexibility with the need for standard representation, and in such a way as to enable mixed-discipline research with the sister field of various -omics technologies, an ISA-Tab "like" convention is adopted. Investigation, Study, and Assay are the three key entities around which the ISA-Tab framework is built; these assist in structuring metadata and describing the relationship of samples to data."

In other exemplary instances, scripted programs written in, for example, Python, may build and use information in the knowledgebase, for example, using scripted operations called process_ground_truth can provide capability to Record Annotations and/or Phenotypes from Histology and/ or Other Truth References:
for dataset in args.datasets[0].split(','):
load the dataset
loop over patients
  # load the target data & annotations
  # loop over targets
    # get set of non-excluded histology sections
    # loop over histology_section in specimen['sections']:
      # process histology_sections_for_CAPgraph_storage
      # perform image processing
      # recursively determine and store provenance as chain of objects
      # Append the readings to the prediction set In other exemplary instances, a scripted operation called process_workitem_list can provide capability to execute quantitative imaging computations and/or harvest observations from them across large collections:
loop over inputList, creating resultList
for target in inputWI.targets:
  # prepare target input files that had resulted from previous user sessions or prior automated runs
  # set up the radiology image files
  # establish processing settings from defaults but with any overrides included
  # perform image processing at all cross sections along path
  # add provenance records in the knowledgebase to record the processing details
  # harvest readings (either from vc if not skip_ip else preexisting) (annotating the readings with details on their provenance)
  # also get any comparison readings at listed section locations, then harvest those too
  # save summary results to knowledgebase In other exemplary instances, a scripted operation called make_ranges: can provide capability to draw from knowledgebase to create lists of cases matching similarity criteria:
setup list of observation names for matching
set up list of phenotypes to be matched
compute_ranges of the measurands
create pivot table of observatiosn to phenotypes
compute_search_indeces
save results back to knowledgebase for later access Application in Determining Technical (Analytic) Performance One use case enabled by the invention is to compute the technical performance of a diagnostic measurement made by quantitative imaging applications such as those depicted in FIG. 13. That use case is implemented as follows.

Prior to computing technical performance, quantitative readings (measurements) are computed across a range of patient images and time points. Readings apply to a particular target of the patient. For example, from vascuCAP, a target is one or more vessels—like the Carotid Arteries. Some targets are pre-selected to be part of a performance evaluation group. An exemplary reading for a target in the vascuCAP_CT_Development Reference Dataset group is presented herein below:

```
{
    @type: Reading,
    @id: 12345,
    Patient: 54321,
    Target: 018765,
    BodySite: LeftInternalCarotidArtery,
    name: MaxStenosisByDiameter,
    value: 75,
    performer: vascuCAP,
    made: 2015-10-01,
    applies: 2015-09-25,
}
```

Performers of the readings may be computation algorithms (like vascuCAP) or may be human performers. One of the performers is specified to be the system under test (vascuCAP in this example) while other performers are specified to the reference or ground truth for the reading.

These readings are stored in an instance of an RDF (a.k.a. graph) database product. The steps to compute technical performance are:
1. A user can request the group resource of a group using its human-readable identifier.
2. A user uses a REST API to request the computation of performance of the returned group resource.
3. The server uses SPARQL to query for all Targets in the user specified group—like the VascuCAP_CT_Development Reference Dataset group.
4. For each target, use SPARQL to query for all readings on that target.

5. Sort according to the reading "made" date/time property and keep only the most recent readings (or alternatively retin replicates to determine intra- or inter-reader performance).
6. For each reading name, match up the reading made by the "under-test" performer to the reading(s) made by the reference/truth performers.
7. For each reading name, compute relevant statistics and metrics used to evaluate technical performance. Examples include but are not limited to such metrics as Bias, Offset, Precision, Standard Deviation, RMS Error and Limit of Quantitation (LOQ).
   a. The triplestore knowledgebase itself is used to discover what readings exist and may also hold look-up tables to set a more specific scope of analysis.
   b. Additionally, lookup performance standards for the reading. The performance standard may be specified as the performance of a reference system (like a predicate device).
8. Store all computed metrics in a JSON file or store those metrics in the triplestore knowledgebase.
9. A user can now request the performance results.
10. The JSON file returned is transformed into an HTML report (a.k.a. Dashboard) and displayed to the user.

In other exemplary instances, a scripted operation called process_technical_performance may provide capability to discover relationship among observations in knowledgebase and compute analytic performance metrics based on them:

```
# for each of cutA and cutB
    # for each measurand meeting cut criteria
        # query for the observations in the knowledgebase
        # pre-process replicates
        # form set of anatomy aggregates based on what is
          found in the data
        # form sets of performer and how the performers
          made measurements
        # loop over all aggregates
            # loop over all performer X how combinations
              present in the aggregate:
            # now tunnel in to the analyses if there is anything
              to do
            # find true, reference, and measured values
            # based on what combinations are present,
              evaluate different statistical metrics such as
              bias, repeatability, interchangeability, agree-
              ment, etc.
# then do the inter-cut if two cuts have been requested
# compile results in files and write back instances of
  statistical metric classes to knowledgebase for later
  retrieval
```

In other exemplary instances, a scripted operation called optimize_settings can provide capability to combine process_workitem_list and process_technical_performance so as to evaluate the relative performance of differing settings for the purpose of optimizing the defaults for those settings on new cases:

```
# establish list of permutations over which to optimize settings and database and/or
  graph storage for the results to accumulate into
    # for j, override_list in enumerate(override_lists):
        # for i, workitem_list in enumerate(input_lists):
            # execute process_workitem_list,
        # execute process_technical_performance over the data for the override list
        # save summary results to knowledgebase for all metrics assessed for differeing
          settings
# an exemplary output, for example, and of course,
# arbitrary subsets based on whatever is actually available in CAPgraph.

```

| # measured | measured against ref | | | measured against measured | |
|---|---|---|---|---|---|
| # | Bias | IEC | Intra-reader | Inter-reader | Inter-cut |
| # MaxMaxWallThickness | x | x | x | x | x |
| # MaxStenosisByArea | x |  | x | x | x |
| # MaxStenosisByDiameter | x | x | x | x | x |
| # MaxDilationByArea | x |  | x | x | x |
| # MaxDilationByDiameter | x | x | x | x | x |
| # MaxRR | x | x | x | x | x |
| # LumenArea | x |  | x | x |  |
| # LumenMaD | x | x | x | x | x |
| # WallArea | x |  | x | x |  |
| # WallMaD | x | x | x | x | x |
| # LumenAndWallArea | x |  | x | x |  |
| # LumenAndWallMaD | x | x | x | x | x |
| # CALCArea | x |  | x | x |  |
| # CALCAreaProp | x |  | x | x |  |
| # CALCVol |  |  | x |  |  |
| # LRNCArea |  |  | x |  |  |

```
x
# LRNCAreaProp              x                           x
x
# LRNCVol                                               x
# FIBRArea                  x                           x
x
# FIBRAreaProp              x                           x
x
# FIBRVol                                               x
# IPHArea                   x                           x
x
# IPHAreaProp               x                           x
x
# IPHVol                                                x

# for each of the following anatomic sites:
# Carotid (union of left or right)
# RightCarotid
# LeftCarotid
# InternalCarotid (union of left or right)
# ExternalCaotid (union of left or right)
# Vertebral (union of left or right)
# RightVertebral
# LeftVertebral
# Femoral (union of left or right)
# RightFemoral
# LeftFemoral
# Aorta
# Coronary (union of left or right)
# RightCoronary
# LeftCoronary
# MainStem
# Circumflex
# LAD

# all but the inter-cut for each of cutA and B (except when B is None), and the last for cutA-
cutB.
```

See FIG. 8 for an example means organizing of tracking performance over time in a folder structure, or a "dashboard" display may be used to make this data available to web browsers.

Application to Establish Efficacy of a Diagnostic/Prognostic:

The accuracy in predicting patient outcome will be of interest for imaging biomarkers. Patient outcomes can be categorically assessed events at specific time points, such as the type of response at the end of a course of therapy, or whether the patient is alive at 1 year. Alternatively, patient outcomes can be defined as time-to-event, such as progression-free-survival (PFS) or overall survival (OS). The prediction problem will be approached from two complementary but distinct perspectives. They lead to two types of information, both of which are important in the evaluation of imaging as predictor such as the data depicted in FIGS. 9a through 11 when correlated with outcome data for the patients individually and using the cohort representation scheme, and the information made available as depicted in FIG. 12 provides necessary statistical validation results for interpreting the uncertainty and measurement error as it exists in the inputs. On this basis, a first perspective is the evaluation of the positive and negative predictive value of a test. In such an evaluation, biomarker values are used to classify patients as "responders" or "non-responders" by imaging, and rates of response or time-to-event data (e.g., PFS, OS) are compared between these groups of patients. A second perspective is when the goal of the biomarker is, for example, to predict survival.

Phenotype Predictive Modelling

By way of illustration but without loss of generality, we use an example of predicting atherosclerotic plaque type, following the AHA approved scheme first promulgated by Stary.

Segregated data sets (e.g., train and test) of plaque type samples are supported using the invention. In a specific example run, by way of illustration, there were 50 unique subjects, 383 total samples, and 35 measurements. The training and test set split comprised a training set had 252 subjects and the test set had 131 subjects. The response category was plaque type, and the types and corresponding frequencies are presented in Table 1.

TABLE 1

Frequency of each plaque type for the original data.

| | II | III | IV | V | VI | VI U | VII | VIII |
|---|---|---|---|---|---|---|---|---|
| Test | 1 | 4 | 6 | 49 | 36 | 1 | 27 | 7 |
| Train | 0 | 4 | 4 | 104 | 71 | 1 | 64 | 4 |

The objectives of these example analyses were to search for meaningful signal in the relationship between the predictors and plaque type. Models were developed using the following sets of predictors by way of illustration:
1) All predictors
2) CALCArea, CALCAreaProp, LRNCArea, LRNCAreaProp, LumenAndWallArea, LumenArea, and WallArea
3) The predictors in 2 plus FIBRArea, FIBRAreaProp, IPHArea, and IPHAreaProp 4) The predictors in 3 plus THROMBArea, THROMBAreaProp, ULCArea, ULCAreaProp, VASCArea, and VASCAreaProp
5) Area predictors alone: CALCArea, LRNCArea, LumenAndWallArea, LumenArea, WallArea, FIBRArea, IPHArea, THROMBArea, ULCArea, and VASCArea
6) Prop predictors alone: CALCProp, LRNCProp, LumenAndWallArea, LumenArea, WallArea, FIBRProp, IPHProp, THROMBProp, ULCProp, and VASCProp For each predictor set, pre-processing steps may be taken prior to building predictive models. First, near zero variance predictors were removed. A near-zero variance predictor is defined as having few unique values relative to the number of samples and a high imbalance in the frequency of the values. Based on this definition, near-zero variance predictors contain very little information. Next, highly correlated predictors were removed. In this analysis, any predictor with a pairwise correlation greater than 0.9 with another predictor is identified. When two predictors are identified as being highly correlated, the predictor with the highest average correlation with the other predictors is removed. Details about how these pre-processing steps affected each predictor set are provided in the analysis section of each predictor set.

The following predictive models were trained: partial least squares, recursive partitioning, and random forests. Five repeats of 10-fold cross-validation was used as the cross-validation approach to identify the optimal values of the tuning parameter(s) for each model as well as to estimate the predictive performance for the each model. In one repeat of 10-fold cross-validation, all of the samples are randomly split into 10 groups. One group is held-out, while the remainder of the data is used to build a model. The model is then used to predict the held-out data, and these predictions are used to assess model performance. Then the same process is repeated for the next fold of data. This cross-validation process is then separately repeated 5 times. A brief explanation of each predictive model is provided below. Partial Least Squares (PLS) is a covariance-based method that seeks to find linear combinations of the original predictors in a way that optimally reduces the misclassification rate. These linear combinations split the predictor space by hyperplanes. Therefore, PLS is an optimal modeling tool when the response is best separated by a hyperplane. The number of latent variables is the tuning parameter for PLS. Recursive Partitioning Recursive partitioning (RPart) is a tree-based method that recursively splits the data into subsets that are more pure with respect to the classification outcome. This splitting essentially creates hypercubes in the predictor space, partitioning samples into regions of similarity of response category based on the predictors. The tuning parameter for the version of RPart used in these analyses is the depth of the tree. RPart models are highly interpretable, but are unstable. Instability means that small changes to the data can result in significant changes in the interpretation of the tree. Random Forests Random forests (RF) is a tree-based method built on an ensemble of trees. An RF model does the following process many times: selects a bootstrap sample of the training set and builds a tree on the bootstrap sample. Within each tree, a randomly selected number of predictors is chosen and the optimal split is selected only from that sample. Therefore, the tuning parameter for RF is the number of randomly selected predictors for each split. Building an ensemble of trees in this way reduces the variance seen by using just a single tree. RF predictions are more accurate and stable, but are not interpretable as compared to a recursive partitioning tree.

Application to Proving Surrogacy of Putative Biomarkers

The assessment framework for predictive markers stems from the accepted definition of a surrogate marker as being a measure which can substitute for a more difficult, distant, or expensive-to-measure endpoint in predicting the effect of a treatment or therapy in a clinical trial. Definitions of surrogacy revolve around the elucidation of the joint and conditional distributions of the desired endpoint, putative surrogate and their dependence on a specified therapy. Therefore, what may work adequately for a given endpoint and one type of therapy may not be adequate for the same endpoint and a different type of therapy. Disease screening calls for a prognostic marker where it is neither necessary nor possible to anticipate all the potential therapies for which a surrogate marker might be desired.

Nevertheless, as measurements are developed that capture more and more accurately the structure, functioning and tissue metabolism, it is posited that proposed biomarkers are on the causal pathway to the symptomatic disease and its clinical outcomes and can function as surrogate markers for at least one element of disease. Storage and representation of the data as described herein allows correlation of changes within a person over time between different elements of disease including different measures of structural change. Putative biomarkers must have adequate precision for estimating the joint relationship between proposed biomarkers and desired endpoints. The present invention makes it possible to identify a number of promising biomarkers for use in early development of treatments and that can be tested in trials as surrogates for treatment effects.

Surrogacy means more than a demonstrable or even a strong association between the desired endpoint and the proposed surrogate and original definitions have been criticized as being limited in scope and having fundamental shortcomings. Recent proposals in the context of meta-analysis get more to the heart of surrogacy. By correlating changes in the surrogate with changes in a primary endpoint, these approaches more directly address the surrogacy question, whether in cross-sectional and/or longitudinal settings.

Although these teachings has been described with respect to various embodiments, it should be realized these teachings are also capable of a wide variety of further and other embodiments within the spirit and scope of the appended claims.

What is claimed is:

1. A system for making imaging-derived information accessible to computational applications, the system comprising: one or more processors, and non-transitory computer usable media, having computer readable code embodied therein, wherein the computer readable code, when executed by the one or more processors, causes the one or more processors to:
produce a semantically expressive knowledge graph for a plurality of patients, where producing the knowledge graph includes for each of the plurality of patients:
characterizing the patient based on one or more elements of an identification scheme and storing the characterization of the patient in the knowledge graph, the identification scheme comprising demographics of the patient, observations about the patient, and diagnostic findings for the patient;
characterizing one or more anatomical regions of interest for the patient as targets to support tracking in the knowledge graph of at least one of a given anatomy, suspected pathology, confirmed pathology, or medical intervention at one or more timepoints;

storing access information to one or more medical images of each target at each one of said one or more timepoints in the knowledge graph;

performing a hierarchical analysis on the one or more medical images for each target at each time point, the hierarchical analysis including determining and storing in the knowledge graph each of (i) imaging features calculated from the one or more medical images, (ii) quantitative properties for objectively verifiable biological analytes derived from the imaging features, and (iii) phenotypes or predictive outcomes derived from the quantitative properties for the objectively verifiable biological analytes; and wherein the knowledge graph provides for semantic search ability, without requiring predefined queries.

2. The system of claim 1, wherein the computer readable code, when executed by the one or more processors, further causes the one or more processors to analyze the knowledge graph by proving or disproving a hypothesis related to at least one of: (i) tracking of a given anatomy, (ii) tracking of a suspected pathology, (iii) confirmation of a given pathology, or (iv) an effectiveness of a given medical intervention.

3. The system of claim 2, wherein the hypothesis is applied to one or more of clinical decision support, disease modeling, disease discovery research, developing a data set for training machine learning algorithm, and qualification of imaging biomarkers.

4. The system of claim 3, wherein the tested hypotheses provide evidence demonstrating proof of performance for regulatory approval for clinical use or regulatory qualification for research use.

5. The system of claim 1, wherein the computer readable code, when executed by the one or more processors, further causes the one or more processors to analyze the knowledge graph by querying the knowledge graph to determine at least one of (i) clinical relevance of measurements of a given anatomy, (ii) clinical relevance of measurements of a suspected pathology, (iii) confirmation of a given pathology, or (iv) an effectiveness of a given medical intervention.

6. The system of claim 1, wherein the computer readable code further causes the one or more processors to evaluate phenotype predictors at one or more time points so as to characterize a physiological condition at a given time or characterize how a physiological condition changes across time.

7. The system of claim 1, wherein the computer readable code, when executed by the one or more processors, further causes the one or more processors to use the knowledge graph to perform a statistical evaluation of performance of the hierarchical analysis across a plurality of patients.

8. The system of claim 7, wherein the knowledge graph includes ground truth or validation reference information for one or more of the levels of the image analysis, wherein the statistical evaluation of performance includes a statistical evaluation of clinical performance comparing one or more of the levels of image analysis to the ground truth or validation reference information.

9. The system of claim 8, wherein the ground truth or validation reference information is derived independently from the hierarchical analysis.

10. The system of claim 8, wherein the ground truth or validation reference information includes at least one of: (i) a objectively true measurement of one or more of the quantitative properties of the biologically objective analytes, (ii) a subjective determination of an image feature, a biologically objective analyte, a phenotype or a predictive outcome by an expert clinician or other alternative source or (iii) an observed outcome.

11. The system of claim 7, wherein the statistical evaluation of performance includes a statistical evaluation of analytical performance including determining one or more performance metrics characterizing one or more of the levels of image analysis.

12. The system of claim 7, wherein the statistical evaluation of performance includes one or more of the following metrics: offset, precision, standard deviation, RMS Error, or limit of quantitation (LOQ).

13. The system of claim 7, wherein performing the statistical evaluation of performance includes performing scripted operations executed in a batch.

14. The system of claim 7, wherein the computer readable code, when executed by the one or more processors, further causes the one or more processors to extend the knowledge graph to include the results of the statistical evaluation of performance.

15. The system of claim 7, wherein querying information from the knowledge graph returns both queried results and corresponding statistical evaluation of performance for the queried results.

16. The system of claim 7, wherein the computer readable code, when executed by the one or more processors, further causes the one or more processors to optimize the hierarchical analysis in the knowledge graph based on the statistical evaluation of performance.

17. The system of claim 7, wherein the computer readable code, when executed by the one or more processors, further causes the one or more processors to validate the hierarchical analysis based on the statistical evaluation of performance.

18. The system of claim 17, wherein validating the hierarchical analysis includes validation for context of use including for one or more of: (i) a patient population, (ii) a pathology, (iii) a diagnostic purpose or (iv) a treatment type.

19. The system of claim 18, wherein validating the hierarchical analysis further includes determining a scope of generalization of the context of use.

20. The system of claim 7, wherein using the knowledge graph to perform a statistical evaluation of performance includes assessment of confidence in changes over time of elements or connections reflected in the knowledge graph.

21. The system of claim 7, wherein the computer readable code, when executed by the one or more processors, further causes the one or more processors to report information from the knowledge graph for a single patient, where the report incorporates error propagation information derived from the statistical performance evaluation.

22. The system of claim 1, wherein the knowledge graph is comprised of a set of RDF triples.

23. The system of claim 22 wherein the computer readable code, when executed by the one or more processors, further causes the one or more processors to:
  access predetermined data services;
  generate queries from the plurality of RDF triples; and
  use the queries and the predetermined data services to collect data sets from the knowledge graph according to inclusion criteria set after the data services are in operation.

24. The system of claim 23 wherein the data sets are used to test a hypothesis, the hypothesis related to at least one of: (i) tracking of a given anatomy, (ii) tracking of a suspected pathology, (iii) confirmation of a given pathology, or (iv) an effectiveness of a given medical intervention.

25. The system of claim 23 wherein the queries are SPARQL queries on the data services implemented so as to expose the SPARQL endpoints.

26. The system of claim 1, wherein the sematic search ability includes querying the knowledge graph using SPARQL queries so as to expose SPARQL endpoints.

27. The system of claim 1, wherein the knowledge graph does not require predefined relationships between data elements in the knowledge graph.

28. The system of claim 1, wherein information in the knowledge graph on the individual identity of a patient is stored in an encrypted data repository and accessed with encryption and non-identifiable information in the knowledge graph is stored in an non-encrypted data repository and accessed without encryption using anonymized keys.

29. The system of claim 1, wherein the knowledge graph includes a detailed audit trail of creation including contributor information and how, when and what contributions were made.

30. The system of claim 1, wherein the knowledge graph is iteratively updated using an artificial intelligence approach based on a blackboard architecture model.

31. The system of claim 1, wherein the knowledge graph includes a plurality of interconnected graphs distributed across separate computers or networks.

32. The system of claim 1, wherein the knowledge graph includes causal relationships across different biological scales.

33. The system of claim 1, wherein the hierarchical analysis incorporates one or more non-imaging inputs into a determination of analytes.

34. The system of claim 1, wherein the computer readable code, when executed by the one or more processors, further causes the one or more processors to optimize a treatment for a patient based on the knowledge graph.

35. The system of claim 1, wherein the computer readable code, when executed by the one or more processors, further causes the one or more processors to identify, based on the knowledge graph, biomarkers for use in early development of treatments that can be tested in trials as surrogates for treatment effects.

36. The system of claim 35, wherein the identification of the biomarkers is based on inference.

37. The system of claim 35, wherein the identification of the biomarkers is based on joint and conditional probabilities.

38. The system of claim 1, wherein the computer readable code, when executed by the one or more processors, further causes the one or more processors to apply one or more predictive models to derive phenotype information from a patient based on the knowledge graph.

39. The system of claim 1, wherein the identification scheme includes characterization across a plurality of biological scales.

40. The system of claim 1, wherein the knowledge graph supports the collection and summary of evidence for clinical relevance, validity, and/or utility.

41. The system of claim 1, wherein the knowledge graph includes multi-scale modeling which is used to determine causal relationships between biomarkers, pathology and clinical outcomes.

42. The system of claim 41, wherein the multi-scale modeling elucidates both pre-symptomatic and clinical disease processes.

43. The system of claim 1, wherein the computer readable code, when executed by the one or more processors, further causes the one or more processors to determine a causal relationship between biomarkers, pathology and clinical outcomes.

44. The system of claim 1, wherein the computer readable code, when executed by the one or more processors, further causes the one or more processors to use inference to establish a strength of surrogacy of proximal markers relative to a distal endpoint.

45. The system of claim 44, wherein using inference includes using performance metrics of the uncertainty in elements or connections reflected in the knowledge graph.

46. The system of claim 44, wherein using inference includes using predictive modeling based on the knowledge graph to determine surrogate markers.

47. The system of claim 1, wherein the knowledge graph includes linked data across different contexts of use.

48. The system of claim 1, wherein the computer readable code, when executed by the one or more processors, further causes the one or more processors to determine personalized diagnostics based on performing inferential reasoning in the knowledge graph to optimize their treatment plan.

* * * * *